US010875849B2

(12) United States Patent
Li et al.

(10) Patent No.: US 10,875,849 B2
(45) Date of Patent: Dec. 29, 2020

(54) SOLID FORMS OF (E)-3-[2-(2-THIENYL)VINYL]-1H-PYRAZOLE

(71) Applicant: ANGION BIOMEDICA CORP., Uniondale, NY (US)

(72) Inventors: An-Hu Li, Commack, NY (US); Satish Kumar Sakilam, Harrison, NJ (US); Dong Sung Lim, Fair Lawn, NJ (US)

(73) Assignee: ANGION BIOMEDICA CORP., Uniondale, NY (US)

(*) Notice: Subject to any disclaimer, the term of this patent is extended or adjusted under 35 U.S.C. 154(b) by 0 days.

(21) Appl. No.: 16/942,182

(22) Filed: Jul. 29, 2020

(65) Prior Publication Data
US 2020/0369654 A1  Nov. 26, 2020

Related U.S. Application Data

(63) Continuation of application No. PCT/US2020/027710, filed on Apr. 10, 2020.

(60) Provisional application No. 62/832,519, filed on Apr. 11, 2019.

(51) Int. Cl.
C07D 409/06 (2006.01)

(52) U.S. Cl.
CPC ........ C07D 409/06 (2013.01); C07B 2200/13 (2013.01)

(58) Field of Classification Search
None
See application file for complete search history.

(56) References Cited

U.S. PATENT DOCUMENTS

| 4,806,535 | A | 2/1989 | Faith et al. |
|---|---|---|---|
| 5,246,951 | A | 9/1993 | Galet et al. |
| 5,837,676 | A | 11/1998 | Goldberg et al. |
| 5,919,759 | A | 7/1999 | Goldberg et al. |
| 5,962,490 | A | 10/1999 | Chan et al. |
| 5,965,523 | A | 10/1999 | Goldberg et al. |
| 5,997,868 | A | 12/1999 | Goldberg et al. |
| 6,011,009 | A | 1/2000 | Goldberg et al. |
| 6,013,624 | A | 1/2000 | Goldberg et al. |
| 6,248,722 | B1 | 6/2001 | Morishita et al. |
| 6,258,787 | B1 | 7/2001 | Isner |
| 6,303,126 | B1 | 10/2001 | Nakamura et al. |
| 6,432,406 | B1 | 8/2002 | Goldberg et al. |
| 6,437,006 | B1 | 8/2002 | Yoon et al. |
| 6,498,144 | B1 | 12/2002 | Goldberg et al. |
| 6,566,098 | B1 | 5/2003 | Chan et al. |
| 6,589,997 | B2 | 7/2003 | Pillarisetti et al. |
| 6,610,726 | B2 | 8/2003 | Pillarisetti et al. |
| 6,677,333 | B1 | 1/2004 | Seko et al. |
| 6,699,837 | B2 | 3/2004 | Nakamura |
| 6,855,728 | B2 | 2/2005 | Pillarisetti et al. |
| 6,994,857 | B2 | 2/2006 | Rosen et al. |
| 7,192,976 | B2 | 3/2007 | Zembower et al. |
| 7,250,437 | B2 | 7/2007 | Zembower et al. |
| 7,265,112 | B2 | 9/2007 | Zembower et al. |
| 7,648,978 | B2 | 1/2010 | Zembower et al. |
| 7,674,790 | B2 | 3/2010 | Ugwu et al. |
| 7,879,898 | B1 | 2/2011 | He |
| 8,193,177 | B2 | 6/2012 | Paka |
| 8,580,834 | B2 | 11/2013 | Zembower et al. |
| 8,772,326 | B2 * | 7/2014 | Cai ........................ A61K 9/145 514/406 |
| 9,663,471 | B2 | 5/2017 | Zembower et al. |
| 2002/0183325 | A1 | 12/2002 | Martin et al. |
| 2003/0022924 | A1 | 1/2003 | Pillarisetti et al. |
| 2003/0022934 | A1 | 1/2003 | Heil et al. |
| 2003/0045559 | A1 | 3/2003 | Pillarisetti et al. |
| 2003/0060403 | A1 | 3/2003 | Nakamura |
| 2003/0073692 | A1 | 4/2003 | Pulici |
| 2003/0125247 | A1 | 7/2003 | Rosen et al. |
| 2003/0216459 | A1 | 11/2003 | Pillarisetti et al. |
| 2004/0180882 | A1 | 9/2004 | Zembower et al. |
| 2005/0096372 | A1 | 5/2005 | Pillarisetti et al. |
| 2005/0113369 | A1 | 5/2005 | Zembower et al. |
| 2005/0192331 | A1 | 9/2005 | Zembower et al. |
| 2006/0063767 | A1 | 3/2006 | Javaid et al. |
| 2008/0015243 | A1 | 1/2008 | Zembower et al. |
| 2008/0070961 | A1 | 3/2008 | Reichwein et al. |
| 2010/0137285 | A1 | 6/2010 | Zembower et al. |
| 2010/0168065 | A1 | 7/2010 | Vialard et al. |
| 2010/0256117 | A1 | 10/2010 | Paka |
| 2011/0098304 | A1 | 4/2011 | Panicker et al. |
| 2011/0184038 | A1 | 7/2011 | Cai et al. |
| 2011/0230407 | A1 | 9/2011 | Yuzhakov |
| 2013/0136804 | A1 | 5/2013 | Zhang et al. |
| 2014/0256727 | A1 | 9/2014 | Cai et al. |

(Continued)

FOREIGN PATENT DOCUMENTS

| DE | 138770 A1 | 11/1979 |
|---|---|---|
| JP | 48-000713 | 1/1973 |

(Continued)

OTHER PUBLICATIONS

International Search Report for PCT/US20/27710, 3 pages (dated Jun. 15, 2020).
Written Opinion for PCT/US20/27710, 8 pages (dated Jun. 15, 2020).
Almirante, N. et al., A General, [1+4] Approach to the Synthesis of 3(5)-Substituted Pyrazoles from Aldehydes, Tetrahedron Letters, 39: 3287-3290 (1998).
Anzaldi, M. et al., Synthesis and antimicrobial activity of heterocyclic ionone-like derivatives, European Journal of Medicinal Chemistry, 34(10): 837-842 (1999).
Attaby, F.A. et al., Reactions with Cyanothioacetamide and its Derivatives: Synthesis and Reactions of Several New Thieno- and Azolopyridine Derivatives, Phosphorus, Sulfur, Silicon and the Related Elements, 119:1-10 (1996).

(Continued)

Primary Examiner — Kamal A Saeed
(74) Attorney, Agent, or Firm — Choate, Hall & Stewart LLP; Kristen C. Buteau; Erica M. D'Amato

(57) ABSTRACT

The present disclosure provides solid forms of (E)-3-[2-(2-thienyl)vinyl]-1H-pyrazole, compositions thereof, and methods of making and using the same.

19 Claims, 33 Drawing Sheets

(56) References Cited

U.S. PATENT DOCUMENTS

| | | |
|---|---|---|
| 2014/0256780 A1 | 9/2014 | Zembower et al. |
| 2015/0141382 A1 | 5/2015 | Kamat et al. |
| 2018/0009793 A1 | 1/2018 | Cai et al. |
| 2019/0375739 A1 | 12/2019 | Cai et al. |
| 2019/0382348 A1 | 12/2019 | Zembower et al. |

FOREIGN PATENT DOCUMENTS

| | | |
|---|---|---|
| JP | 02-193994 | 7/1990 |
| JP | 11-288112 | 10/1999 |
| WO | WO-95/01973 A1 | 1/1995 |
| WO | WO-98/18466 A2 | 5/1998 |
| WO | WO-01/02369 A2 | 1/2001 |
| WO | WO-01/34650 A1 | 5/2001 |
| WO | WO-02/02593 A2 | 1/2002 |
| WO | WO-2003/043958 A1 | 5/2003 |
| WO | WO-2003/057225 A2 | 7/2003 |
| WO | WO-2004/009599 A1 | 1/2004 |
| WO | WO-2004/058721 A2 | 7/2004 |
| WO | WO-2006/036981 A2 | 4/2006 |
| WO | WO-2006/060654 A2 | 6/2006 |
| WO | WO-2006/078941 A2 | 7/2006 |
| WO | WO-2009/000673 A2 | 12/2008 |
| WO | WO-2009/064422 A2 | 5/2009 |
| WO | WO-2010/005580 A2 | 1/2010 |
| WO | WO-2010/068287 A2 | 6/2010 |
| WO | WO-2011/019400 A2 | 2/2011 |
| WO | WO-2011/119869 A1 | 9/2011 |
| WO | WO-2011/126903 A2 | 10/2011 |
| WO | WO-2012/047826 A2 | 4/2012 |
| WO | WO-2012/058531 A2 | 5/2012 |
| WO | WO-2014/111493 A1 | 7/2014 |
| WO | WO-2014/145986 A1 | 9/2014 |
| WO | WO-2014/146059 A1 | 9/2014 |
| WO | WO-2020/210657 A1 | 10/2020 |

OTHER PUBLICATIONS

Boekelheide, V. and Fedoruk, N.A., Syntheses of Fused Aromatic Heterocycles by 1, 3-Dipolar Addition Reactions. 3-Azapyrrocolines, Journal of Organic Chemistry, 33(5):2062-2064 (1968).
Bromberg, J. et al., ANG-3777 Improves Outcomes in Patients with Delayed Graft Function: A Randomized, Double-Blind, Placebo-Controlled Phase 2 Trial with 12-Month Follow-Up, Abstract: TH-PO1213, presented at the American Society of Nephrology Annual Meeting in Washington, D.C., Nov. 5-10, 2019.
Bromberg, J. et al., BB3, a Hepatocyte Growth Factor-like Small Molecule, Improves Outcome in Kidney Transplant Recipients with Delayed Graft Function, presented at ASN Kidney Week 2015, Nov. 3-8, 2015, in San Diego, CA.
Bromberg, J. S., Renal Function Improvement Following ANG-3777 Treatment in Patients at High Risk for Delayed Graft Function After Kidney Transplantation, Transplantation (2020).
Chaparro, R. E. et al., Sustained functional improvement by hepatocyte growth factor-like small molecule BB3 after focal cerebral ischemia in rats and mice, Journal of Cerebral Blood Flow & Metabolism, 1-10 (2015).
Chau-Hua, et al., Hepatocyte growth factor gene therapy prevents radiation-induced liver damage, World Journal of Gastroenterology, 11(10):1496-1502 (2005).
ClinicalTrials.gov Identifier: NCT01286727, "Study to Improve Renal Function After Kidney Transplantation," (v1 dated Jan. 28, 2011, Published Jan. 28, 2011 and update posted Jan. 31, 2011 at https://clinicaltrials.gov/ct2/history/NCT01286727?V_1=View#StudyPageTop).
ClinicalTrials.gov Identifier: NCT01286727, "Study to Improve Renal Function After Kidney Transplantation," (v2 dated Dec. 20, 2011, Published Dec. 20, 2011 and update posted Dec. 21, 2011 at https://clinicaltrials.gov/ct2/history/NCT01286727?V_2=View#StudyPageTop).
ClinicalTrials.gov Identifier: NCT01286727, "Study to Improve Renal Function After Kidney Transplantation," (v3 dated May 21, 2013, Published May 21, 2013 and updated posted May 23, 2013 at https://clinicaltrials.gov/ct2/history/NCT01286727?V_3=View#StudyPageTop).
ClinicalTrials.gov Identifier: NCT01286727, "Study to Improve Renal Function After Kidney Transplantation," (v4 dated Oct. 6, 2014 Published Oct. 6, 2014 and update posted Oct. 8, 2014 at https://clinicaltrials.gov/ct2/history/NCT01286727?V_4=View#StudyPageTop).
ClinicalTrials.gov Identifier: NCT01286727, "Study to Improve Renal Function After Kidney Transplantation," (v5 dated May 4, 2015 Published May 4, 2015 and update posted May 5, 2015 at https://clinicaltrials.gov/ct2/history/NCT01286727?V_5=View#StudyPageTop).
ClinicalTrials.gov Identifier: NCT01539590, "Study to Evaluate the Safety and Activity of BB3 to Treat Heart Attack," (v1 dated Feb. 22, 2012, Published Feb. 22, 2012 and update posted Feb. 27, 2012 at https://clinicaltrials.gov/ct2/history/NCT01539590?V_1=View#StudyPageTop).
ClinicalTrials.gov Identifier: NCT01539590, "Study to Evaluate the Safety and Activity of BB3 to Treat Heart Attack," (v2 dated Jul. 13, 2012, Published Jul. 13, 2012 and update posted Jul. 17, 2012 at https://clinicaltrials.gov/ct2/history/NCT01539590?V_2=View#StudyPageTop).
ClinicalTrials.gov Identifier: NCT01539590, "Study to Evaluate the Safety and Activity of BB3 to Treat Heart Attack," (v3 dated Oct. 29, 2014, Published Oct. 29, 2014 and update posted Nov. 4, 2014 at https://clinicaltrials.gov/ct2/history/NCT01539590?V_3=View#StudyPageTop).
ClinicalTrials.gov Identifier: NCT01539590, "Study to Evaluate the Safety and Activity of BB3 to Treat Heart Attack," (v4 dated Nov. 7, 2014, Published Nov. 7, 2014 and update posted Nov. 21, 2014 at https://clinicaltrials.gov/ct2/history/NCT01539590?V_4=View#StudyPageTop).
ClinicalTrials.gov Identifier: NCT01561599, "Study on Delayed Graft Function Using Paired Kidneys," (v1 dated Mar. 22, 2012, Published Mar. 22, 2012 and update posted Mar. 23, 2012 at https://clinicaltrials.gov/ct2/history/NCT01561599?V_1=View#StudyPageTop).
ClinicalTrials.gov Identifier: NCT01561599, "Study on Delayed Graft Function Using Paired Kidneys," (v2 dated May 21, 2013, Published May 21, 2013 and update posted May 23, 2013 at https://clinicaltrials.gov/ct2/history/NCT01561599?V_2=View#StudyPageTop).
ClinicalTrials.gov Identifier: NCT01561599, "Study on Delayed Graft Function Using Paired Kidneys," (v3 dated Jan. 13, 2015, Published Jan. 13, 2015 and update posted Jan. 14, 2015 at https://clinicaltrials.gov/ct2/history/NCT01561599?V_3=View#StudyPageTop).
ClinicalTrials.gov Identifier: NCT01561599, "Study on Delayed Graft Function Using Paired Kidneys," (v4 dated Feb. 18, 2016, Published Feb. 18, 2016 and update posted Feb. 22, 2016 at https://clinicaltrials.gov/ct2/history/NCT01561599?V_4=View#StudyPageTop).
ClinicalTrials.gov Identifier: NCT02474667, "Reduce the Severity of DGF in Recipients of a Deceased Donor Kidney," (v1 dated Jun. 15, 2015, Published Jun. 15, 2015, and update posted Jun. 18, 2015 at https://clinicaltrials.gov/ct2/history/NCT02474667?V_1=View#StudyPageTop).
ClinicalTrials.gov Identifier: NCT02474667, "Reduce the Severity of DGF in Recipients of a Deceased Donor Kidney," (v10 dated Jan. 22, 2020, Published Jan. 22, 2020 and update posted Jan. 23, 2020 at https://clinicaltrials.gov/ct2/history/NCT02474667?V_10=View#StudyPageTop).
ClinicalTrials.gov Identifier: NCT02474667, "Reduce the Severity of DGF in Recipients of a Deceased Donor Kidney," (v2 dated Jul. 6, 2015, Published Jul. 6, 2015, and update posted Jul. 8, 2015 at hftps://clinicaltrials.gov/ct2/history/NCT02474667?V_2=View#StudyPageTop).
ClinicalTrials.gov Identifier: NCT02474667, "Reduce the Severity of DGF in Recipients of a Deceased Donor Kidney," (v3 dated Feb. 18, 2016, Published Feb. 18, 2016, and update posted Feb. 22, 2016 at https://clinicaltrials.gov/ct2/history/NCT02474667?V_3=View#StudyPageTop).

(56) References Cited

OTHER PUBLICATIONS

ClinicalTrials.gov Identifier: NCT02474667, "Reduce the Severity of DGF in Recipients of a Deceased Donor Kidney," (v4 dated Apr. 5, 2016, Published Apr. 5, 2016 and update posted Apr. 6, 2016 at https://clinicaltrials.gov/ct2/history/NCT02474667?V_4=View#StudyPageTop).
ClinicalTrials.gov Identifier: NCT02474667, "Reduce the Severity of DGF in Recipients of a Deceased Donor Kidney," (v5 dated Jan. 17, 2017, Published Jan. 17, 2017 and update posted Jan. 19, 2017 at https://clinicaltrials.gov/ct2/history/NCT02474667?V_5=View#StudyPageTop).
ClinicalTrials.gov Identifier: NCT02474667, "Reduce the Severity of DGF in Recipients of a Deceased Donor Kidney," (v6 dated Jun. 8, 2017, Published Jun. 8, 2017 and update posted Jun. 9, 2017 at https://clinicaltrials.gov/ct2/history/NCT02474667?V_6=View#StudyPageTop).
ClinicalTrials.gov Identifier: NCT02474667, "Reduce the Severity of DGF in Recipients of a Deceased Donor Kidney," (v7 dated Aug. 17, 2017, Published Aug. 17, 2017 and update posted Aug. 22, 2017 at https://clinicaltrials.gov/ct2/history/NCT02474667?V_7=View#StudyPageTop).
ClinicalTrials.gov Identifier: NCT02474667, "Reduce the Severity of DGF in Recipients of a Deceased Donor Kidney," (v8 dated Jul. 30, 2019, Published Jul. 30, 2019 and update posted Aug. 1, 2019 at https://clinicaltrials.gov/ct2/history/NCT02474667?V_8=View#StudyPageTop).
ClinicalTrials.gov Identifier: NCT02474667, "Reduce the Severity of DGF in Recipients of a Deceased Donor Kidney," (v9 dated Dec. 26, 2019, Published Dec. 26, 2019 and update posted Dec. 30, 2019 at https://clinicaltrials.gov/ct2/history/NCT02474667?V_9=View#StudyPageTop).
ClinicalTrials.gov Identifier: NCT02771509, "Study to Prevent Acute Kidney Injury After Cardiac Surgery Involving Cardiopulmonary Bypass," (v1 dated May 11, 2016, Published May 11, 2016, and update posted May 13, 2016 at https://clinicaltrials.gov/ct2/history/NCT02771509?V_1=View#StudyPageTop).
ClinicalTrials.gov Identifier: NCT02771509, "Study to Prevent Acute Kidney Injury After Cardiac Surgery Involving Cardiopulmonary Bypass," (v2 dated Jun. 1, 2016, Published Jun. 1, 2016, and update posted Jun. 2, 2016 at https://clinicaltrials.gov/ct2/history/NCT02771509?V_2=View#StudyPageTop).
ClinicalTrials.gov Identifier: NCT02771509, "Study to Prevent Acute Kidney Injury After Cardiac Surgery Involving Cardiopulmonary Bypass," (v3 dated Jan. 17, 2017, Published Jan. 17, 2017, and update posted Jan. 19, 2017 at https://clinicaltrials.gov/ct2/history/NCT02771509?V_3=View#StudyPageTop).
ClinicalTrials.gov Identifier: NCT02771509, "Study to Prevent Acute Kidney Injury After Cardiac Surgery Involving Cardiopulmonary Bypass," (v4 dated Jun. 8, 2017, Published Jun. 8, 2017, and update posted Jun. 9, 2017 at https://clinicaltrials.gov/ct2/history/NCT02771509?V_4=View#StudyPageTop).
ClinicalTrials.gov Identifier: NCT02771509, "Study to Prevent Acute Kidney Injury After Cardiac Surgery Involving Cardiopulmonary Bypass," (v5 dated Jul. 30, 2019, Published Jul. 30, 2019, and update posted Aug. 1, 2019 at https://clinicaltrials.gov/ct2/history/NCT02771509?V_5=View#StudyPageTop).
ClinicalTrials.gov Identifier: NCT02771509, "Study to Prevent Acute Kidney Injury After Cardiac Surgery Involving Cardiopulmonary Bypass," (v6 dated Dec. 26, 2019, Published Dec. 26, 2019, and update posted Dec. 30, 2019 at https://clinicaltrials.gov/ct2/history/NCT02771509?V_6=View#StudyPageTop).
ClinicalTrials.gov Identifier: NCT02771509, "Study to Prevent Acute Kidney Injury After Cardiac Surgery Involving Cardiopulmonary Bypass," (v7 dated Jan. 22, 2020, Published Jan. 22, 2020, and update posted Jan. 27, 2020 at https://clinicaltrials.gov/ct2/history/NCT02771509?V_7=View#StudyPageTop).
ClinicalTrials.gov Identifier: NCT02771509, "Study to Prevent Acute Kidney Injury After Cardiac Surgery Involving Cardiopulmonary Bypass," (v8 dated Feb. 7, 2020, Published Feb. 7, 2020, and update posted Feb. 10, 2020 at https://clinicaltrials.gov/ct2/history/NCT02771509?V_8=View#StudyPageTop).
ClinicalTrials.gov Identifier: NCT02771509, "Study to Prevent Acute Kidney Injury After Cardiac Surgery Involving Cardiopulmonary Bypass," (v9 dated May 18, 2020, Published May 18, 2020, and update posted May 19, 2020 at https://clinicaltrials.gov/ct2/history/NCT02771509?V_9=View#StudyPageTop).
ClinicalTrials.gov Identifier: NCT04459676, "Study to Assess Efficacy and Safety Relative to Standard of Care in Patients With COVID-19 Pneumonia," (v1 dated Jul. 3, 2020, Published Jul. 3, 2020, and update posted Jul. 7, 2020 at https://clinicaltrials.gov/ct2/history/NCT04459676?V_1=View#StudyPageTop).
ClinicalTrials.gov Identifier: NCT04459676, "Study to Assess Efficacy and Safety Relative to Standard of Care in Patients With COVID-19 Pneumonia," (v2 dated Jul. 16, 2020, Published Jul. 16, 2020, and update posted Jul. 17, 2020 at https://clinicaltrials.gov/ct2/history/NCT04459676?V_2=View#StudyPageTop).
ClinicalTrials.gov Identifier: NCT04459676, "Study to Assess Efficacy and Safety Relative to Standard of Care in Patients With COVID-19 Pneumonia," (v3 dated Jul. 20, 2020, Published Jul. 20, 2020, and update posted Jul. 22, 2020 at https://clinicaltrials.gov/ct2/history/NCT04459676?V_3=View#StudyPageTop).
Cooper, M. et al., Potential Cost-savings Associated with ANG-3777 for the Treatment of Delayed Graft Function in Kidney Transplantation, presented virtually online at the American Transplant Congress on May 30-Jun. 1, 2020.
Dohi, M. et al., Hepatocyte Growth Factor Attenuates Collagen Accumulation in a Murine Model of Pulmonary Fibrosis, American Journal of Respiratory and Critical Care Medicine, 162:2302-2307 (2000).
Eldin, S.M. et al., Reactions with Cyanothioacetamide Derivatives: Synthesis and Reactions of Some Pyridine and Annelated Pyridine Derivatives, Egyptian Journal of Pharmaceutical Sciences, 34(4-6):805-815 (1993).
Elghandour, A. et al., A Facile Synthesis of Pyrazolo [1, 5-a]pyridine Derivatives: Reaction of Cinnamonitriles with 5-Amino-4-cyano-3-cyanomethlypyrazole, Journal für Praktische Chemie, 330(4):657-660 (1988).
Franquesa, M. et al., Direct electrotransfer of hHGF gene into kidney ameliorates ischemic acute renal failure, Gene Therapy, 12:1551-1558 (2005).
Fujimoto, J., Hepatology: Microcirculation and Pathogenesis of Alcoholic Liver Injury, Journal of Gastroenterology and Hepatology, 15:33-36 (2000).
Herrero-Fresneda, I. et al., HGF gene therapy attenuates renal allograft scarring by preventing the profibrotic inflammatory-induced mechanisms, Kidney International, 70:265-274 (2006).
Hwang, T.H. et al., A single administration of adenoviral-mediated HGF cDNA permits survival of mice from acute hepatic failure, Life Sciences, 72:851-861, (2003).
International Search Report for PCT/US2003/040917, 6 pages (dated Sep. 22, 2004).
International Search Report for PCT/US2008/011990, 3 pages (dated Jun. 25, 2009).
International Search Report for PCT/US2009/004014, 4 pages (dated Mar. 3, 2010).
Jin, H. et al., Early Treatment with Hepatocyte Growth Factor Improves Cardiac Function in Experimental Heart Failure Induced by Myocardial Infarction, Journal of Pharmacology and Experimental Therapeutics, 304(2):654-660 (2003).
Kaspar, C.D.W. et al., A Review of Pediatric Chronic Kidney Disease, Blood Purif., 41: 211-214 (2016).
King, K. L. et al., Impact of Delayed Graft Function (DGF) on Length of Stay after a Deceased Donor Kidney Transplant, presented at the American Society of Nephrology Annual Meeting in Washington, D.C., Nov. 5-10, 2019.
Lopez-Talavera, J.C. et al., Hepatocyte growth factor gene therapy for pancreatic islets in diabetes: reducing the minimal islet transplant mass required in a glucocorticoid-free rat model of allogeneic portal vein islet transplantation, Division of Endocrinology, 145(2):467-474 (2004).

(56) References Cited

OTHER PUBLICATIONS

Marigny, K. et al., Particular cutaneous side effects with etoposide-containing courses: is VP16 or etoposide phosphate responsible?, Cancer Chemotherapy and Pharmacology, 55:244-250 (2005).
Mathew, B. et al., Synthesis, Preclinical Evaluation and Antidepressant Activity of 5-Substituted Phenyl-3-(Thiophen-2-yl)-4,5-Dihydro-1H-Pyrazole-1-Carbothioamides, EXCLI Journal, 13:437-445 (2014).
Matsuno, Y. et al., Hepatocyte growth factor gene transfer into the liver via the portal vein using electroporation attenuates rat liver cirrhosis, Gene Therapy, 10:1559-1566 (2003).
Mayne, T. et al., Incremental Costs of Delayed Graft Function (DGF) In Commercially Insured Kidney Transplant Patients Under 65, presented virtually online at the American Transplant Congress on May 30-Jun. 1, 2020.
Mayne, T. J. et al., Delayed Graft Function (DGF) in Kidney Transplantation Patients: An Analysis of Disease Burden, presented at the American Society of Nephrology Annual Meeting in Washington, D.C., Nov. 5-10, 2019.
Mohan, S. et al., The Evolution of Renal Graft Failure Risk: The Power of the Proximal, presented virtually online at the American Transplant Congress on May 30-Jun. 1, 2020.
Morishita, R. et al., Safety evaluation of clinical gene therapy using hepatocyte growth factor to treat peripheral arterial disease, Hypertension, 44:203-209 (2004).
Morishita, R. et al., Therapeutic angiogenesis using hepatocyte growth factor (HGF), Current Gene Therapy, 4:199-206 (2004).
Nakagami, H. et al., Hepatocyte growth factor prevents endothelial cell death through inhibition of bax translocation from cytosol to mitochondrial membrane, Diabetes, 51:2604-2611 (2002).
Nakamura, T. et al., Myocardial protection from ischemia/reperfusion injury by endogenous and exogenous HGF, The Journal of Clinical Investigation, 106(12):1511-1519 (2000).
Narayan, P. and Goldberg, I. D., ANG-3777, a Hepatic Growth Factor Mimetic, Attenuates Mercuric Chloride-Induced Renal Dysfunction and Mortality in Rats, presented virtually online at the American Transplant Congress on May 30-Jun. 1, 2020.
Narayan, P. et al., ANG-3777 Treatment Attenuates Ischemia-Reperfusion-Induced Renal Injury in Rat and Dog Models, presented virtually online at the American Transplant Congress on May 30-Jun. 1, 2020.
Narayan, P. et al., Late intervention with the small molecule BB3 mitigates postischemic kidney Injury, Am. J. Physiol. Renal. Physiol., 311: F352-F361 (2016).
Numata, M. et al., Hepatocyte Growth Factor Facilitates the Repair of Large Colonic Ulcers in 2,4,6-Trinitrobenzene Sulfonic Acid-Induced Colitis in Rats, Inflammatory Bowel Diseases, 11(6):551-558 (2005).
Oe, S. et al., Continuous intravenous infusion of deleted form of hepatocyte growth factor attenuates hepatic ischemia-reperfusion injury in rats, Journal of Hepatology, 34:832-839 (2001).
Ono, I. et al., Local administration of hepatocyte growth factor gene enhances the regeneration of dermis in acute incisional wounds, Journal of Surgical Research, 120:47-55 (2004).
Paka, L. and Goldberg, I. D., In Vivo Phosphorylation of c-MET receptor by ANG-3777, a hepatocyte growth factor mimetic, presented virtually online at the American Transplant Congress on May 30-Jun. 1, 2020.
Paka, L. and Goldberg, I. D., The Effect of ANG-3777 on Hepatocyte Growth Factor Receptor, c-MET Signaling, presented virtually online at the American Transplant Congress on May 30-Jun. 1, 2020.
Partial European Search Report for EP10011181.4, 7 pages (dated Dec. 8, 2010).
Patani, G.A. and Lavoie, E.L., Biosterism: a rational approach in drug design, Chemical Review, 93:3147-3176 (1996).
Perevalov, V.P. et al., Spectroscopic features of isomeric trans-styrylpyrazoles, Khimiya Geterotsiklicheskikh Soedinenii, 8:1061-1064 (1990).

Powell, R.J. et al., Therapeutic angiogenesis for critical limb ischemia: design of the hepatocyte growth factor therapeutic angiogenesis clinical trial, Vascular Medicine, 9:193-198 (2004).
Rahmoune, H. et al., Hepatocyte growth factor/scatter factor has distinct classes of binding site in heparan sulfate from mammary cells, Biochemistry, 37:6003-6008 (1998).
Rateb, L. et al., Reactions of Hydroxymethylene Ketones. Part II, Other Routes for the Preparation of Isoxazoles and Pyrazoles, Journal of the Chemical Society, 17:2137-2139 (1968).
Schneider, M. et al. Facile Synthesis of Cyclopropyl Alkadienes, Angewandte Chemie, 91(2):231-234 (1979).
Schvartsberg, M.S. et al., Acetylenic Derivatives of Heterocycles. Transformations of 3-ethynylpyrazole, Khimiya Geterotsiklicheskikh Soedinenii, 4(4):695-697 (1968). [Russian].
Shimamura, M. et al., Novel Therapeutic Strategy to Treat Brain Ischemia: Overexpression of Hepatocyte Growth Factor Gene Reduced Ischemic Injury Without Cerebral Edema in Rat Model, Circulation: Journal of the American Heart Association, 109:424-431 (2004).
Sottofatori, E. et al., Synthesis of New Heterocyclic Derivatives of Retinoids, Journal of Heterocyclic Chemistry, 35(6):1377-1380, (1998).
Strickley, R.G., Solubilizing Excipients in Oral and Injectable Formulations, Pharmaceutical Research, 21(2):201-230 (2004).
Subramaniam, M.A. et al., Nonlinear Optic Properties of Heterocyclic Compounds Hyperpolarizability-structure Correlation, Ferroelectrics and Related Materials, 122(1-4):229-238 (1991).
Tashiro, H. et al., Hepatocyte growth factor prevents chronic allograft dysfunction in liver-transplanted rats, Transplantation: The Official Journal of the Transplantation Society, 76:761-765 (2003).
Tejwani, R.W. et al., Study of Phase Behavior of Poly(ethylene glycol)-Polysorbate 80 and Poly(ethylene glycol)-Polysorbate 80-Water Mixtures, Journal of Pharmaceutical Sciences, 89(7):946-950 (2000).
Tsuruta, H. et al., β-(2,4,6-Cycloheptatrien-1-yl) ethylcarbene. The Synthesis of 9-Substituted bicyclo[4.2.1]nona-2,4,7-trienes and 9-Substituted Barbaralanes, Bulletin of the Chemical Society of Japan, 45:2822-2828 (1972).
Tsuruta, H. et al., Isolation of a Potential Intermediate Leading to 9-Phenylbicyclo[4.2.1]nona-2,4,7-triene in the Thermal Decomposition of α-phenyl-α-tropylacetoaldehyde Tosylhydrazone, Journal of American Chemical Society, 90(25):7167-7168 (1968).
Tsuzuki, N. et al., Hepatocyte growth factor reduces infarct volume after transient focal cerebral ischemis in rats, Acta Neurochirurgica: The European Journal of Neurosurgery, 76:311-316 (2000).
Ueki, T. et al., Hepatocyte growth factor gene therapy of liver cirrhosis in rats, Nature Medicine, 5(2):226-230 (1999).
Watanabe, M. et al., Hepatocyte growth factor gene transfer to alveolar septa for effective suppression of lung fibrosis, Molecular Therapy, 12(1):58-67 (2005).
Yang, J. and Liu, Y., Delayed administration of hepatocyte growth factor reduces renal fibrosis in obstructive nephropathy, American Journal of Physiology: Renal Physiology, 284:F349-F357 (2003).
Yang, J. et al., Continuous AMD3100 Treatment Worsens Renal Fibrosis through Regulation of Bone Marrow Derived Pro-Angiogenic Cells Homing and T-Cell-Related Inflammation, PLOS One, 1-16 (2016).
Yoshida, S. et al., Recombinant hepatocyte growth factor accelerates cutaneous wound healing in a diabetic mouse model, Growth Factors, 22(2):111-119 (2004).
Zhou, Y.J. et al., Hepatocyte growth factor protects human endothelial cells against advanced glycation end products-induced apoptosis, Biochemical and Biophysical Research Communications, 344:658-666 (2006).
Press Release, Angion Biomedica and Sinovant Sciences Enter into Collaboration and License Agreement to Develop BB3 in Greater China, Nov. 12, 2018, accessed on Oct. 7, 2020.
Ayad, S. et al., A Multicenter, Prospective, Randomized, Double-Blind, Placebo Controlled, Phase 2 Study to Assess the Safety and Efficacy of ANG 3777 in Patients Developing Acute Kidney Injury after Cardiac Surgery, presented at the 25th International Conference on Advances in Critical Care Nephrology, AKI & CRRT, Feb. 24-27, 2020.

(56) References Cited

OTHER PUBLICATIONS

Bromberg, J. et al., [Abstract] ANG-3777 Improves Outcomes in Patients with Delayed Graft Function: A Randomized, Double-Blind, Placebo-Controlled Phase 2 Trial with 12-Month Follow-Up, J. Am. Soc. Nephrol. 30: (2019).
Bromberg, J. et al., [Abstract] BB3, a Hepatocyte Growth Factor-Like Small Molecule, Improves Outcome in Kidney Transplant Recipients with Delayed Graft Function, J. Am. Soc. Nephrol., 26 (2015).
Bromberg, J. et al., [Manuscript] Renal Function Improvement Following ANG-3777 Treatment in Patients at High Risk for Delayed Graft Function After Kidney Transplantation (2020).
Bromberg, J. et al., ANG-3777, a Hepatocyte Growth Factor Mimetic, Significantly Improves Outcomes in Patients with Delayed Graft Function: Results from a Randomized Double-blind Placebo Controlled Phase 2 Trial with 12-month Follow-up, presented at 2020 American Transplant Congress on May 30, 2020.
Cai, W. [Abstract] Phase I Study Of BB3 In Dialysis Patients, awarded Jan. 19, 2009.
Cai, W., [Abstract] A Pilot Clinical Study in Acute STEMI, awarded Aug. 28, 2010.
Cai, W., [Abstract] A Pilot Clinical Study in Acute STEMI, awarded Aug. 5, 2011.
Cai, W., [Abstract] Hepatic Growth Factor Mimetic For Liver Fibrosis, awarded Jul. 8, 2004.
Cai, W., [Abstract] Hepatic Growth Factor Mimetic For Liver Fibrosis, awarded Jun. 24, 2005.
Cai, W., [Abstract] Kidney Preservation For Transplantation, awarded Jun. 11, 2007.
Cai, W., [Abstract] Phase I Clinical Study Using An Antifibrotic Drug, awarded Feb. 18, 2011.
Cai, W., [Abstract] Phase I Clinical Study Using An Antifibrotic Drug, awarded Apr. 29, 2010.
Cai, W., [Abstract] Phase I Clinical Trial For BB3, awarded Apr. 7, 2009.
Cai, W., [Abstract] Phase I Clinical Trial For BB3, awarded Jan. 15, 2008.
Cai, W., [Abstract] Pilot Clinical Study In Renal Transplantation, awarded Aug. 7, 2009.
Cai, W., [Abstract] Pilot Clinical Study In Renal Transplantation, awarded Sep. 12, 2010.
Cai, W., [Abstract] Refanalin For Liver Transplantation, awarded Aug. 23, 2004.
Cai, W., [Abstract] Refanalin For Liver Transplantation, awarded Aug. 29, 2005.
Cai, W., [Abstract] Refanalin For Lung Preservation And Transplantation, awarded Apr. 30, 2007.
Cai, W., [Abstract] Refanalin For Lung Preservation And Transplantation, awarded Sep. 13, 2008.
Cai, W., [Abstract] Safety And PK Study In Hepatic Impairment Patients, awarded Aug. 31, 2010.
Cai, W., [Abstract] Safety And PK Study In Hepatic Impairment Patients, awarded Sep. 28, 2009.
Cai, W., [Abstract] Unique Clinical Study On DGF Using Paired Kidneys, awarded Mar. 17, 2011.
Cai, W., [Abstract] Unique Clinical Study On DGF Using Paired Kidneys, awarded Mar. 28, 2012.
Cooper, M. et al., [Abstract C-224] Potential Cost-Savings Associated with ANG-3777 for the Treatment of Delayed Graft Function in Kidney Transplantation, Am. J. Transplant. 2020; 20 (suppl 3).
Mento, P. F., [Abstract] Renal Injury Prevention By SF/HGF-Like Small Molecules, awarded Jul. 29, 2002.
Narayan, P., [Abstract] Kidney Preservation For Transplantation, awarded Apr. 25, 2005.
Narayan, P., [Abstract] Kidney Preservation For Transplantation, awarded Apr. 9, 2004.
Narayan, P., [Abstract] Kidney Preservation For Transplantation, awarded May 26, 2006.
Narayan, P. and Goldberg, I. D., [Abstract] D-311-ANG-3777, A Hepatic Growth Factor Mimetic, Attenuates Mercuric Chloride-Induced Renal Dysfunction and Mortality in Rats, Am. J. Transplant. 2020; 20 (suppl 3).
Narayan, P. et al., [Abstract] C-356-ANG-3777 Treatment Attenuates Ischemia-Reperfusion-Induced Renal Injury in Rat and Dog Models, Am. J. Transplant. 2020; 20 (suppl 3).
Narayan, P. et al., [Abstract] Therapeutic Effects of BB3, a Small Molecule Hepatocyte Growth Factor Mimetic, in Kidney Reperfusion Injury, J. Am. Soc. Nephrol., 26: (2015).
Narayan, P. et al., Therapeutic Effects of BB3, a Small Molecule Hepatocyte Growth Factor Mimetic, in Kidney Reperfusion Injury presented at American Society of Nephrology Kidney Week, on Nov. 3-8, 2015.
Narayan, P., [Abstract] Novel Small Molecule Therapeutic For Spinal Cord Injury, awarded Apr. 2, 2008.
Narayan, P., [Abstract] Novel Small Molecule Therapeutic For Spinal Cord Injury, awarded Aug. 21, 2007.
Narayan, P., [Abstract] Protection From Stroke By SF/HGF-Like Small Molecule, awarded Jun. 20, 2004.
Narayan, P., [Abstract] Refanalin For Lung Preservation And Transplantation, awarded Aug. 31, 2009.
Narayan, P., [Abstract] Small Molecule Therapeutics For Myocardial Ischemia, awarded Aug. 7, 2007.
Narayan, P., [Abstract] Small Molecule Therapeutics For Myocardial Ischemia, awarded Sep. 13, 2006.
Narayan, P., [Abstract] Small Molecule Therapeutics For Myocardial Ischemia, awarded Apr. 29, 2005.
Narayan, P., [Abstract] Small Molecule Therapeutics For Renal Disease, awarded Feb. 16, 2009.
Narayan, P., [Abstract] Small Molecule Therapeutics For Renal Disease, awarded Feb. 24, 2010.
Narayan. P., [Abstract] Small Molecule Therapeutics For Renal Disease, awarded Jul. 10, 2007.
Oehlen, B. J. W. M., [Abstract] Therapeutic Potential Of A Small Molecule Compound For Emphysema, awarded Jul. 10, 2009.
Oehlen, B. J. W. M., [Abstract] Therapeutic Potential Of A Small Molecule Compound For Emphysema, awarded Jul. 2, 2010.
Oehlen, B. J. W. M., [Abstract] Therapeutic Potential Of A Small Molecule Compound For Emphysema, awarded May 9, 2008.
Paka, L. and Goldberg, I. D., [Abstract C-360] In Vivo Phosphorylation of C-MET by ANG-3777, A Hepatocyte Growth Factor Mimetic, Am. J. Transplant. 2020; 20 (suppl 3).
Paka, L. and Goldberg, I. D., [Abstract] The Effect of ANG-3777 on Hepatocyte Growth Factor Receptor C-MET Signaling, Am. J. Transplant. 2020; 20 (suppl 3).
Paka, L., [Abstract] A Therapeutic For Radiation Induced Lung Injury, awarded May 15, 2014.
Paka, L., [Abstract] Anti-Fibrotic Therapy For Pulmonary Fibrosis, awarded Aug. 2, 2007.
Paka, L., [Abstract] Anti-Fibrotic Therapy For Pulmonary Fibrosis, awarded Sep. 14, 2006.
Paka, L., [Abstract] Therapeutic Potential of Refanalin In Pulmonary Fibrosis, awarded Sep. 20, 2004.
Press Release, Angion Announces Publication of ANG-3777 Phase 2 Results in the Scientific Journal—Transplantation, May 5, 2020, retrieved from <<https://angion.com/angion-announces-publication-of-ang-3777-phase-2-results-in-the-scientific-journal-transplantation/>>, accessed on Aug. 13, 2020.
Press Release, Angion Biomedica to Present Clinical and Preclinical Data at the Upcoming American Society of Nephrology Conference in San Diego, Nov. 2, 2015.
Press Release, Angion Presents Positive Long-term Data from Phase 2 Clinical Trial of ANG-3777 in Delayed Graft Function at the American Society of Nephrology Kidney Week 2019, Nov. 7, 2019, retrieved online from <<https://angion.com/angion-presents-positive-long-term-data-from-phase-2-clinical-trial-of-ang-3777-in-delayed-graft-function-at-the-american-society-of-nephrology-kidney-week-2019/>>, accessed on Sep. 2, 2020.
Press Release, Angion to Present Late-Breaking Data on ANG-3777 in Delayed Graft Function at the American Society of Nephrology Kidney Week 2019, Oct. 14, 2019, retrieved from <<https://angion.com/angion-to-present-late-breaking-data-on-ang-3777-in-delayed-

(56) References Cited

OTHER PUBLICATIONS graft-function-at-the-american-society-of-nephrology-kidney-week-2019/>>, accessed on Aug. 13, 2020.
Smith, D. E., [Abstract] Novel Neuroprotective/Restorative Therapy For Ischemic Stroke, awarded Apr. 23, 2010.
Smith, D. E., [Abstract] Novel Neuroprotective/Restorative Therapy For Ischemic Stroke, awarded Jul. 18, 2009.
Smith, D. E., [Abstract] Novel Neuroprotective/Restorative Therapy For Ischemic Stroke, awarded Jul. 31, 2012.
Smith, D. E., [Abstract] Novel Therapeutic For Amyotrophic Lateral Sclerosis (ALS), awarded Sep. 1, 2008.
Smith, D. E., [Abstract] Novel Therapeutic For Amyotrophic Lateral Sclerosis, awarded Aug. 3, 2010.
Smith, D. E., [Abstract] Novel Therapeutic For Amyotrophic Lateral Sclerosis, awarded Sep. 30, 2009.
Smith, D. E., [Abstract] Novel Therapeutic For Duchenne Muscular Dystrophy (DMD), awarded Mar. 16, 2009.
Smith, D. E., [Abstract] Novel Therapy For Amyotrophic Lateral Sclerosis, awarded Apr. 13, 2010.
Yuzhakov, A., [Abstract] Novel Small Molecule Therapeutic For Spinal Cord Injury, awarded Jul. 12, 2006.

\* cited by examiner

SOLID FORMS OF (E)-3-[2-(2-THIENYL)VINYL]-1H-PYRAZOLE

RELATED APPLICATIONS

The present application is a continuation of International Patent Application No. PCT/US20/27710, filed Apr. 10, 2020, which claims priority to U.S. Provisional Patent Application No. 62/832,519, filed Apr. 11, 2019, the entire contents of which are hereby incorporated by reference.

BACKGROUND OF THE INVENTION

Scatter factor (SF; also known as hepatocyte growth factor (HGF), and hereinafter referred to and abbreviated as HGF/SF) is a pleiotropic growth factor that stimulates cell growth, cell motility, morphogenesis and angiogenesis. HGF/SF is produced as an inactive monomer (~100 kadam) which is proteolytically converted to its active form. Active HGF/SF is a heparin-binding heterodimeric protein composed of a 62 kDa a chain and a 34 kDa 0 chain. HGF/SF is a potent mitogen for parenchymal liver, epithelial and endothelial cells (Matsumoto, K, and Nakamura, T., 1997, Hepatocyte growth factor (HGF) as a tissue organizer for organogenesis and regeneration. Biochem. Biophys. Res. Commun. 239, 639-44; Boros, P. and Miller, C. M., 1995, Hepatocyte growth factor: a multifunctional cytokine. Lancet 345, 293-5). It stimulates the growth of endothelial cells and also acts as a survival factor against endothelial cell death (Morishita, R, Nakamura, S, Nakamura, Y, Aoki, M, Moriguchi, A, Kida, I, Yo, Y, Matsumoto, K, Nakamura, T, Higaki, J, Ogihara, T, 1997, Potential role of an endothelium-specific growth factor, hepatocyte growth factor, on endothelial damage in diabetes. Diabetes 46:138-42). HGF/SF synthesized and secreted by vascular smooth muscle cells stimulates endothelial cells to proliferate, migrate and differentiate into capillary-like tubes in vitro (Grant, D. S, Kleinman, H. K., Goldberg, I. D., Bhargava, M. M., Nickoloff, B. J., Kinsella, J. L., Polverini, P., Rosen, E. M., 1993, Scatter factor induces blood vessel formation in vivo. Proc. Natl. Acad. Sci. USA 90:1937-41; Morishita, R., Nakamura, S., Hayashi, S., Taniyama, Y., Moriguchi, A., Nagano, T., Taiji, M., Noguchi, H., Takeshita, S., Matsumoto, K., Nakamura, T., Higaki, J., Ogihara, T., 1999, Therapeutic angiogenesis induced by human recombinant hepatocyte growth factor in rabbit hind limb ischemia model as cytokine supplement therapy. Hypertension 33:1379-84). HGF/SF-containing implants in mouse subcutaneous tissue and rat cornea induce growth of new blood vessels from surrounding tissue. HGF/SF protein is expressed at sites of neovascularization including in tumors (Jeffers, M., Rong, S., Woude, G. F., 1996, Hepatocyte growth factor/scatter factor-Met signaling in tumorigenicity and invasion/metastasis. J. Mol. Med. 74:505-13; Moriyama, T., Kataoka, H., Koono, M., Wakisaka, S., 1999, Expression of hepatocyte growth factor/scatter factor and its receptor c-met in brain tumors: evidence for a role in progression of astrocytic tumors Int. J. Mol. Med. 3:531-6). These findings suggest that HGF/SF plays a significant role in the formation and repair of blood vessels under physiologic and pathologic conditions.

All citations in the present application are incorporated herein by reference in their entireties. The citation of any reference herein should not be construed as an admission that such reference is available as "Prior Art" to the instant application.

SUMMARY

Polymorphs, solvates and salts of various drugs have been described in the literature as imparting novel properties to the drugs. Organic small drug molecules have a tendency to self-assemble into various polymorphic forms depending on the environment that drives the self-assembly. Heat- and solvent-mediated effects can also lead to changes that transform one polymorphic form into another.

Identifying which polymorphic form or forms are the most stable under each condition of interest, and the processes that lead to changes in the polymorphic form, is warranted for design of the drug manufacturing process in order to ensure that a final product is in its preferred polymorphic form. Different polymorphic forms of an active pharmaceutical ingredient (API) can lead to changes in a drug's solubility, dissolution rate, pharmacokinetics, and, ultimately, its bioavailability and efficacy in patients.

Novel solid forms of the present invention, and compositions thereof, are useful in the treatment and/or prevention of conditions or diseases in which HGF/SF activity is desirable. In general, these solid forms, and pharmaceutically acceptable compositions thereof, are useful for treating or lessening the severity of a variety of diseases or disorders as described in detail herein.

DETAILED DESCRIPTION

Figure 1:
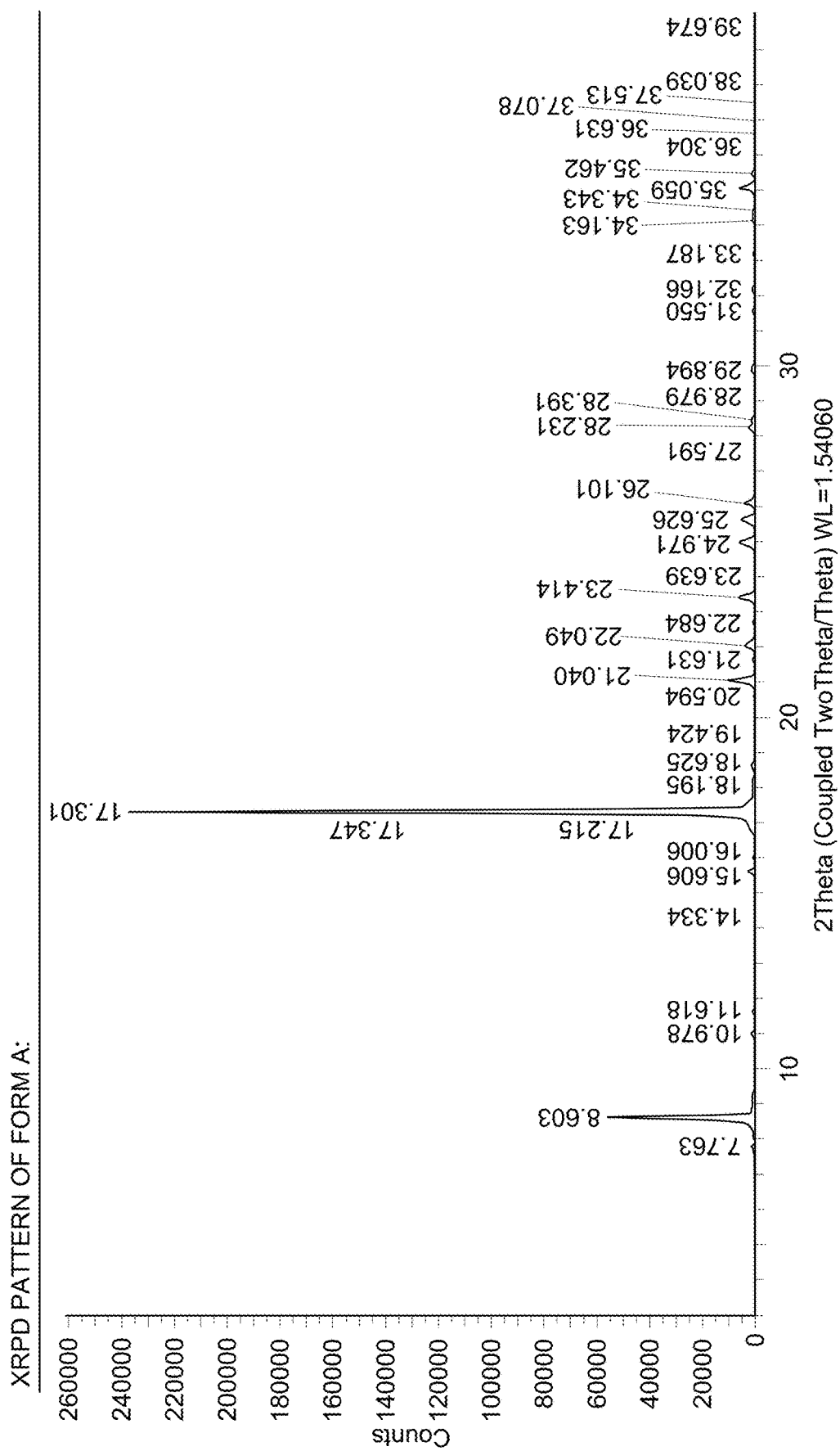
FIG. 1 provides an X-Ray Powder Diffraction (XRPD) pattern of solid Form A.

PCT patent application PCT/US2003/040917, filed Dec. 19, 2003 and published as WO2004/058721 on Jul. 15, 2004, the entirety of which is hereby incorporated by reference, describes certain compounds that act as HGF/SF mimetics. Such compounds include Compound 1:

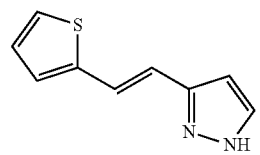

A synthesis of Compound 1, (E)-3-[2-(2-thienyl)vinyl]-1H-pyrazole, is described in detail in Example 7 of WO2004/058721. Those skilled in the art will appreciate that Compound 1 has a structure that can exist in various tautomeric forms, including (E)-3-[2-(2-thienyl)vinyl]-1H-pyrazole and (E)-5-[2-(2-thienyl)vinyl]-1H-pyrazole, or any mixture thereof. Moreover, those skilled in the art, reading the present disclosure will appreciate that, in many embodiments, teachings described herein are not limited to any particular tautomeric form. Accordingly, the structure depicted above for Compound 1 is meant to include all tautomeric forms of Compound 1, including (E)-3-[2-(2-thienyl)vinyl]-1H-pyrazole and (E)-5-[2-(2-thienyl)vinyl]-1H-pyrazole. Compound 1 can also be referred to as (E)-3 (5)-[2-(2-thienyl)vinyl]-1H-pyrazole.

It is desirable to provide a solid form of Compound 1 that, as compared to amorphous Compound 1, imparts characteristics such as improved solubility, stability, storability, ease of purification during manufacture, ease of handling and/or ease of formulation. Accordingly, the present disclosure provides several solid forms of Compound 1.

Solid Forms of Compound 1

Compound 1 can exist in an amorphous solid form or in a crystalline solid form, or in a mixture thereof. Crystalline solid forms can exist in one or more unique forms, which can be solvates, heterosolvates, hydrates, or unsolvated forms. All such forms are contemplated by the present disclosure.

In some embodiments, this disclosure provides one or more polymorphic solid forms of Compound 1. As used herein, the term "polymorph" refers to the ability of a compound to exist in one or more different crystal structures. For example, one or more polymorphs may vary in pharmaceutically relevant physical properties between one form and another, for example solubility, stability, and hygroscopicity.

In some embodiments, the present disclosure provides an anhydrous (i.e., unsolvated) polymorphic form of Compound 1.

In some embodiments, Compound 1 is provided as a solvate or heterosolvate. As used herein, the term "solvate" refers to a solid form with a stoichiometric amount of one or more solvents (e.g., water, ethylene glycol, propylene glycol, etc.) incorporated into the crystal structure. For example, a solvated or heterosolvated polymorph can comprise 0.05, 0.1, 0.2, 0.5, 1.0, 1.5, 2.0, etc. equivalents independently of one or more solvents incorporated into the crystal lattice.

In some embodiments, Compound 1 is provided as a hydrate. As used herein, the term "hydrate" refers to a solid form with a stoichiometric amount of water incorporated into the crystal structure. For example, a hydrated polymorph can comprise 0.05, 0.1, 0.2, 0.5, 1.0, 1.5, 2.0, etc. equivalents of water incorporated into the crystal lattice.

In some embodiments, Compound 1 is provided as a hydrate and/or a solvate or heterosolvate.

In some embodiments, a crystalline solid form of Compound 1 is provided.

In some embodiments, the present disclosure provides a solvate form of Compound 1. In some embodiments, a solvate form of Compound 1 is an ethylene glycol solvate. In some embodiments, a solvate form of Compound 1 is a propylene glycol solvate.

In some embodiments, this disclosure provides a composition comprising a crystalline solid form of Compound 1. In some embodiments, the present disclosure provides a composition comprising a mixture of two or more crystalline solid forms of Compound 1. In some embodiments, the present disclosure provides a composition comprising a mixture of one or more crystalline solid forms of Compound 1 and amorphous Compound 1. In some embodiments, a composition is substantially free of amorphous Compound 1. As used herein, the term "substantially free of amorphous Compound 1" means that a composition contains no significant amount of amorphous Compound 1. In some embodiments, a composition comprises at least about 90% by weight of crystalline Compound 1. In some embodiments, a composition comprises at least about 95% by weight of crystalline Compound 1. In some embodiments, a composition comprises at least about 97%, about 98%, or about 99% by weight of crystalline Compound 1.

Compound 1 can exist in at least three distinct crystalline solid forms, designated herein as Form A, Form C, and Form D.

As used herein, the term "about," when used in reference to a degree 2-theta value refers to the stated value±0.2 degree 2-theta. In some embodiments, "about" refers to the stated value±0.1 degree 2-theta.

Form A

In some embodiments, a crystalline solid form of Compound 1 is Form A. In some embodiments, Form A of Compound 1 is unsolvated (e.g., anhydrous).

In some embodiments, Form A is characterized by one or more peaks in its XRPD pattern selected from those at about 8.64, about 11.04, about 17.34, about 25.06, and about 25.70 degrees 2-theta. In some embodiments, Form A is characterized by two or more peaks in its XRPD pattern selected from those at about 8.64, about 11.04, about 17.34, about 25.06, and about 25.70 degrees 2-theta. In some embodiments, Form A is characterized by three or more peaks in its XRPD pattern selected from those at about 8.64, about 11.04, about 17.34, about 25.06, and about 25.70 degrees 2-theta.

In some embodiments, Form A is characterized by peaks in its XRPD pattern at about 8.64, about 11.04, about 17.34, about 25.06, and about 25.70 degrees 2-theta. In some embodiments, Form A is characterized by peaks in its XRPD pattern at about 8.64, about 11.04, about 17.34, about 25.06, and about 25.70 degrees 2-theta, corresponding to d-spacing of about 10.22, about 8.01, about 5.11, about 3.55, and about 3.46 angstroms.

In some embodiments, Form A is characterized by substantially all of the peaks (degrees 2-theta) in its XRPD pattern, optionally corresponding to d-spacing (angstroms), at about:

| 2θ (°) | d-spacing (Å) |
|---|---|
| 8.64 | 10.27 |
| 11.04 | 8.01 |
| 11.67 | 7.57 |
| 16.06 | 5.51 |

-continued

| 2θ (°) | d-spacing (Å) |
|---|---|
| 17.34 | 5.11 |
| 18.27 | 4.85 |
| 18.69 | 4.74 |
| 19.49 | 4.55 |
| 20.66 | 4.30 |
| 21.09 | 4.21 |
| 21.70 | 4.09 |
| 22.10 | 4.02 |
| 22.76 | 3.90 |
| 23.46 | 3.79 |
| 23.74 | 3.74 |
| 25.06 | 3.55 |
| 25.70 | 3.46 |
| 26.12 | 3.41 |
| 26.32 | 3.38 |
| 27.64 | 3.23 |
| 27.78 | 3.21 |
| 28.31 | 3.15 |
| 28.49 | 3.13 |
| 29.04 | 3.07 |
| 29.95 | 2.98 |
| 31.59 | 2.83 |
| 31.82 | 2.81 |
| 37.25 | 2.77 |
| 33.22 | 2.69 |
| 34.21 | 2.62 |
| 34.42 | 2.60 |
| 35.08 | 2.56 |
| 35.53 | 2.52 |
| 36.33 | 2.47 |
| 36.70 | 2.45 |
| 37.16 | 2.42 |
| 37.65 | 2.39 |
| 39.02 | 2.31 |
| 39.60 | 2.27 |
| 39.81 | 2.26 |

In some embodiments, Form A is characterized by one or more of the following:
(i) an XRPD pattern substantially similar to that depicted in FIG. 17 and/or FIG. 18,
(ii) a TGA pattern substantially similar to that depicted in FIG. 19;
(iii) a DSC pattern substantially similar to that depicted in FIG. 20; and
(iv) a melting point of about 116.42° C.

In some embodiments, Form A is characterized by one or more peaks in its X-ray powder diffraction pattern selected from those at 8.60, 15.61, 17.22, 17.30, 17.35, 21.04, 22.05, 23.41, 24.97, 25.63, 26.10 and 35.06 degrees 2-theta±0.2.

In some embodiments, Form A is characterized by two or more peaks in its X-ray powder diffraction pattern selected from those at 8.60, 15.61, 17.22, 17.30, 17.35, 21.04, 22.05, 23.41, 24.97, 25.63, 26.10 and 35.06 degrees 2-theta±0.2.

In some embodiments, Form A is characterized by three or more peaks in its X-ray powder diffraction pattern selected from those at 8.60, 15.61, 17.22, 17.30, 17.35, 21.04, 22.05, 23.41, 24.97, 25.63, 26.10 and 35.064 degrees 2-theta±0.2.

In some embodiments, Form A is characterized by four or more peaks in its X-ray powder diffraction pattern selected from those at 8.60, 15.61, 17.22, 17.30, 17.35, 21.04, 22.05, 23.41, 24.97, 25.63, 26.10 and 35.06 degrees 2-theta±0.2.

In some embodiments, Form A is characterized by five or more peaks in its X-ray powder diffraction pattern selected from those at 8.60, 15.61, 17.22, 17.30, 17.35, 21.04, 22.05, 23.41, 24.97, 25.63, 26.10 and 35.06 degrees 2-theta±0.2.

In some embodiments, Form A is characterized by six or more peaks in its X-ray powder diffraction pattern selected from those at 8.60, 15.61, 17.22, 17.30, 17.35, 21.04, 22.05, 23.41, 24.97, 25.63, 26.10 and 35.06 degrees 2-theta±0.2.

In some embodiments, Form A is characterized by seven or more peaks in its X-ray powder diffraction pattern selected from those at 8.60, 15.61, 17.22, 17.30, 17.35, 21.04, 22.05, 23.41, 24.97, 25.63, 26.10 and 35.06 degrees 2-theta±0.2.

In some embodiments, Form A is characterized by eight or more peaks in its X-ray powder diffraction pattern selected from those at 8.60, 15.61, 17.22, 17.30, 17.35, 21.04, 22.05, 23.41, 24.97, 25.63, 26.10 and 35.06 degrees 2-theta±0.2.

In some embodiments, Form A is characterized by nine or more peaks in its X-ray powder diffraction pattern selected from those at 8.60, 15.61, 17.22, 17.30, 17.35, 21.04, 22.05, 23.41, 24.97, 25.63, 26.10 and 35.06 degrees 2-theta±0.2.

In some embodiments, Form A is characterized by ten or more peaks in its X-ray powder diffraction pattern selected from those at 8.60, 15.61, 17.22, 17.30, 17.35, 21.04, 22.05, 23.41, 24.97, 25.63, 26.10 and 35.06 degrees 2-theta±0.2.

In some embodiments, Form A is characterized by peaks in its X-ray powder diffraction pattern selected from those at 8.60, 15.61, 17.22, 17.30, 17.35, 21.04, 22.05, 23.41, 24.97, 25.63, 26.10 and 35.06 degrees 2-theta±0.2.

In some embodiments, Form A is characterized by peaks in its X-ray powder diffraction pattern at 15.61 and 17.22 degrees 2-theta±0.2.

In some embodiments, Form A is characterized by peaks in its X-ray powder diffraction pattern at 15.61 and 26.1 degrees 2-theta±0.2.

In some embodiments, Form A is characterized by peaks in its X-ray powder diffraction pattern at 15.61 and 35.06 degrees 2-theta±0.2.

In some embodiments, Form A is characterized by peaks in its X-ray powder diffraction pattern at 17.22 and 26.1 degrees 2-theta±0.2.

In some embodiments, Form A is characterized by peaks in its X-ray powder diffraction pattern at 17.22 and 35.06 degrees 2-theta±0.2.

In some embodiments, Form A is characterized by peaks in its X-ray powder diffraction pattern at 17.22, 26.1, and 35.06 degrees 2-theta±0.2.

In some embodiments, Form A is characterized by peaks in its X-ray powder diffraction pattern at 15.61, 26.1, and 35.06 degrees 2-theta±0.2.

In some embodiments, Form A is characterized by peaks in its X-ray powder diffraction pattern at 15.61, 17.22, and 35.06 degrees 2-theta±0.2.

In some embodiments, Form A is characterized by peaks in its X-ray powder diffraction pattern at 15.61, 17.22, and 26.1 degrees 2-theta±0.2.

In some embodiments, Form A is characterized by peaks in its X-ray powder diffraction pattern at 15.61, 17.22, 26.1, and 35.06 degrees 2-theta±0.2.

In some embodiments, Form A is characterized by peaks in its X-ray powder diffraction pattern at 17.30 and 17.35 degrees 2-theta±0.2.

In some embodiments, Form A is characterized by peaks in its X-ray powder diffraction pattern at 8.60, 17.30, and 17.35 degrees 2-theta±0.2.

In some embodiments, Form A is characterized by peaks in its X-ray powder diffraction pattern at 8.60, 17.22, 17.30 and 17.35 degrees 2-theta±0.2.

In some embodiments, Form A is characterized by peaks in its X-ray powder diffraction pattern at 8.60, 17.22, 17.30, 17.35 and 21.04 degrees 2-theta±0.2.

In some embodiments, Form A is characterized by peaks in its X-ray powder diffraction pattern at 8.60, 17.22, 17.30, 17.35, 21.04 and 23.41 degrees 2-theta±0.2.

In some embodiments, Form A is characterized by an XRPD pattern with substantially the same peaks (degrees 2-theta±0.2), optionally corresponding to d-spacing (angstroms±0.2) and/or relative intensity (%) of:

| Degrees 2-Theta ± 0.2 | d-spacing (Å) | Relative intensity (%) |
|---|---|---|
| 8.60 | 10.27 | 23.1 |
| 15.61 | 5.67 | 1.0 |
| 17.22 | 5.15 | 19.3 |
| 17.30 | 5.12 | 100 |
| 17.35 | 5.11 | 58.2 |
| 21.04 | 4.22 | 4.4 |
| 22.05 | 4.03 | 1.5 |
| 23.41 | 3.80 | 2.6 |
| 24.97 | 3.56 | 2.4 |
| 25.63 | 3.47 | 2.1 |
| 26.10 | 3.41 | 1.8 |
| 35.06 | 2.56 | 2.3 |

In some embodiments, Form A is characterized by one or more peaks in its X-ray powder diffraction pattern selected from those at 8.60, 17.22, 17.30, 17.35, 21.04, 22.05, 23.41, 24.97, 25.63, 26.10 and 35.06 degrees 2-theta±0.2.

In some embodiments, Form A is characterized by two or more peaks in its X-ray powder diffraction pattern selected from those at 8.60, 17.22, 17.30, 17.35, 21.04, 22.05, 23.41, 24.97, 25.63, 26.10 and 35.06 degrees 2-theta±0.2.

In some embodiments, Form A is characterized by three or more peaks in its X-ray powder diffraction pattern selected from those at 8.60, 17.22, 17.30, 17.35, 21.04, 22.05, 23.41, 24.97, 25.63, 26.10 and 35.064 degrees 2-theta±0.2.

In some embodiments, Form A is characterized by four or more peaks in its X-ray powder diffraction pattern selected from those at 8.60, 17.22, 17.30, 17.35, 21.04, 22.05, 23.41, 24.97, 25.63, 26.10 and 35.06 degrees 2-theta±0.2.

In some embodiments, Form A is characterized by five or more peaks in its X-ray powder diffraction pattern selected from those at 8.60, 17.22, 17.30, 17.35, 21.04, 22.05, 23.41, 24.97, 25.63, 26.10 and 35.06 degrees 2-theta±0.2.

In some embodiments, Form A is characterized by six or more peaks in its X-ray powder diffraction pattern selected from those at 8.60, 17.22, 17.30, 17.35, 21.04, 22.05, 23.41, 24.97, 25.63, 26.10 and 35.06 degrees 2-theta±0.2.

In some embodiments, Form A is characterized by seven or more peaks in its X-ray powder diffraction pattern selected from those at 8.60, 17.22, 17.30, 17.35, 21.04, 22.05, 23.41, 24.97, 25.63, 26.10 and 35.06 degrees 2-theta±0.2.

In some embodiments, Form A is characterized by eight or more peaks in its X-ray powder diffraction pattern selected from those at 8.60, 17.22, 17.30, 17.35, 21.04, 22.05, 23.41, 24.97, 25.63, 26.10 and 35.06 degrees 2-theta±0.2.

In some embodiments, Form A is characterized by nine or more peaks in its X-ray powder diffraction pattern selected from those at 8.60, 17.22, 17.30, 17.35, 21.04, 22.05, 23.41, 24.97, 25.63, 26.10 and 35.06 degrees 2-theta±0.2.

In some embodiments, Form A is characterized by ten or more peaks in its X-ray powder diffraction pattern selected from those at 8.60, 17.22, 17.30, 17.35, 21.04, 22.05, 23.41, 24.97, 25.63, 26.10 and 35.06 degrees 2-theta±0.2.

In some embodiments, Form A is characterized by peaks in its X-ray powder diffraction pattern selected from those at 8.60, 17.22, 17.30, 17.35, 21.04, 22.05, 23.41, 24.97, 25.63, 26.10 and 35.06 degrees 2-theta±0.2.

In some embodiments, Form A is characterized by an XRPD pattern with substantially the same peaks (degrees 2-theta±0.2), optionally corresponding to d-spacing (angstroms±0.2) and/or relative intensity (%) of:

| Degrees 2-Theta ± 0.2 | d-spacing (Å) | Relative intensity (%) |
|---|---|---|
| 8.60 | 10.27 | 73.1 |
| 17.22 | 5.15 | 19.3 |
| 17.30 | 5.12 | 100 |
| 17.35 | 5.11 | 58.2 |
| 21.04 | 4.22 | 4.4 |
| 22.05 | 4.03 | 1.5 |
| 23.41 | 3.80 | 2.6 |
| 24.97 | 3.56 | 2.4 |
| 25.63 | 3.47 | 2.1 |
| 26.10 | 3.41 | 1.8 |
| 35.06 | 2.56 | 7.3 |

In some embodiments, Form A of Compound 1 has one or more of the following characteristics:
(i) an XRPD pattern substantially similar to that depicted in FIG. 1;
(ii) a DSC pattern substantially similar to that depicted in any one of FIG. 2, FIG. 3, or FIG. 4;
(iii) a TGA pattern substantially similar to that depicted in any one of FIG. 5, FIG. 6, or FIG. 7; and
(iv) a melting point of about 115-120° C.

Form C

In some embodiments, a crystalline solid form of Compound 1 is Form C. In some embodiments, Form C of Compound 1 is a propylene glycol solvate. In some embodiments, Form C of Compound 1 is a propylene glycol solvate, wherein the ratio of Compound 1 to propylene glycol is about 2:1.

In some embodiments, Form C is characterized by one or more peaks in its XRPD pattern selected from those at about 11.88, about 17.50, about 19.08, about 21.28, and about 23.07 degrees 2-theta. In some embodiments, Form C is characterized by two or more peaks in its XRPD pattern selected from those at about 11.88, about 17.50, about 19.08, about 21.28, and about 23.07 degrees 2-theta. In some embodiments, Form C is characterized by three or more peaks in its XRPD pattern selected from those at about 11.88, about 17.50, about 19.08, about 21.28, and about 23.07 degrees 2-theta.

In some embodiments, Form C is characterized by peaks in its XRPD pattern at about 11.88, about 17.50, about 19.08, about 21.28, and about 23.07 degrees 2-theta. In some embodiments, Form C is characterized by peaks in its XRPD pattern at about 11.88, about 17.50, about 19.08, about 21.28, and about 23.07 degrees 2-theta, corresponding to d-spacing of about 7.44, about 5.06, about 4.65, about 4.17, and about 3.85 angstroms.

In some embodiments, Form C is characterized by substantially all of the peaks (degrees 2-theta) in its XRPD pattern, optionally corresponding to d-spacing (angstroms), at about:

| 2θ (°) | d-spacing (Å) |
|---|---|
| 6.20 | 14.24 |
| 11.88 | 7.44 |
| 12.41 | 7.13 |
| 14.79 | 5.99 |
| 15.72 | 5.63 |
| 17.50 | 5.06 |
| 17.78 | 4.98 |
| 19.08 | 4.65 |
| 19.36 | 4.58 |
| 21.28 | 4.17 |
| 21.89 | 4.06 |
| 23.07 | 3.85 |
| 23.69 | 3.75 |
| 23.92 | 3.72 |
| 24.70 | 3.60 |
| 24.90 | 3.57 |
| 25.50 | 3.49 |
| 25.71 | 3.46 |
| 26.28 | 3.39 |
| 27.74 | 3.21 |
| 28.13 | 3.17 |
| 29.10 | 3.07 |
| 29.31 | 3.04 |
| 29.55 | 3.02 |
| 30.51 | 2.93 |
| 31.15 | 2.87 |
| 31.76 | 2.82 |
| 32.93 | 2.72 |
| 33.19 | 2.70 |
| 33.36 | 2.68 |
| 34.63 | 2.59 |
| 35.05 | 2.56 |
| 35.40 | 2.53 |
| 35.90 | 2.50 |
| 36.20 | 2.48 |
| 36.60 | 2.45 |
| 37.57 | 2.39 |
| 37.69 | 2.38 |
| 38.05 | 2.36 |
| 38.54 | 7.33 |
| 38.80 | 2.32 |
| 39.05 | 2.30 |
| 39.46 | 2.28 |
| 39.82 | 2.26 |

In some embodiments, Form C of Compound 1 has one or more of the following characteristics:
(i) an XRPD pattern substantially similar to that depicted in FIG. 22 and/or FIG. 23;
(ii) a TGA pattern substantially similar to that depicted in any one of FIG. 24;
(iii) a DSC pattern substantially similar to that depicted in any one of FIG. 25; and
(iv) a melting point of about 75.22° C.

Form D

In some embodiments, a crystalline solid form of Compound 1 is Form D. In some embodiments, Form D of Compound 1 is an ethylene glycol solvate. In some embodiments, Form D of Compound 1 is an ethylene glycol solvate, wherein the ratio of Compound 1 to ethylene glycol is about 2:1.

In some embodiments, Form D is characterized by one or more peaks in its XRPD pattern selected from those at about 12.28, about 15.10, about 18.06, about 21.58, and about 23.88 degrees 2-theta. In some embodiments, Form D is characterized by two or more peaks in its XRPD pattern selected from those at about 12.28, about 15.10, about 18.06, about 21.58, and about 23.88 degrees 2-theta. In some embodiments, Form D is characterized by three or more peaks in its XRPD pattern selected from those at about 12.28, about 15.10, about 18.06, about 21.58, and about 23.88 degrees 2-theta.

In some embodiments, Form D is characterized by peaks in its XRPD pattern at about 12.28, about 15.10, about 18.06, about 21.58, and about 23.88 degrees 2-theta. In some embodiments, Form D is characterized by peaks in its XRPD pattern at about 12.28, about 15.10, about 18.06, about 21.58, and about 23.88 degrees 2-theta, corresponding to d-spacing of about 7.20, about 5.86, about 4.91, about 4.11, and about 3.72 angstroms.

In some embodiments, Form D is characterized by substantially all of the peaks (degrees 2-theta) in its XRPD pattern, optionally corresponding to d-spacing (angstroms), at about:

| 2θ (°) | d-spacing (Å) |
|---|---|
| 6.19 | 14.28 |
| 12.28 | 7.20 |
| 12.38 | 7.14 |
| 15.10 | 5.86 |
| 15.24 | 5.81 |
| 16.17 | 5.48 |
| 17.60 | 5.03 |
| 18.06 | 4.91 |
| 18.63 | 4.76 |
| 19.11 | 4.64 |
| 19.44 | 4.56 |
| 20.35 | 4.36 |
| 21.58 | 4.11 |
| 21.95 | 4.05 |
| 22.55 | 3.94 |
| 23.88 | 3.72 |
| 24.70 | 3.60 |
| 24.88 | 3.58 |
| 25.57 | 3.48 |
| 25.76 | 3.46 |
| 26.07 | 3.42 |
| 26.33 | 3.38 |
| 26.50 | 3.36 |
| 26.75 | 3.33 |
| 26.99 | 3.30 |
| 27.25 | 3.27 |
| 28.51 | 3.13 |
| 28.72 | 3.11 |
| 29.96 | 2.98 |
| 30.10 | 2.97 |
| 30.26 | 2.95 |
| 30.47 | 2.93 |
| 30.62 | 2.92 |
| 30.75 | 2.90 |
| 31.27 | 2.86 |
| 31.57 | 2.83 |
| 31.83 | 2.81 |
| 31.97 | 2.80 |
| 32.38 | 2.76 |
| 32.67 | 2.74 |
| 33.61 | 2.66 |
| 33.82 | 2.65 |
| 34.84 | 2.57 |
| 35.78 | 2.51 |
| 36.02 | 2.49 |
| 36.36 | 2.47 |
| 36.53 | 2.46 |
| 36.66 | 2.45 |
| 37.10 | 2.42 |
| 37.44 | 2.40 |
| 37.81 | 2.38 |
| 38.38 | 2.34 |
| 38.72 | 2.32 |
| 39.24 | 2.29 |
| 39.78 | 2.26 |

In some embodiments, Form D of Compound 1 has one or more of the following characteristics:
(i) an XRPD pattern substantially similar to that depicted in FIG. 26 and/or FIG. 27;
(ii) a TGA pattern substantially similar to that depicted in any one of FIG. 28;
(iii) a DSC pattern substantially similar to that depicted in any one of FIG. 29; and
(iv) a melting point of about 76.95° C.

Mixtures of Compound 1 Solid Forms

In some embodiments, a composition comprising a mixture of solid forms of Compound 1 is provided. In some such embodiments, a provided composition comprises a mixture of Form A and at least one additional solid form of Compound 1. In some embodiments, a provided composition comprises a mixture of Form A and Form C. In some embodiments, a provided composition comprises a mixture of Form A and Form D.

In some embodiments, this disclosure provides a mixture comprising Forms A and C in a ratio of between about 98:2 and about 95:5. In one embodiment, this invention provides a mixture comprising Forms A and C in a ratio of between about 95:5 and about 90:10. In one embodiment, this disclosure provides a mixture comprising Forms A and C in a ratio of between about 90:10 and about 85:15. In one embodiment, this disclosure provides a mixture comprising Forms A and C in a ratio of between about 85:15 and about 80:20. In one embodiment, this disclosure provides a mixture comprising Forms A and C in a ratio of about 50:50.

In some embodiments, a composition comprising a mixture of Form A and Form C is characterized by one or more peaks in its X-ray powder diffraction pattern selected from those at 8.58, 10.97, 11.81, 14.72, 15.65, 17.32, 17.41, 17.70, 18.61, 19.02, 19.27, 21.20, 22.09, 22.97, 23.60, 24.92, 25.59, 26.20, 27.65, 30.42, 31.07, and 35.33 degrees 2-theta±0.2.

In some embodiments, a composition comprising a mixture of Form A and Form C is characterized by two or more peaks in its X-ray powder diffraction pattern selected from those at 8.58, 10.97, 11.81, 14.72, 15.65, 17.32, 17.41, 17.70, 18.61, 19.02, 19.27, 21.20, 22.09, 22.97, 23.60, 24.92, 25.59, 26.20, 27.65, 30.42, 31.07, and 35.33 degrees 2-theta±0.2.

In some embodiments, a composition comprising a mixture of Form A and Form C is characterized by three or more peaks in its X-ray powder diffraction pattern selected from those at 8.58, 10.97, 11.81, 14.72, 15.65, 17.32, 17.41, 17.70, 18.61, 19.02, 19.27, 21.20, 22.09, 22.97, 23.60, 24.92, 25.59, 26.20, 27.65, 30.42, 31.07, and 35.33 degrees 2-theta±0.2.

In some embodiments, a composition comprising a mixture of Form A and Form C is characterized by four or more peaks in its X-ray powder diffraction pattern selected from those at 8.58, 10.97, 11.81, 14.72, 15.65, 17.32, 17.41, 17.70, 18.61, 19.02, 19.27, 21.20, 22.09, 22.97, 23.60, 24.92, 25.59, 26.20, 27.65, 30.42, 31.07, and 35.33 degrees 2-theta±0.2.

In some embodiments, a composition comprising a mixture of Form A and Form C is characterized by five or more peaks in its X-ray powder diffraction pattern selected from those at 8.58, 10.97, 11.81, 14.72, 15.65, 17.32, 17.41, 17.70, 18.61, 19.02, 19.27, 21.20, 22.09, 22.97, 23.60, 24.92, 25.59, 26.20, 27.65, 30.42, 31.07, and 35.33 degrees 2-theta±0.2.

In some embodiments, a composition comprising a mixture of Form A and Form C is characterized by six or more peaks in its X-ray powder diffraction pattern selected from those at 8.58, 10.97, 11.81, 14.72, 15.65, 17.32, 17.41, 17.70, 18.61, 19.02, 19.27, 21.20, 22.09, 22.97, 23.60, 24.92, 25.59, 26.20, 27.65, 30.42, 31.07, and 35.33 degrees 2-theta±0.2.

In some embodiments, a composition comprising a mixture of Form A and Form C is characterized by seven or more peaks in its X-ray powder diffraction pattern selected from those at 8.58, 10.97, 11.81, 14.72, 15.65, 17.32, 17.41, 17.70, 18.61, 19.02, 19.27, 21.20, 22.09, 22.97, 23.60, 24.92, 25.59, 26.20, 27.65, 30.42, 31.07, and 35.33 degrees 2-theta±0.2.

In some embodiments, a composition comprising a mixture of Form A and Form C is characterized by eight or more peaks in its X-ray powder diffraction pattern selected from those at 8.58, 10.97, 11.81, 14.72, 15.65, 17.32, 17.41, 17.70, 18.61, 19.02, 19.27, 21.20, 22.09, 22.97, 23.60, 24.92, 25.59, 26.20, 27.65, 30.42, 31.07, and 35.33 degrees 2-theta±0.2.

In some embodiments, a composition comprising a mixture of Form A and Form C is characterized by nine or more peaks in its X-ray powder diffraction pattern selected from those at 8.58, 10.97, 11.81, 14.72, 15.65, 17.32, 17.41, 17.70, 18.61, 19.02, 19.27, 21.20, 22.09, 22.97, 23.60, 24.92, 25.59, 26.20, 27.65, 30.42, 31.07, and 35.33 degrees 2-theta±0.2.

In some embodiments, a composition comprising a mixture of Form A and Form C is characterized by ten or more peaks in its X-ray powder diffraction pattern selected from those at 8.58, 10.97, 11.81, 14.72, 15.65, 17.32, 17.41, 17.70, 18.61, 19.02, 19.27, 21.20, 22.09, 22.97, 23.60, 24.92, 25.59, 26.20, 27.65, 30.42, 31.07, and 35.33 degrees 2-theta±0.2.

In some embodiments, a composition comprising a mixture of Form A and Form C is characterized by eleven or more peaks in its X-ray powder diffraction pattern selected from those at 8.58, 10.97, 11.81, 14.72, 15.65, 17.32, 17.41, 17.70, 18.61, 19.02, 19.27, 21.20, 22.09, 22.97, 23.60, 24.92, 25.59, 26.20, 27.65, 30.42, 31.07, and 35.33 degrees 2-theta±0.2.

In some embodiments, a composition comprising a mixture of Form A and Form C is characterized by twelve or more peaks in its X-ray powder diffraction pattern selected from those at 8.58, 10.97, 11.81, 14.72, 15.65, 17.32, 17.41, 17.70, 18.61, 19.02, 19.27, 21.20, 22.09, 22.97, 23.60, 24.92, 25.59, 26.20, 27.65, 30.42, 31.07, and 35.33 degrees 2-theta±0.2.

In some embodiments, a composition comprising a mixture of Form A and Form C is characterized by thirteen or more peaks in its X-ray powder diffraction pattern selected from those at 8.58, 10.97, 11.81, 14.72, 15.65, 17.32, 17.41, 17.70, 18.61, 19.02, 19.27, 21.20, 22.09, 22.97, 23.60, 24.92, 25.59, 26.20, 27.65, 30.42, 31.07, and 35.33 degrees 2-theta±0.2.

In some embodiments, a composition comprising a mixture of Form A and Form C is characterized by fourteen or more peaks in its X-ray powder diffraction pattern selected from those at 8.58, 10.97, 11.81, 14.72, 15.65, 17.32, 17.41, 17.70, 18.61, 19.02, 19.27, 21.20, 22.09, 22.97, 23.60, 24.92, 25.59, 26.20, 27.65, 30.42, 31.07, and 35.33 degrees 2-theta±0.2.

In some embodiments, a composition comprising a mixture of Form A and Form C is characterized by fifteen or more peaks in its X-ray powder diffraction pattern selected from those at 8.58, 10.97, 11.81, 14.72, 15.65, 17.32, 17.41, 17.70, 18.61, 19.02, 19.27, 21.20, 22.09, 22.97, 23.60, 24.92, 25.59, 26.20, 27.65, 30.42, 31.07, and 35.33 degrees 2-theta±0.2.

In some embodiments, a composition comprising a mixture of Form A and Form C is characterized by sixteen or more peaks in its X-ray powder diffraction pattern selected from those at 8.58, 10.97, 11.81, 14.72, 15.65, 17.32, 17.41, 17.70, 18.61, 19.02, 19.27, 21.20, 22.09, 22.97, 23.60, 24.92, 25.59, 26.20, 27.65, 30.42, 31.07, and 35.33 degrees 2-theta±0.2.

In some embodiments, a composition comprising a mixture of Form A and Form C is characterized by seventeen or more peaks in its X-ray powder diffraction pattern selected from those at 8.58, 10.97, 11.81, 14.72, 15.65, 17.32, 17.41, 17.70, 18.61, 19.02, 19.27, 21.20, 22.09, 22.97, 23.60, 24.92, 25.59, 26.20, 27.65, 30.42, 31.07, and 35.33 degrees 2-theta±0.2.

In some embodiments, a composition comprising a mixture of Form A and Form C is characterized by eighteen or more peaks in its X-ray powder diffraction pattern selected from those at 8.58, 10.97, 11.81, 14.72, 15.65, 17.32, 17.41, 17.70, 18.61, 19.02, 19.27, 21.20, 22.09, 22.97, 23.60, 24.92, 25.59, 26.20, 27.65, 30.42, 31.07, and 35.33 degrees 2-theta±0.2.

In some embodiments, a composition comprising a mixture of Form A and Form C is characterized by nineteen or more peaks in its X-ray powder diffraction pattern selected from those at 8.58, 10.97, 11.81, 14.72, 15.65, 17.32, 17.41, 17.70, 18.61, 19.02, 19.27, 21.20, 22.09, 22.97, 23.60, 24.92, 25.59, 26.20, 27.65, 30.42, 31.07, and 35.33 degrees 2-theta±0.2.

In some embodiments, a composition comprising a mixture of Form A and Form C is characterized by twenty or more peaks in its X-ray powder diffraction pattern selected from those at 8.58, 10.97, 11.81, 14.72, 15.65, 17.32, 17.41, 17.70, 18.61, 19.02, 19.27, 21.20, 22.09, 22.97, 23.60, 24.92, 25.59, 26.20, 27.65, 30.42, 31.07, and 35.33 degrees 2-theta±0.2.

In some embodiments, a composition comprising a mixture of Form A and Form C is characterized by twenty-one or more peaks in its X-ray powder diffraction pattern selected from those at 8.58, 10.97, 11.81, 14.72, 15.65, 17.32, 17.41, 17.70, 18.61, 19.02, 19.27, 21.20, 22.09, 22.97, 23.60, 24.92, 25.59, 26.20, 27.65, 30.42, 31.07, and 35.33 degrees 2-theta±0.2.

In some embodiments, a composition comprising a mixture of Form A and Form C is characterized by peaks in its X-ray powder diffraction pattern selected from those at 8.58, 10.97, 11.81, 14.72, 15.65, 17.32, 17.41, 17.70, 18.61, 19.02, 19.27, 21.20, 22.09, 22.97, 23.60, 24.92, 25.59, 26.20, 27.65, 30.42, 31.07, and 35.33 degrees 2-theta±0.2.

In some embodiments, a composition comprising a mixture of Form A and Form C is characterized by having two peaks in its X-ray powder diffraction pattern selected from among 14.72, 19.02, 22.97, 24.92, 27.65, 30.42 and 31.07 degrees 2-theta±0.2.

In some embodiments, a composition comprising a mixture of Form A and Form C is characterized by having three peaks in its X-ray powder diffraction pattern selected from among 14.72, 19.02, 22.97, 24.92, 27.65, 30.42 and 31.07 degrees 2-theta±0.2.

In some embodiments, a composition comprising a mixture of Form A and Form C is characterized by having four peaks in its X-ray powder diffraction pattern selected from among 14.72, 19.02, 22.97, 24.92, 27.65, 30.42 and 31.07 degrees 2-theta±0.2.

In some embodiments, a composition comprising a mixture of Form A and Form C is characterized by having five peaks in its X-ray powder diffraction pattern selected from among 14.72, 19.02, 22.97, 24.92, 27.65, 30.42 and 31.07 degrees 2-theta±0.2.

In some embodiments, a composition comprising a mixture of Form A and Form C is characterized by having six peaks in its X-ray powder diffraction pattern selected from among 14.72, 19.02, 22.97, 24.92, 27.65, 30.42 and 31.07 degrees 2-theta±0.2.

In some embodiments, a composition comprising a mixture of Form A and Form C is characterized by having peaks in its X-ray powder diffraction pattern at 14.72, 19.02, 22.97, 24.92, 27.65, 30.42 and 31.07 degrees 2-theta±0.2.

In some embodiments, a composition comprising a mixture of Form A and Form C is characterized by having one peak in its X-ray powder diffraction pattern selected from among 15.65, 17.7, 19.27, 21.2, 23.6, 35.33, 14.72, 19.02, 22.97, 24.92, 27.65, 30.42 and 31.07 degrees 2-theta±0.2.

In some embodiments, a composition comprising a mixture of Form A and Form C is characterized by having two peaks in its X-ray powder diffraction pattern selected from among 15.65, 17.7, 19.27, 21.2, 23.6, 35.33, 14.72, 19.02, 22.97, 24.92, 27.65, 30.42 and 31.07 degrees 2-theta±0.2.

In some embodiments, a composition comprising a mixture of Form A and Form C is characterized by having three peaks in its X-ray powder diffraction pattern selected from among 15.65, 17.7, 19.27, 21.2, 23.6, 35.33, 14.72, 19.02, 22.97, 24.92, 27.65, 30.42 and 31.07 degrees 2-theta±0.2.

In some embodiments, a composition comprising a mixture of Form A and Form C is characterized by having four peaks in its X-ray powder diffraction pattern selected from among 15.65, 17.7, 19.27, 21.2, 23.6, 35.33, 14.72, 19.02, 22.97, 24.92, 27.65, 30.42 and 31.07 degrees 2-theta±0.2.

In some embodiments, a composition comprising a mixture of Form A and Form C is characterized by having five peaks in its X-ray powder diffraction pattern selected from among 15.65, 17.7, 19.27, 21.2, 23.6, 35.33, 14.72, 19.02, 22.97, 24.92, 27.65, 30.42 and 31.07 degrees 2-theta±0.2.

In some embodiments, a composition comprising a mixture of Form A and Form C is characterized by having six peaks in its X-ray powder diffraction pattern selected from among 15.65, 17.7, 19.27, 21.2, 23.6, 35.33, 14.72, 19.02, 22.97, 24.92, 27.65, 30.42 and 31.07 degrees 2-theta±0.2.

In some embodiments, a composition comprising a mixture of Form A and Form C is characterized by having seven peaks in its X-ray powder diffraction pattern selected from among 15.65, 17.7, 19.27, 21.2, 23.6, 35.33, 14.72, 19.02, 22.97, 24.92, 27.65, 30.42 and 31.07 degrees 2-theta±0.2.

In some embodiments, a composition comprising a mixture of Form A and Form C is characterized by having eight peaks in its X-ray powder diffraction pattern selected from among 15.65, 17.7, 19.27, 21.2, 23.6, 35.33, 14.72, 19.02, 22.97, 24.92, 27.65, 30.42 and 31.07 degrees 2-theta±0.2.

In some embodiments, a composition comprising a mixture of Form A and Form C is characterized by having nine peaks in its X-ray powder diffraction pattern selected from among 15.65, 17.7, 19.27, 21.2, 23.6, 35.33, 14.72, 19.02, 22.97, 24.92, 27.65, 30.42 and 31.07 degrees 2-theta±0.2.

In some embodiments, a composition comprising a mixture of Form A and Form C is characterized by having ten peaks in its X-ray powder diffraction pattern selected from among 15.65, 17.7, 19.27, 21.2, 23.6, 35.33, 14.72, 19.02, 22.97, 24.92, 27.65, 30.42 and 31.07 degrees 2-theta±0.2.

In some embodiments, a composition comprising a mixture of Form A and Form C is characterized by having eleven peaks in its X-ray powder diffraction pattern selected from among 15.65, 17.7, 19.27, 21.2, 23.6, 35.33, 14.72, 19.02, 22.97, 24.92, 27.65, 30.42 and 31.07 degrees 2-theta±0.2.

In some embodiments, a composition comprising a mixture of Form A and Form C is characterized by having twelve peaks in its X-ray powder diffraction pattern selected from among 15.65, 17.7, 19.27, 21.2, 23.6, 35.33, 14.72, 19.02, 22.97, 24.92, 27.65, 30.42 and 31.07 degrees 2-theta±0.2.

In some embodiments, a composition comprising a mixture of Form A and Form C is characterized by having the following peaks in its X-ray powder diffraction pattern at 15.65, 17.7, 19.27, 21.2, 23.6, 35.33, 14.72, 19.02, 22.97, 24.92, 27.65, 30.42 and 31.07 degrees 2-theta±0.2.

In some embodiments, a composition comprising a mixture of Form A and Form C is characterized by having peaks in its X-ray powder diffraction pattern at 21.20 and 22.97 degrees 2-theta±0.2.

In some embodiments, a composition comprising a mixture of Form A and Form C is characterized by having peaks in its X-ray powder diffraction pattern at 17.32, 21.20, and 22.97 degrees 2-theta±0.2.

In some embodiments, a composition comprising a mixture of Form A and Form C is characterized by having peaks in its X-ray powder diffraction pattern at 17.32, 19.02, 21.20, and 22.97 degrees 2-theta±0.2.

In some embodiments, a composition comprising a mixture of Form A and Form C is characterized by having peaks in its X-ray powder diffraction pattern at 17.32, 17.41, 19.02, 21.20, and 22.97 degrees 2-theta±0.2.

In some embodiments, a composition comprising a mixture of Form A and Form C is characterized by having peaks in its X-ray powder diffraction pattern at 17.32, 17.41, 19.02, 21.20, 22.97, and 31.07 degrees 2-theta±0.2.

In some embodiments, a composition comprising a mixture of Form A and Form C is characterized by having peaks in its X-ray powder diffraction pattern at 11.81, 17.32, 17.41, 19.02, 21.20, 22.97, and 31.07 degrees 2-theta±0.2.

In some embodiments, a composition comprising a mixture of Form A and Form C is characterized by having peaks in its X-ray powder diffraction pattern at 11.81, 17.32, 17.41, 19.02, 21.20, 22.97, 26.20, and 31.07 degrees 2-theta±0.2.

In some embodiments, a composition comprising a mixture of Form A and Form C is characterized by having peaks in its X-ray powder diffraction pattern at 11.81, 17.32, 17.41, 19.02, 21.20, 22.97, 26.20, 27.65, and 31.07 degrees 2-theta±0.2.

In some embodiments, a composition comprising a mixture of Form A and Form C is characterized by having peaks in its X-ray powder diffraction pattern at 8.58, 11.81, 17.32, 17.41, 19.02, 21.20, 22.97, 26.20, 27.65, and 31.07 degrees 2-theta±0.2.

In some embodiments, a composition comprising a mixture of Form A and Form C is characterized by having peaks in its X-ray powder diffraction pattern at 8.58, 11.81, 17.32, 17.41, 19.02, 21.20, 22.97, 25.59, 26.20, 27.65, and 31.07 degrees 2-theta±0.2.

In some embodiments, a composition comprising a mixture of Form A and Form C is characterized by having peaks in its X-ray powder diffraction pattern at 8.58, 10.97, 11.81, 17.32, 17.41, 19.02, 21.20, 22.97, 25.59, 26.20, 27.65, and 31.07 degrees 2-theta±0.2.

In some embodiments, a composition comprising a mixture of Form A and Form C is characterized by an XRPD pattern with substantially the same peaks (degrees 2-theta±0.2), optionally corresponding to d-spacing (angstroms±0.2) and/or relative intensity (%) of:

| Degrees 2-Theta ± 0.2 | d-spacing (Å) | Relative intensity (%) |
|---|---|---|
| 8.58 | 10.30 | 4.8 |
| 10.97 | 8.06 | 3.9 |

-continued

| Degrees 2-Theta ± 0.2 | d-spacing (Å) | Relative intensity (%) |
|---|---|---|
| 11.81 | 7.49 | 9.2 |
| 14.72 | 6.01 | 3.2 |
| 15.65 | 5.66 | 3.1 |
| 17.32 | 5.12 | 18.5 |
| 17.41 | 5.09 | 14.4 |
| 17.70 | 5.00 | 7.5 |
| 18.61 | 4.76 | 2.3 |
| 19.02 | 4.66 | 17.3 |
| 19.27 | 4.60 | 2.7 |
| 21.20 | 4.19 | 100 |
| 22.09 | 4.02 | 3.6 |
| 22.97 | 3.87 | 22.2 |
| 23.60 | 3.77 | 3.1 |
| 24.92 | 3.57 | 3.2 |
| 25.59 | 3.48 | 4.0 |
| 26.20 | 3.40 | 6.9 |
| 27.65 | 3.22 | 5.2 |
| 30.42 | 2.94 | 2.5 |
| 31.07 | 2.88 | 10.2 |
| 35.33 | 2.54 | 2.3 |

In some embodiments, a composition comprising a mixture of Form A and Form C of Compound 1 has one or more of the following characteristics:
(i) an XRPD pattern substantially similar to that depicted in FIG. 8;
(ii) a DSC pattern substantially similar to that depicted in any one of FIG. 9;
(iii) a TGA pattern substantially similar to that depicted in any one of FIG. 10; or
(iv) a melting point including metastable forms of about 68.7° C., 99.5° C., and 209.4° C.

In some embodiments, this disclosure provides a mixture comprising Forms A and D in a ratio of between about 2:98 and about 5:95. In one embodiment, this disclosure provides a mixture comprising Forms A and D in a ratio of between about 5:95 and about 10:90. In one embodiment, this disclosure provides a mixture comprising Forms A and D in a ratio of between about 10:90 and about 15:85. In one embodiment, this disclosure provides a mixture comprising Forms A and D in a ratio of between about 15:85 and about 20:80. In one embodiment, this disclosure provides a mixture comprising Forms A, and D in a ratio of about 50:50. In some embodiments, this disclosure provides a mixture comprising Forms A and D in a ratio of between about 98:2 and about 95:5. In one embodiment, this invention provides a mixture comprising Forms A and D in a ratio of between about 95:5 and about 90:10. In one embodiment, this disclosure provides a mixture comprising Forms A and D in a ratio of between about 90:10 and about 85:15. In one embodiment, this disclosure provides a mixture comprising Forms A and D in a ratio of between about 85:15 and about 80:20.

In some embodiments, a composition comprising a mixture of Form A and Form D is characterized by one or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by two or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by three or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by four or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by five or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by six or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by seven or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by eight or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by nine or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by ten or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by eleven or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by twelve or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by thirteen or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by fourteen or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by fifteen or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by sixteen or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by seventeen or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by eighteen or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by nineteen or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by twenty or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by twenty-one or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by twenty-two or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by twenty-three or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by twenty-four or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by twenty-five or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by twenty-six or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by twenty-seven or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by twenty-eight or more peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by peaks in its X-ray powder diffraction pattern selected from those at 8.69, 9.99, 11.08, 12.34, 15.12, 16.15, 17.38, 17.62, 18.08, 18.67, 19.47, 21.13, 21.60, 22.22, 22.76, 23.50, 23.91, 25.04, 25.69, 26.49, 28.36, 28.52, 29.98, 30.60, 31.84, 33.83, 34.44, 35.74, and 38.77 degrees 2-theta±0.2.

In some embodiments, a composition comprising a mixture of Form A and Form D is characterized by two peaks in its X-ray powder diffraction pattern selected from among 9.99, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by three peaks in its X-ray powder diffraction pattern selected from among 9.99, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by four peaks in its X-ray powder diffraction pattern selected from among 9.99, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by five peaks in its X-ray powder diffraction pattern selected from among 9.99, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by six peaks in its X-ray powder diffraction pattern selected from among 9.99, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by seven peaks in its X-ray powder diffraction pattern selected from among 9.99, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by eight peaks in its X-ray powder diffraction pattern selected from among 9.99, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by nine peaks in its X-ray powder diffraction pattern selected from among 9.99, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by nine peaks in its X-ray powder diffraction pattern selected from among 9.99, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by ten peaks in its X-ray powder diffraction pattern selected from among 9.99, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by eleven peaks in its X-ray powder diffraction pattern selected from among 9.99, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by peaks in its X-ray powder diffraction pattern at 9.99, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by two peaks in its X-ray powder diffraction pattern selected from among 8.69, 9.99, 11.08, 17.62, 18.67, 19.47, 21.13, 22.22, 22.76, 23.5, 25.69, 28.36, 28.52, 29.98, 31.84, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by three peaks in its X-ray powder diffraction pattern selected from among 8.69, 9.99, 11.08, 17.62, 18.67, 19.47, 21.13, 22.22, 22.76, 23.5, 25.69, 28.36, 28.52, 29.98, 31.84, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by four peaks in its X-ray powder diffraction pattern selected from among 8.69, 9.99, 11.08, 17.62, 18.67, 19.47, 21.13, 22.22, 22.76, 23.5, 25.69, 28.36, 28.52, 29.98, 31.84, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by five peaks in its X-ray powder diffraction pattern selected from among 8.69, 9.99, 11.08, 17.62, 18.67, 19.47, 21.13, 22.22, 22.76, 23.5, 25.69, 28.36, 28.52, 29.98, 31.84, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by six peaks in its X-ray powder diffraction pattern selected from among 8.69, 9.99, 11.08, 17.62, 18.67, 19.47, 21.13, 22.22, 22.76, 23.5, 25.69, 28.36, 28.52, 29.98, 31.84, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by seven peaks in its X-ray powder diffraction pattern selected from among 8.69, 9.99, 11.08, 17.62, 18.67, 19.47, 21.13, 22.22, 22.76, 23.5, 25.69, 28.36, 28.52, 29.98, 31.84, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by eight peaks in its X-ray powder diffraction pattern selected from among 8.69, 9.99, 11.08, 17.62, 18.67, 19.47, 21.13, 22.22, 22.76, 23.5, 25.69, 28.36, 28.52, 29.98, 31.84, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by nine peaks in its X-ray powder diffraction pattern selected from among 8.69, 9.99, 11.08, 17.62, 18.67, 19.47, 21.13, 22.22, 22.76, 23.5, 25.69, 28.36, 28.52, 29.98, 31.84, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by ten peaks in its X-ray powder diffraction pattern selected from among 8.69, 9.99, 11.08, 17.62, 18.67, 19.47, 21.13, 22.22, 22.76, 23.5, 25.69, 28.36, 28.52, 29.98, 31.84, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by eleven peaks in its X-ray powder diffraction pattern selected from among 8.69, 9.99, 11.08, 17.62, 18.67, 19.47, 21.13, 22.22, 22.76, 23.5, 25.69, 28.36, 28.52, 29.98, 31.84, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by twelve peaks in its X-ray powder diffraction pattern selected from among 8.69, 9.99, 11.08, 17.62, 18.67, 19.47, 21.13, 22.22, 22.76, 23.5, 25.69, 28.36, 28.52, 29.98, 31.84, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by thirteen peaks in its X-ray powder diffraction pattern selected from among 8.69, 9.99, 11.08, 17.62, 18.67, 19.47, 21.13, 22.22, 22.76, 23.5, 25.69, 28.36, 28.52, 29.98, 31.84, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by fourteen peaks in its X-ray powder diffraction pattern selected from among 8.69, 9.99, 11.08, 17.62, 18.67, 19.47, 21.13, 22.22, 22.76, 23.5, 25.69, 28.36, 28.52, 29.98, 31.84, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by fifteen peaks in its X-ray powder diffraction pattern selected from among 8.69, 9.99, 11.08, 17.62, 18.67, 19.47, 21.13, 22.22, 22.76, 23.5, 25.69, 28.36, 28.52, 29.98, 31.84, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by sixteen peaks in its X-ray powder diffraction pattern selected from among 8.69, 9.99, 11.08, 17.62, 18.67, 19.47, 21.13, 22.22, 22.76, 23.5, 25.69, 28.36, 28.52, 29.98, 31.84, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by seventeen peaks in its X-ray powder diffraction pattern selected from among 8.69, 9.99, 11.08, 17.62, 18.67, 19.47, 21.13, 22.22, 22.76, 23.5, 25.69, 28.36, 28.52, 29.98, 31.84, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by eighteen peaks in its X-ray powder diffraction pattern selected from among 8.69, 9.99, 11.08, 17.62, 18.67, 19.47, 21.13, 22.22, 22.76, 23.5, 25.69, 28.36, 28.52, 29.98, 31.84, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by nineteen peaks in its X-ray powder diffraction pattern selected from among 8.69, 9.99, 11.08, 17.62, 18.67, 19.47, 21.13, 22.22, 22.76, 23.5, 25.69, 28.36, 28.52, 29.98, 31.84, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D Form D is characterized by twenty peaks in its X-ray powder diffraction pattern selected from among 8.69, 9.99, 11.08, 17.62, 18.67, 19.47, 21.13, 22.22, 22.76, 23.5, 25.69, 28.36, 28.52, 29.98, 31.84, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by twenty-one peaks in its X-ray powder diffraction pattern selected from among 8.69, 9.99, 11.08, 17.62, 18.67, 19.47, 21.13, 22.22, 22.76, 23.5, 25.69, 28.36, 28.52, 29.98, 31.84, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by twenty-two peaks in its X-ray powder diffraction pattern selected from among 8.69, 9.99, 11.08, 17.62, 18.67, 19.47, 21.13, 22.22, 22.76, 23.5, 25.69, 28.36, 28.52, 29.98, 31.84, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by twenty-three peaks in its X-ray powder diffraction pattern selected from among 8.69, 9.99, 11.08, 17.62, 18.67, 19.47, 21.13, 22.22, 22.76, 23.5, 25.69, 28.36, 28.52, 29.98, 31.84, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by twenty-four peaks in its X-ray powder diffraction pattern selected from among 8.69, 9.99, 11.08, 17.62, 18.67, 19.47, 21.13, 22.22, 22.76, 23.5, 25.69, 28.36, 28.52, 29.98, 31.84, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by twenty-five peaks in its X-ray powder diffraction pattern selected from among 8.69, 9.99, 11.08, 17.62, 18.67, 19.47, 21.13, 22.22, 22.76, 23.5, 25.69, 28.36, 28.52, 29.98, 31.84, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by peaks in its X-ray powder diffraction pattern at 8.69, 9.99, 11.08, 17.62, 18.67, 19.47, 21.13, 22.22, 22.76, 23.5, 25.69, 28.36, 28.52, 29.98, 31.84, 12.34, 15.12, 16.15, 18.08, 23.91, 26.49, 30.6, 33.83, 34.44, 35.74 and 38.77 degrees 2-theta±0.2.

In some embodiments, a composition comprising a mixture of Form A and Form D is characterized by peaks in its X-ray powder diffraction pattern at 17.38 and 21.60 degrees 2-theta±0.2.

In some embodiments, a composition comprising a mixture of Form A and Form D is characterized by peaks in its X-ray powder diffraction pattern at 17.38, 21.60, and 22.22 degrees 2-theta±0.2.

In some embodiments, a composition comprising a mixture of Form A and Form D is characterized by peaks in its X-ray powder diffraction pattern at 11.08, 17.38, 21.60, and 22.22 degrees 2-theta±0.2.

In some embodiments, a composition comprising a mixture of Form A and Form D is characterized by peaks in its X-ray powder diffraction pattern at 11.08, 17.38, 21.60, 22.22, and 23.91 degrees 2-theta±0.2.

In some embodiments, a composition comprising a mixture of Form A and Form D is characterized by peaks in its X-ray powder diffraction pattern at 11.08, 17.38, 21.13, 21.60, 22.22, and 23.91 degrees 2-theta±0.2.

In some embodiments, a composition comprising a mixture of Form A and Form D is characterized by peaks in its X-ray powder diffraction pattern at 8.69, 11.08, 17.38, 21.13, 21.60, 22.22, and 23.91 degrees 2-theta±0.2.

In some embodiments, a composition comprising a mixture of Form A and Form D is characterized by peaks in its X-ray powder diffraction pattern at 8.69, 11.08, 17.38, 21.13, 21.60, 22.22, 23.91, and 25.69 degrees 2-theta±0.2.

In some embodiments, a composition comprising a mixture of Form A and Form D is characterized by peaks in its X-ray powder diffraction pattern at 8.69, 11.08, 17.38, 21.13, 21.60, 22.22, 23.91, 25.04, and 25.69 degrees 2-theta±0.2.

In some embodiments, a composition comprising a mixture of Form A and Form D is characterized by peaks in its X-ray powder diffraction pattern at 8.69, 11.08, 17.38, 17.62, 21.13, 21.60, 22.22, 23.91, 25.04, and 25.69 degrees 2-theta±0.2.

In some embodiments, a composition comprising a mixture of Form A and Form D is characterized by peaks in its X-ray powder diffraction pattern at 8.69, 11.08, 12.34, 17.38, 17.62, 21.13, 21.60, 22.22, 23.91, 25.04, and 25.69 degrees 2-theta±0.2.

In some embodiments, a composition comprising a mixture of Form A and Form D is characterized by peaks in its X-ray powder diffraction pattern at 8.69, 11.08, 12.34, 17.38, 17.62, 21.13, 21.60, 22.22, 23.91, 25.04, 25.69, and 28.52 degrees 2-theta±0.2.

In some embodiments, a composition comprising a mixture of Form A and Form D is characterized by peaks in its X-ray powder diffraction pattern at 8.69, 11.08, 12.34, 17.38, 17.62, 21.13, 21.60, 22.22, 23.50, 23.91, 25.04, 25.69, and 28.52 degrees 2-theta±0.2.

In some embodiments, a composition comprising a mixture of Form A and Form D is characterized by peaks in its X-ray powder diffraction pattern at 8.69, 11.08, 12.34, 17.38, 17.62, 21.13, 21.60, 22.22, 23.50, 23.91, 25.04, 25.69, and 28.52, 31.84 degrees 2-theta±0.2.

In some embodiments, a composition comprising a mixture of Form A and Form D is characterized by an XRPD pattern with substantially the same peaks (degrees 2-theta±0.2), optionally corresponding to d-spacing (angstroms±0.2) and/or relative intensity (%) of:

| Degrees 2-Theta ± 0.2 | d-spacing (Å) | Relative intensity (%) |
|---|---|---|
| 8.69 | 10.17 | 24.3 |
| 9.99 | 8.85 | 2.0 |
| 11.08 | 7.98 | 60.8 |
| 12.34 | 7.17 | 11.0 |
| 15.12 | 5.85 | 4.1 |
| 16.15 | 5.48 | 2.7 |
| 17.38 | 5.10 | 100 |
| 17.62 | 5.03 | 11.5 |
| 18.08 | 4.90 | 4.9 |
| 18.67 | 4.75 | 6.1 |
| 19.47 | 4.55 | 5.9 |
| 21.13 | 4.20 | 34.3 |
| 21.60 | 4.11 | 84.7 |
| 27.22 | 4.00 | 74.5 |
| 22.76 | 3.90 | 2.0 |
| 23.50 | 3.78 | 7.6 |
| 23.91 | 3.72 | 34.4 |
| 25.04 | 3.55 | 11.7 |
| 25.69 | 3.46 | 16.8 |
| 26.49 | 3.36 | 5.5 |
| 28.36 | 3.14 | 5.0 |
| 28.52 | 3.13 | 8.2 |
| 29.98 | 2.98 | 5.5 |
| 30.60 | 2.92 | 5.5 |
| 31.84 | 2.81 | 7.0 |
| 33.83 | 2.65 | 2.6 |
| 34.44 | 2.60 | 2.0 |
| 35.74 | 7.51 | 2.8 |
| 38.77 | 2.32 | 3.0 |

In some embodiments, a composition comprising a mixture of Form A and Form D of Compound 1 has one or more of the following characteristics:
(I) an XRPD pattern substantially similar to that depicted in FIG. 11;
(ii) a DSC pattern substantially similar to that depicted in any one of FIG. 12;
(iii) a TGA pattern substantially similar to that depicted in any one of FIG. 13; or
(iv) a melting point including metastable forms of about 90.0° C., 111.2° C., 123.5° C. and 223.0° C.

Methods of Providing Solid Forms of Compound 1

The present disclosure provides methods of providing (e.g., making) various solid forms of Compound 1, as well as compositions comprising mixtures of Compound 1 in one or more solid forms and/or an amorphous form.

In some embodiments, solid forms of Compound 1 can be prepared by dissolving Compound 1 (e.g., amorphous Compound 1, crystalline Compound 1, or a mixture thereof) in a suitable solvent and then causing Compound 1 to return to the solid phase. In some embodiments, solid forms of Compound 1 are prepared by combining amorphous and/or crystalline Compound 1 in a suitable solvent under suitable conditions and isolating a solid form of Compound 1. In some embodiments, solid forms of Compound 1 are prepared by dissolving amorphous and/or crystalline Compound 1 in at least one organic solvent at a temperature of between about −60° C. and about 60° C. (e.g., between about 25° C. and about 45° C.) and then subjecting the mixture to conditions suitable for crystallization, thereby obtaining the solid form of Compound 1. In some such embodiments, conditions suitable for crystallization comprise cooling the mixture to a temperature between about −60° C. and about 30° C.

In some embodiments, conditions suitable for crystallization comprise cooling a mixture to a temperature of about 5° C. In some embodiments, conditions suitable for crystallization comprise cooling a mixture to a temperature of about −20° C. In some embodiments, conditions suitable for crystallization comprise cooling a mixture to a temperature of about 20° C. In some embodiments, conditions suitable for crystallization comprise cooling a mixture to a temperature of between about 20° C. and about 60° C. In some embodiments, conditions suitable for crystallization comprise cooling a mixture to a temperature of about −10° C. to about 0° C. In some embodiments, conditions suitable for crystallization comprise cooling a mixture to a temperature of about 0° C. to about 5° C. In some embodiments, conditions suitable for crystallization comprise cooling a mixture to a temperature of about −10° C. to about −20° C.

In some embodiments, solid forms of Compound 1 are prepared by crystallization from a suitable solvent composition comprising one or more solvents. In some embodiments, a suitable solvent composition comprises two solvents in a 1:1 v/v ratio. In some embodiments, a suitable solvent composition comprises two solvents in a 1:2 v/v ratio. In some embodiments, a suitable solvent composition comprises two solvents in a 1:3 v/v ratio. In some embodiments, a suitable solvent composition comprises two solvents in a 1:4 v/v ratio. In some embodiments, a suitable solvent composition comprises two solvents in a 1:5 v/v ratio. In some embodiments, a suitable solvent composition comprises two solvents in a 1:6 v/v ratio. In some embodiments, a suitable solvent composition comprises two solvents in a 1:7 v/v ratio. In some embodiments, a suitable solvent composition comprises two solvents in a 1:8 v/v ratio. In some embodiments, a suitable solvent composition comprises two solvents in a 1:9 v/v ratio. In some embodiments, a suitable solvent composition comprises two solvents in a 1:10 v/v ratio. In some embodiments, a suitable solvent composition comprises two solvents in a 1:11 v/v ratio. In some embodiments, a suitable solvent composition comprises two solvents in a 1:12 v/v ratio. In some embodiments, a suitable solvent composition comprises two solvents in a 1:13 v/v ratio. In some embodiments, a suitable solvent composition comprises two solvents in a 1:14 v/v ratio. In some embodiments, a suitable solvent composition comprises two solvents in a 1:15 v/v ratio. In some embodiments, a suitable solvent composition comprises two solvents in a 1:16 v/v ratio. In some embodiments, a suitable solvent composition comprises two solvents in a 1:17 v/v ratio.

In some embodiments, solids forms of Compound 1 are prepared by slurrying in a suitable solvent or solvent composition at a suitable temperature. In some such embodiments, solid forms of Compound 1 are then isolated via filtration.

In some embodiments, Form A of Compound 1 is prepared from a suitable solvent selected from: methanol, ethanol, acetone, methyl ethyl ketone, methyl isobutyl ketone, acetonitrile, propionitrile, ethyl acetate, tetrahydrofuran (THF), ethanol/acetic acid, acetone/water, THF/water, dioxane/water, methanol/water, acetonitrile/water, 3-methyl-1-butanol, 2-methyl-1-propanol, isopropanol, isobutyl acetate, isopropyl acetate, toluene, n-butyl acetate, dichloromethane (DCM), methyl tert-butyl ether, dimethylsulfoxide (DMSO), dimethylformamide (DMF), acetic acid, hexane, heptane, formic acid, 2-ethoxyethanol, 1-butanol, 2-butanol, ethyl ether, ethanol/water, DMSO/water, and toluene/heptane.

In some embodiments, Form A of Compound 1 is prepared from ethanol/water 9:1 v/v. In some embodiments, Form A of Compound 1 is prepared from acetone/water 9:1 v/v. In some embodiments, Form A of Compound 1 is prepared from THF/water 9:1 v/v. In some embodiments, Form A of Compound 1 is prepared from 1,4-dioxane/water 9:1 v/v. In some embodiments, Form A of Compound 1 is prepared from acetonitrile/water 9:1 v/v. In some embodiments, Form A of Compound 1 is prepared from DMSO/water 9:1 v/v. In some embodiments, Form A of Compound 1 is prepared from ethanol/water 9:1 v/v.

In some embodiments, Form A of Compound 1 is prepared by dissolving Compound 1 in methanol at a suitable temperature (e.g., about 50° C.); and/or cooling the resulting solution to a suitable temperature (e.g., about 25° C.); and/or allowing for slow evaporation of the resulting solution for a suitable period of time so that Form A of Compound 1 forms.

In some embodiments, Form A of Compound 1 is prepared by slurrying crystalline Compound 1 in methanol at a suitable temperature (e.g., about 25° C.) for a suitable period of time (e.g., about two days).

In some embodiments, Form C of Compound 1 is prepared by dissolving Compound 1 in a solvent composition comprising propylene glycol and methyl isobutyl ketone (e.g., in a ratio of about 1:6) at a suitable temperature (e.g., about 50); and/or cooling the resulting solution to a suitable temperature (e.g., about −27° C.) for a suitable period of time (e.g., about two days).

In some embodiments, Form D of Compound 1 is prepared by dissolving Compound 1 in a solvent composition comprising ethylene glycol and methyl isobutyl ketone (e.g., in a ratio of about 1:6) at a suitable temperature (e.g., about 50° C.); and/or cooling the resulting solution to a suitable temperature (e.g., about −27° C.) for a suitable period of time (e.g., about two days).

In some embodiments, a composition comprising a mixture of Form A and Form C of Compound 1 is prepared from propylene glycol/methyl isobutyl ketone. In some embodiments, a composition comprising a mixture of Form A and Form C of Compound 1 is prepared from propylene glycol/methyl isobutyl ketone 1:11 v/v.

In some embodiments, a composition comprising a mixture of Form A and Form D of Compound 1 is prepared from ethylene glycol/methyl isobutyl ketone. In some embodiments, a composition comprising a mixture of Form A and Form D of Compound 1 is prepared from ethylene glycol/methyl isobutyl ketone 1:11 v/v.

In some embodiments, a solid form of Compound 1 is obtained by a process described in Example 2.

In some embodiments, solid forms of Compound 1 precipitate out of solution. In some embodiments, solid forms of Compound 1 crystallize from solution. In some embodiments, solid forms of Compound 1 precipitate out of solution after removal of part or all of the solvent. In some embodiments, solid forms of Compound 1 precipitate out of solution after crash cooling. In some embodiments, solid forms of Compound 1 precipitate out of solution after addition of an anti-solvent.

In some embodiments, solid forms of Compound 1 are optionally isolated. In some embodiments, solid forms of Compound 1 are dried by vacuum at room temperature, followed by gradually increasing the temperature. In some embodiments, solid forms of Compound 1 are collected by filtration.

In some embodiments, a solid form of Compound 1 is prepared by converting one solid form into another solid form.

Pharmaceutical Compositions

The present disclosure also provides pharmaceutical compositions comprising a solid form of Compound 1, and a pharmaceutically acceptable carrier. In some embodiments, a pharmaceutical composition comprises a therapeutically effective amount of an active ingredient (e.g., a solid form of Compound 1) together with a pharmaceutically acceptable carrier. Certain liquid (e.g., for intravenous or intraperitoneal administration) and solid (e.g., for oral administration) formulations of Compound 1 have been described. See, for example, PCT Application No. PCT/US2009/004014, filed Jul. 9, 2009 and published as WO 2010/005580 on Jan. 14, 2010, the entirety of which is hereby incorporated by reference.

As used herein, the phrase "therapeutically effective amount" refers to an amount that produces a desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, stabilizes one or more characteristics of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount may be formulated and/or administered in a single dose. In some embodiments, a therapeutically effective amount may be formulated and/or administered in a plurality of doses, for example, as part of a dosing regimen.

In some embodiments, a pharmaceutical composition comprises Form A of Compound 1 and a pharmaceutically acceptable carrier.

In some embodiments, a pharmaceutical composition comprises Form C of Compound 1 and a pharmaceutically acceptable carrier.

In some embodiments, a pharmaceutical composition comprises a Form D of Compound 1 and a pharmaceutically acceptable carrier.

In some embodiments, this disclosure provides pharmaceutical compositions comprising a mixture of one or more solid forms of Compound 1 and/or amorphous Compound 1 and a pharmaceutically acceptable carrier.

Pharmaceutical compositions described herein can be administered to a subject by any known method, such as orally, parenterally, perineurally, transmucosally, transdermally, intramuscularly, intravenously, intradermally, subcutaneously, intraperitoneally, intraventricularly, intracranially or intratumorally. In some embodiments, provided pharmaceutical compositions are suitable for injection.

In some embodiments, provided pharmaceutical compositions are administered intravenously, and are thus formulated in a form suitable for intravenous administration, i.e. as a liquid preparation. In some embodiments, provided liquid pharmaceutical compositions (e.g., those suitable for intravenous administration) are prepared from a solid form described herein. In some embodiments, a solid form described herein has desirable properties for preparing a liquid formulation, such as, increased solubility.

In some embodiments, a liquid pharmaceutical composition comprises about 0.8 to about 10 mg/mL of Compound 1. In some embodiments, a liquid pharmaceutical composition comprises about 0.25% to about 0.75% (w/v) of Compound 1. In some embodiments, a liquid pharmaceutical composition comprises about 0.5% (w/v) of Compound 1.

In some embodiments, a liquid pharmaceutical composition is prepared from about 0.8 mg to about 10 mg of a solid form of Compound 1 per milliliter of liquid used in the composition.

In some embodiments, a liquid pharmaceutical composition comprises water. In some embodiments, a liquid pharmaceutical composition comprises saline solution, buffer solution, or buffered-saline solution. In some embodiments, a liquid pharmaceutical composition comprises phosphate-buffered saline solution. In some embodiments, phosphate-buffered saline solution is about 30% to about 50% (v/v) of a liquid pharmaceutical composition. In some embodiments, phosphate-buffered saline solution is about 40% (v/v) of a liquid pharmaceutical composition.

In some embodiments, a liquid pharmaceutical composition has a pH between about pH 5 and about pH 9. In some embodiments, a liquid pharmaceutical composition has a pH between about pH 6 and about pH 8. In some embodiments, a liquid pharmaceutical composition is pH 7.4.

In some embodiments, a liquid pharmaceutical composition comprises polyethylene glycol. In some embodiments, polyethylene glycol (e.g., polyethylene glycol 300) is about 40% to about 60% (v/v) of the pharmaceutical composition. In some embodiments, polyethylene glycol (e.g., polyethylene glycol 300) is about 50% (v/v) of the pharmaceutical composition. In some embodiments, polyethylene glycol is polyethylene glycol 200. In some embodiments, polyethylene glycol is polyethylene glycol 300. In some embodiments, polyethylene glycol is polyethylene glycol 400.

In some embodiments, a liquid pharmaceutical composition comprises polysorbate. In some embodiments, polysorbate (e.g., polysorbate 80) is about 5% to about 15% (v/v) of the pharmaceutical composition. In some embodiments, polysorbate (e.g., polysorbate 80) is about 10% (v/v) of the pharmaceutical composition. In some embodiments, polysorbate is polysorbate 20. In some embodiments, polysorbate is polysorbate 80.

In some embodiments, a liquid pharmaceutical composition comprises polyethylene glycol (e.g., polyethylene glycol 300), polysorbate (e.g., polysorbate 80), or a combination thereof. In some embodiments, a liquid pharmaceutical composition comprises about 50% (v/v) polyethylene glycol 300 and about 10% (v/v) polysorbate 80.

The present disclosure also provides methods of preparing provided liquid pharmaceutical compositions comprising Compound 1. In some embodiments, a method comprises steps of (i) providing one or more solid forms of Compound 1; and (ii) formulating the one or more solid forms of Compound 1 with suitable excipients to provide a liquid pharmaceutical composition. In some embodiments, a step of formulating comprises combining one or more solid forms of Compound 1 with aqueous buffered saline, polyethylene glycol (e.g., polyethylene glycol 300) and polysorbate (e.g., polysorbate 80). In some embodiments, a step of formulating comprising combining one or more solid forms of Compound 1 with suitable excipients so that the liquid formulation comprises about 50% (v/v) polyethylene glycol 300 and about 10% (v/v) polysorbate 80 in aqueous-buffered saline.

In some embodiments, provided methods of preparing provided liquid pharmaceutical compositions further comprise a step of sterilizing the composition and/or one or more individual components of the composition (e.g., prior to combining with the other components).

In some embodiments, provided pharmaceutical compositions are administered orally, and are thus formulated in a form suitable for oral administration, i.e. as a solid preparation. Suitable solid oral formulations include tablets, capsules, pills, granules, pellets and the like. In some embodiments, provided solid forms are formulated in a capsule. In some such embodiments, a composition comprises, in addition to Compound 1 and the pharmaceutically acceptable carrier, a hard gelatin capsule.

Oral formulations containing any one of, or mixtures of, the present solid forms can comprise any conventionally used oral forms, including tablets, capsules, buccal forms, troches, or lozenges. In some embodiments, capsules comprise Form A, Form C, or Form D, or any combination thereof, of Compound 1. Capsules or tablets of a particular crystalline form may also be combined with mixtures of other active compounds and/or inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Tablet formulations can be made by conventional compression, wet granulation, or dry granulation methods and utilize pharmaceutically acceptable diluents (fillers), binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations, in some embodiments, utilize standard delay or time release formulations or spansules.

Example excipient systems suitable for preparing formulations of provided solid forms include one or more fillers, disintegrants, and lubricants.

A filler component can be any filler component known in the art including, but not limited to, lactose, microcrystalline cellulose, sucrose, mannitol, calcium phosphate, calcium carbonate, powdered cellulose, maltodextrin, sorbitol, starch, or xylitol.

Disintegrants suitable for use in provided formulations can be selected from those known in the art, including pregelatinized starch and sodium starch glycolate. Other useful disintegrants include croscarmellose sodium, crospovidone, starch, alginic acid, sodium alginate, clays (e.g. veegum or xanthan gum), cellulose floc, ion exchange resins, or effervescent systems, such as those utilizing food acids (such as citric acid, tartaric acid, malic acid, fumaric acid, lactic acid, adipic acid, ascorbic acid, aspartic acid, erythorbic acid, glutamic acid, and succinic acid) and an alkaline carbonate component (such as sodium bicarbonate, calcium carbonate, magnesium carbonate, potassium carbonate, ammonium carbonate, etc.). Disintegrant(s) useful herein can make up from about 4% to about 40% of the composition by weight, preferably from about 15% to about 35%, more preferably from about 20% to about 35%.

Provided pharmaceutical formulations can also contain an antioxidant or a mixture of antioxidants, such as ascorbic acid. Other antioxidants which can be used include sodium ascorbate and ascorbyl palmitate, preferably in conjunction with an amount of ascorbic acid. An example range for the antioxidant(s) is from about 0.5% to about 15% by weight, most preferably from about 0.5% to about 5% by weight.

In some embodiments, an active pharmacological agent(s) comprises from about 0.5% to about 20%, by weight, of the final composition, or in some embodiments, from about 1% to about 5%, and a coating or capsule comprises up to about 8%, by weight, of a final composition.

Formulations described herein can be used in an uncoated or non-encapsulated solid form. In some embodiments, pharmacological compositions are optionally coated with a film coating, for example, comprising from about 0.3% to about 8% by weight of the overall composition. Film coatings useful with provided formulations are known in the art and generally consist of a polymer (usually a cellulosic type of polymer), a colorant and a plasticizer. Additional ingredients such as wetting agents, sugars, flavors, oils and lubricants may be included in film coating formulations to impart certain characteristics to the film coat. Compositions and formulations provided herein may also be combined and processed as a solid, then placed in a capsule form, such as a gelatin capsule.

In some embodiments, an active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

Pharmaceutically acceptable carriers or diluents are well known to those skilled in the art. A carrier or diluent may be a solid carrier or diluent for solid formulations. Solid carriers and diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In addition, provided compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

In some embodiments, pharmaceutical compositions provided herein are controlled release compositions, i.e. compositions in which the compound is released over a period of time after administration. In some embodiments, provided compositions are immediate release compositions, i.e. a composition in which all of the compound is released immediately after administration.

In some embodiments, pharmaceutical compositions can be delivered in a controlled release system. For example, an agent may be administered using liposomes, or other modes of oral administration.

Provided compositions may also include incorporation of an active material into or onto particulate preparations of polymeric compounds such as polylactic acid, polyglycolic acid, hydrogels, etc., or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Preparation of solid pharmaceutical compositions is well understood in the art, for example by mixing, granulating, or tablet-forming processes. An active therapeutic ingredient is often mixed with excipients which are pharmaceutically acceptable and compatible with the active ingredient. For oral administration, compounds or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions.

Uses of Compound 1 and Pharmaceutical Compositions Thereof

Compound 1 (e.g., solid forms of Compound 1) or a pharmaceutical composition thereof is useful for modulating HGF/SF activity in a patient or a biological sample. In some embodiments, Compound 1 (e.g., solid forms of Compound 1) or a pharmaceutical composition thereof is useful for providing antifibrotic and antiapoptotic activities. Compound 1 is a mimic of HGF/SF and is useful in the treatment of any disease, disorder or condition in which prophylactic and/or therapeutic administration of HGF/SF would be useful.

The present disclosure provides methods comprising administering a therapeutically effective amount of one or more solid forms of Compound 1 to a subject in need thereof.

In some embodiments, the present disclosure provides methods comprising (i) formulating one or more solid forms of Compound 1 to provide a pharmaceutical composition: and (ii) administering the pharmaceutical composition to a subject in need thereof.

In some embodiments, the present disclosure provides methods comprising administering a pharmaceutical composition comprising Compound 1 to a subject in need thereof, wherein the pharmaceutical composition was obtained by formulating one or more solid forms of Compound 1 with suitable excipients.

The present disclosure also provides methods for the use of solid forms of Compound 1, or a pharmaceutical composition thereof, for treating or lessening the severity of a disease or disorder associated with HGF/SF activity or amenable to treatment by modulating HGF/SF activity.

In some embodiments, the present disclosure provides a method for treating or lessening the severity of a disease or disorder selected from fibrotic liver disease, hepatic ischemia-reperfusion injury, cerebral infarction, ischemic heart disease, renal disease and lung (pulmonary) fibrosis.

In some embodiments, a method is for treating or lessening the severity of a disease or disorder selected from liver fibrosis associated with hepatitis C, hepatitis B, delta hepatitis, chronic alcoholism, non-alcoholic steatohepatitis, extrahepatic obstructions (stones in the bile duct), cholangiopathies (primary biliary cirrhosis and sclerosing cholangitis), autoimmune liver disease, and inherited metabolic disorders (Wilson's disease, hemochromatosis, and alpha-1 antitrypsin deficiency); damaged and/or ischemic organs, transplants or grafts; ischemia/reperfusion injury; stroke; cerebrovascular disease; myocardial ischemia; atherosclerosis; renal failure; renal fibrosis and idiopathic pulmonary fibrosis.

In some embodiments, the present disclosure provides a method for treating wounds (e.g., accelerating healing of wounds); promoting vascularization of a damaged and/or ischemic organ, transplant or graft; ameliorating ischemia/reperfusion injury in the brain, heart, liver, kidney, and other tissues and organs; normalizing myocardial perfusion as a consequence of chronic cardiac ischemia or myocardial infarction; increasing development of collateral vessel development after vascular occlusion or to ischemic tissues or organs; or treating a disease or condition selected from fibrotic diseases, hepatic disease including fibrosis and cirrhosis, lung fibrosis, radiocontrast nephropathy, fibrosis secondary to renal obstruction, renal trauma and transplantation, renal failure secondary to chronic diabetes and/or hypertension, and/or diabetes mellitus.

In some embodiments, solid forms of Compound 1, or a pharmaceutical composition thereof, are useful for treatment of various demyelinating diseases and traumatic diseases of the central nervous system, such as spinal cold injury, traumatic brain injury, multiple sclerosis and various hereditary neurodegenerative diseases, such as, but not limited to, leukodystrophies including metachromatic leukodystrophy, Refsum's disease, adrenoleukodystrophy, Krabbe's disease, phenylketonuria, Canavan disease, Pelizaeus-Merzbacher disease and Alexander's disease.

In some embodiments, solid forms of Compound 1 are useful for treatment of a chronic obstructive pulmonary disease such as emphysema, or secondary effects of tobacco abuse or smoking, chronic bronchitis, asthma, cystic fibrosis, alpha-1 antitrypsin deficiency, bronchiectasis, and some forms of bullous lung diseases.

In some embodiments, solid forms of Compound 1 are useful for treatment of fibrotic diseases of connective tissue, such as, but not limited to, scleroderma, systemic sclerosis, generalized scleroderma, limited scleroderma and post-surgical adhesions.

In some embodiments, solid forms of Compound 1 are useful for treatment of muscular dystrophy, amyotrophic lateral sclerosis or chronic heart failure.

In some embodiments, the present disclosure provides a method of treating or ameliorating a renal disease, condition or disorder. In some embodiments, a renal disease, condition, or disorder is selected from renal trauma, renal transplant, renal failure, or renal fibrosis.

In some embodiments, the present disclosure provides a method of reducing severity of delayed graft function in a patient that has received a kidney transplant, the method comprising administering to the patient a solid form of Compound 1, or a pharmaceutical composition thereof. In some embodiments, a patient has received a deceased donor kidney. In some embodiments, a patient has received a live donor kidney. Reduced severity of delayed graft function can be assessed by one or more of the following criteria: (i) the number of days a patient remains dialysis dependent; (ii) estimated creatinine clearance or renal function; and/or (iii) urine output.

In some embodiments, a patient has not previously undergone a kidney transplant. In some embodiments, a patient has not previously received a donor kidney. In some embodiments, a patient has not previously received a deceased donor kidney. In some embodiments, a patient has not previously received a live donor kidney.

In some embodiments, a patient has poor renal function after undergoing a kidney transplant. In some embodiments, a patient has poor renal function in the first 12, 24, 36, or 48 hours after undergoing a kidney transplant. In some embodiments, a patient has poor renal function in the first 24 hours after undergoing a kidney transplant. In some embodiments, poor renal function is evidenced by an average urine output of less than 50 mL per hour over any 8 consecutive hours.

In some embodiments, a patient requires dialysis within the first 1, 2, 3, 4, 5, 6, or 7 days after undergoing a kidney transplant.

In some embodiments, the present disclosure provides a method of preventing acute kidney injury after cardiac surgery involving cardiopulmonary bypass, the method comprising administering to a patient a solid form of Compound 1, or a pharmaceutical composition thereof.

In some embodiments, a patient has undergone a non-emergent cardiac surgical procedure selected from (i) coronary artery bypass graft (CABG), (ii) aortic valve replacement or repair with or without aortic root repair, (iii) mitral, tricuspid, or pulmonic valve replacement or repair, (iv) combined replacement of several cardiac valves, (v) CABG with aortic, mitral, tricuspid, or pulmonic valve replacement or repair, or (vi) CABG with combined cardiac valve replacement or repair.

In some embodiments, a patient has one or more of the following risk factors:
(i) estimated glomerular filtration rate (eGFR) of ≥20 and <30 mL/min/1.73 m2;
(ii) estimated glomerular filtration rate (eGFR) of ≥30 and <60 mL/min/1.73 m2;
(iii) estimated glomerular filtration rate (eGFR) of ≥60 mL/min/1.73 m2;
(iv) combined valve and coronary surgery;
(v) previous cardiac surgery with sternotomy;
(vi) left ventricular ejection fraction (LVEF) <35% by invasive or noninvasive diagnostic cardiac imaging within 90 days prior to surgery;
(vii) diabetes mellitus requiring insulin treatment;
(viii) non-insulin-requiring diabetes with documented presence of at least moderate (+2) proteinuria on urine analysis;
(ix) documented to be NYHA Class III or IV within 1 year prior to surgery; and/or
(x) 75 years old or greater.

In some embodiments, a patient has presented for the non-emergent cardiac surgical procedure without prior evidence of active renal injury, as defined to be no acute rise in serum creatinine >0.3 mg/dL and/or no 50% increase in serum creatinine between the time of screening and surgery.

Exemplary Embodiments

The following numbered embodiments, while non-limiting, are exemplary of certain aspects of the disclosure:
1. A solid form of Compound 1:

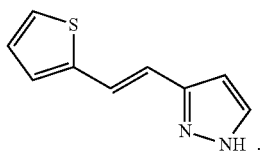

2. The solid form of embodiment 1, wherein the solid form is crystalline.
3. The solid form of embodiment 2, wherein Compound 1 a solvate, a heterosolvate, a hydrate, or an unsolvated form.
4. The solid form of embodiment 2, wherein Compound 1 is an unsolvated form.
5. The solid form of embodiment 2 or 3, wherein the solid form is characterized by one or more peaks in its X-ray powder diffraction pattern selected from those at 8.60, 15.61, 17.22, 17.30, 17.35, 21.04, 22.05, 23.41, 24.97, 25.63, 26.10 and 35.06 degrees 2-theta±0.2.
6. The solid form of embodiment 5, wherein the solid form is characterized by two or more peaks in its X-ray powder diffraction pattern selected from those at 8.60, 15.61, 17.22, 17.30, 17.35, 21.04, 22.05, 23.41, 24.97, 25.63, 26.10 and 35.06 degrees 2-theta±0.2.
7. The solid form of embodiment 6, wherein the solid form is characterized by three or more peaks in its X-ray powder diffraction pattern selected from those at 8.60, 15.61, 17.22, 17.30, 17.35, 21.04, 22.05, 23.41, 24.97, 25.63, 26.10 and 35.06 degrees 2-theta±0.2.
8. The solid form of any one of embodiments 3-7, wherein the solid form is characterized by having peaks in its X-ray powder diffraction pattern at 17.30 and 17.35 degrees 2-theta±0.2.
9. The solid form of any one of embodiments 3-8, wherein the solid form is characterized by having peaks in its X-ray powder diffraction pattern at 8.60, 17.30, and 17.35 degrees 2-theta±0.2.
10. The solid form of any one of embodiments 3-9, wherein the solid form is characterized by having the following peaks in its X-ray powder diffraction pattern (degrees 2-theta±0.2):

| Degrees 2-Theta |
| --- |
| 8.60 |
| 15.61 |
| 17.22 |
| 17.30 |
| 17.35 |
| 21.04 |
| 22.05 |
| 23.41 |
| 24.97 |
| 25.63 |
| 26.10 |
| 35.06 |

11. The solid form of any one of embodiments 3-10, wherein the solid form is characterized by having the following peaks (degrees 2-theta±0.2), corresponding to the following d-spacing (angstroms±0.2), in its X-ray powder diffraction pattern:

| Degrees 2-Theta | d-spacing (Å) |
| --- | --- |
| 8.60 | 10.27 |
| 15.61 | 5.67 |
| 17.30 | 5.12 |
| 17.35 | 5.11 |
| 21.04 | 4.22 |
| 22.05 | 4.03 |
| 23.41 | 3.80 |
| 24.97 | 3.56 |
| 25.63 | 3.47 |
| 26.10 | 3.41 |
| 35.06 | 2.56 |

12. The solid form of any one of embodiments 3-11, wherein the solid form is Form A.
13. A composition comprising the solid form of any one of the preceding embodiments.
14. The composition of embodiment 13, wherein the composition comprises at least about 90% by weight crystalline Compound 1.
15. The composition of embodiment 14, wherein the composition comprises at least about 95% by weight crystalline Compound 1.
16. The composition of embodiment 15, wherein the composition is substantially free of amorphous Compound 1.
17. A pharmaceutical composition comprising the solid form of any one of the preceding embodiments.
18. A pharmaceutical composition prepared from a solid form of any one of the preceding embodiments.

19. A method for mimicking HGF/SF activity in a patient, comprising the step of administering to the patient the solid form of any one of embodiments 1-12, the composition of any one of embodiment 13-16, or the pharmaceutical composition of embodiment 17 or 18.

20. A method for treating a disease or disorder associated with HGF/SF activity or amenable to treatment by modulating HGF/SF activity, comprising the step of administering to the patient the solid form of any one of embodiments 1-12, the composition of any one of embodiment 13-16, or the pharmaceutical composition of embodiment 17 or 18.

21. The method of embodiment 20, wherein the disease or disorder is selected from fibrotic liver disease, hepatic ischemia-reperfusion injury, cerebral infarction, ischemic heart disease, renal disease, lung fibrosis, liver fibrosis associated with hepatitis C, hepatitis B, delta hepatitis, chronic alcoholism, non-alcoholic steatohepatitis, extrahepatic obstructions, cholangiopathies, autoimmune liver disease, Wilson's disease, hemochromatosis, alpha-1 antitrypsin deficiency, damaged and/or ischemic organs, transplants or grafts, ischemia/reperfusion injury, stroke, cerebrovascular disease, myocardial ischemia, atherosclerosis, renal failure, renal fibrosis, idiopathic pulmonary fibrosis, wounds, ischemia/reperfusion injury in the brain, heart, liver, kidney, and other tissues and organs, myocardial perfusion as a consequence of chronic cardiac ischemia or myocardial infarction, fibrotic diseases, hepatic disease including fibrosis and cirrhosis, radiocontrast nephropathy, fibrosis secondary to renal obstruction, renal trauma, renal failure secondary to chronic diabetes and/or hypertension, diabetes mellitus, demyelinating diseases, traumatic diseases of the central nervous system, spinal cold injury, traumatic brain injury, multiple sclerosis, hereditary neurodegenerative diseases, chronic obstructive pulmonary disease, fibrotic diseases of connective tissue, muscular dystrophy, amyotrophic lateral sclerosis or chronic heart failure.

22. The method of embodiment 21, wherein the disease or disorder is selected from fibrotic liver disease, hepatic ischemia-reperfusion injury, cerebral infarction, ischemic heart disease, renal disease or lung fibrosis.

23. The method of embodiment 21, wherein the disease or disorder is selected from liver fibrosis associated with hepatitis C, hepatitis B, delta hepatitis, chronic alcoholism, non-alcoholic steatohepatitis, extrahepatic obstructions, cholangiopathies, autoimmune liver disease, Wilson's disease, hemochromatosis, and alpha-1 antitrypsin deficiency, damaged and/or ischemic organs, transplants or grafts, ischemia/reperfusion injury, stroke, cerebrovascular disease, myocardial ischemia, atherosclerosis, renal failure, renal fibrosis, or idiopathic pulmonary fibrosis.

24. The method of embodiment 21, wherein the disease or disorder is selected from demyelinating diseases, traumatic diseases of the central nervous system, spinal cold injury, traumatic brain injury, multiple sclerosis, and hereditary neurodegenerative diseases.

25. The method of embodiment 24, wherein the hereditary neurodegenerative diseases are selected from leukodystrophies including metachromatic leukodystrophy, Refsum's disease, adrenoleukodystrophy, Krabbe's disease, phenylketonuria, Canavan disease, Pelizaeus-Merzbacher disease and Alexander's disease.

26. The method of embodiment 21, wherein the chronic obstructive pulmonary disease is selected from emphysema, chronic bronchitis, asthma, cystic fibrosis, alpha-1 antitrypsin deficiency, bronchiectasis, and bullous lung diseases.

27. The method of embodiment 21, wherein the fibrotic diseases of connective tissue is selected from scleroderma, systemic sclerosis, generalized scleroderma, limited scleroderma and post-surgical adhesions.

28. The method of embodiment 21, wherein the disease or disorder is selected from muscular dystrophy, amyotrophic lateral sclerosis or chronic heart failure.

29. A method for reducing the severity of delayed graft kidney function in a patient that has received a kidney transplant, the method comprising administering to the patient the solid form of any one of embodiments 1-12, the composition of any one of embodiment 13-16, or the pharmaceutical composition of embodiment 17 or 18.

30. The method of embodiment 19, wherein the patient has received a deceased donor kidney.

31. A method for preventing acute kidney injury after cardiac surgery involving cardiopulmonary bypass, the method comprising administering to a patient the solid form of any one of embodiment 1-12, the composition of any one of embodiment 13-16, or the pharmaceutical composition of embodiment 17 or 18.

32. A solid form of Compound 1 obtained by a process described herein.

EXAMPLES

The following examples are presented in order to more fully illustrate the preferred embodiments of the invention. They should in no way be construed, however, as limiting the broad scope of the invention.

Example 1: Synthesis of Compound 1

Unless otherwise indicated, starting materials are either commercially available or readily accessible through laboratory synthesis by anyone reasonably familiar with the art.

As described in WO 2004/058721, Compound 1 was synthesized according to Scheme 1.

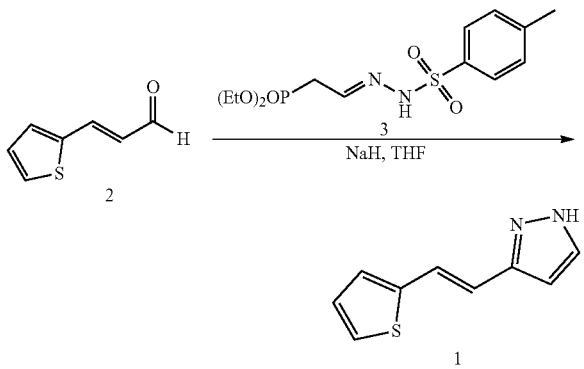

To a solution of diethoxyphosphorylacetaldehyde tosylhydrazone (3, 75 g) in 400 mL of THF was added 11.6 g of 60% NaH in portions, and the solution was stirred for 15 min. The solution was cooled to 0° C., and then a solution of 3-(2-thienyl)acrylaldehyde (2) in 100 mL THF was added dropwise. The reaction was then stirred at room temperature for 1 hour, then at reflux for 1 hour. The reaction mixture was partitioned between 5% $NaH_2PO_4$ and ethyl acetate. The organic layer was separated, washed with water and brine, dried over magnesium sulfate, filtered and concentrated to provide the crude title product as a brown oil. Purification via silica gel column chromatography afforded 8.3 g of a yellow powder. Trituration with dichloromethane/hexane afforded 4.4 g of yellow powder having >98% purity: $^1$H NMR (CDCl$_3$) δ 6.47 (d, 1H, J=1.5 Hz), 6.93 (d, 1H, J=9.9 Hz), 6.99 (dd, 1H, J=3.9, 2.1 Hz), 7.06 (d, 1H, J=2.1 Hz), 7.20 (d, 1H, J=3.9 Hz), 7.22 (d, 1H, J=9.9 Hz), 7.57 (d, 1H, J=1.5 Hz).

The conversion of 3-arylacrylaldehydes into substituted pyrazoles via treatment with diethoxyphosphorylacetaldehyde tosylhydrazone (8) is described in the literature (Almirante, N., Cerri, A.; Fedrizzi, G., Marazzi, G.; Santagostino, M. *Tetrahedron Let.* 1998, 39, 3287). 3-(2-Thienyl)acrylaldehyde (2) was prepared from 2-thienaldehyde and acetaldehyde as described in Heskin, H., Miller, R. E., Nord, F. F. *J. Org. Chem.* 1951, 16, 199.

Example 2 Crystallization Screen of Compound

To a three-necked round bottom flask was added 100 mg of Compound and a suitable solvent. The resulting mixture was stirred at appropriate temperature for 30 In certain cases, the reaction mixture became clear solution. In these cases, the reaction mixture was cooled to an appropriate temperature. Crystal formation was observed in some cases. Crystals were collected by filtration and dried under vacuum at 25-30° C. to afford dry product. The results of the screen are summarized in Table 1.

TABLE 1

Results of crystallization screen of Compound 1.

| Entry | Solvent | Input of 1 | Solvent Volume | Clear solution observed at (° C.) | Crystal formation started at (° C.) | Output (g) | Yield (%) | Solid Form Observed |
|---|---|---|---|---|---|---|---|---|
| 1 | Methanol | 3 g | 6 mL | 40-45 | 0 to −5 | 1.66 | 55.3 | A |
| 2 | Ethanol | 3 g | 7.5 mL | 40-45 | 20-25 | 1.08 | 36.0 | A |
| 3 | Acetone | 3 g | 6 mL | 40-45 | 0-5 | 1 | 33.3 | A |
| 4 | Ethyl methyl Ketone | 3 g | 6 mL | 40-45 | 0 to −5 | 0.72 | 24.0 | A |
| 5 | Methyl isobutyl ketone | 3 g | 16.5 mL | 40-45 | 0 to −5 | 1.03 | 34.3 | A |
| 6 | Acetonitrile | 3 g | 21 mL | 40-45 | 25-30 | 0.86 | 28.7 | A |
| 7 | Propionitrile | 3 g | 13.5 mL | 40-45 | 15-20 | 1.4 | 46.7 | A |
| 8 | Ethyl Acetate | 3 g | 13.5 mL | 40-45 | 25-30 | 1.13 | 37.7 | A |
| 9 | Tetrahydrofuran (THF) | 3 g | 4.5 mL | 40-45 | 0-5 | 0.7 | 23.3 | A |
| 10 | 1,4-Dioxane | 3 g | 16.5 mL | 40-45 | 0-5 | 0.58 | 19.3 | A |
| 11 | 2-Ethoxyethanol | 3 g | 6 mL | 40-45 | 0-5 | 0.2 | 6.7 | A |
| 12 | Ethanol/Acetic acid (9:1) | 3 g | 6 mL | 40-45 | 0-5 | 1.46 | 48.7 | A |
| 13 | Acetone/Water (9:1) | 3 g | 4.5 mL | 40-45 | 25-30 | 0.6 | 20.0 | A |
| 14 | THF/Water (9:1) | 3 g | 3 mL | 40-45 | 15-20 | 0.83 | 27.7 | A |
| 15 | 1,4-Dioxane/Water (9:1) | 3 g | 4.5 mL | 40-45 | 10 to 15 | 0.86 | 28.7 | A |
| 16 | Methanol/water (9:1) | 3 g | 10.5 mL | 40-45 | 5 to 10 | 1.25 | 41.7 | A |
| 17 | Acetonitrile/water (9:1) | 3 g | 12 mL | 40-45 | 25-30 | 0.9 | 30.0 | A |
| 18 | 1-Butanol | 3 g | 19.5 mL | 40-45 | 0 to 5 | 0.44 | 14.7 | A |
| 19 | 2-Butanol | 3 g | 22.5 mL | 40-45 | 0 to −5 | 0 | 0 | A |
| 20 | 3-Methyl-1-butanol | 3 g | 22.5 mL | 40-45 | 0-5 | 1.02 | 34.0 | A |
| 21 | 2-Methyl-1-propanol | 3 g | 33 mL | 40-45 | 0-5 | 1.15 | 38.3 | A |
| 22 | Isopropanol | 3 g | 21 mL | 40-45 | 0-5 | 0.5 | 16.7 | A |
| 23 | Isobutyl acetate | 3 g | 31.5 mL | 40-45 | 10 to 15 | 1.62 | 54.0 | A |
| 24 | Isopropyl acetate | 3 g | 34.5 mL | 40-45 | 10 to 15 | 1.05 | 35.0 | A |
| 25 | Toluene | 3 g | 120 mL | 40-45 | 10 to 15 | 2.15 | 71.7 | A |
| 26 | n-Butyl acetate | 3 g | 21 mL | 40-45 | 0-5 | 1.4 | 46.7 | A |
| 27 | Dichloromethane (DCM) | 3 g | 21 mL | 40-45 | 0-5 | 2 | 66.7 | A |
| 28 | Methyl tert-butyl ether | 3 g | 60 mL | 40-45 | 0-5 | 1.4 | 46.7 | A |
| 29[a] | Dimethylsulfoxide (DMSO) | 3 g | 3 mL | 40-45 | N/A | 2.93 | 97.7 | A |
| 30[b] | Dimethylformamide (DMF) | 3 g | 3 mL | 38-40 | N/A | 2.97 | 99.0 | A |
| 31[a] | DMSO/water (1:1) | 3 g | 3 mL | 32 | N/A | — | — | A |
| 32[a] | 2-Methyltetrahydrofuran | 3 g | 7.5 mL | 40-45 | 5-10 | — | — | A |
| 33[a] | Ethanol/water (9:1) | 3 g | 10.5 mL | 40-45 | 15-20 | — | — | A |
| 34[c] | Acetic acid | 3 g | 30 mL | 40-45 | N/A | 2.6 | 86.7 | A |
| 35[d] | Glycerol in methyl isobutyl ketone (MIBK) | 3 g | 1.5 mL + 16.5 mL (MIBK) | 40-45 | −10 to −5 | 0.95 | 31.7 | A |
| 36[e] | Propylene glycol in MIBK | 3 g | 1.5 mL + 16.5 mL (MIBK) | 40-45 | −50 to −60 | 1.78 | 59.3 | A and C |
| 37[e] | Ethylene glycol in MIBK | 3 g | 1.5 mL + 16.5 mL (MIBK) | 40-45 | −50 to −60 | 1.89 | 63.0 | A and D |

[a]Solid not formed at 0-5° C. and at −40° C. Raised temperature to room temperature and added 12 mL water. Crystal formed and collected by filtration.
[b]Solid not formed at 0-5° C. and at −60° C. Raised temperature to room temperature and added 12 mL water. Crystal formed and collected by filtration.
[c]Solid not formed at room temperature. Added 12 mL water. Crystal formed and collected by filtration.
[d]Glycerol not miscible in MIBK. Heating needed.
[e]Heating needed.

As can be seen from the results disclosed in Table 1, Forms A, C, and D of Compound 1 can be prepared under different conditions.

Example 3: Characterization of Solid Forms and Mixtures Thereof from Crystallization Screen of Example 2

General Methods:
X-Ray Powder Diffraction (XRPD)

XRPD was performed with PANalytical X-ray diffractometer PW 1710, where the tube anode was Cu with Kα radiation. The pattern was collected in step scan mode (step size of 0.02° 2θ, counting time 2.4 s/step). The sample was measured without any special treatment other than the application of slight pressure to get a flat surface. The measurements were performed in an ambient air atmosphere.

Thermo Gravimetric—Fourier Transform Infrared (IG-FTIR) and Thermo Gravimetric Analysis The TG-FTIR instrument consists of a thermogravimetric analyzer (TG) coupled with a Fourier-Transform Infrared (FTIR) spectrometer for the analysis of evolved gases such as $H_2O$. Samples were characterized by their mass loss combined with characterization of the evolved components. Thermo gravimetric measurements were carried out with a Netzsch Thermo-Microbalance TG 209 coupled to a Bruker FTIR Spectrometer Vector 22. Sample pans with a pinhole were used under an $N_2$ atmosphere, at a heating rate of 10 K/min, with a temperature range of 25 to 250° C. Additional Thermo Gravimetric Analysis was conducted using a TA Instruments Q500 TGA under various conditions.

Differential Scanning Calorimetry (DSC)

Thermal analysis was carried out with a Perkin Elmer DSC7 with the following experimental conditions: 3 to 6 mg sample mass, closed gold sample pan, temperature range from −50° C. to 120° C., and heating rate 20 K/min. The samples were weighed in air or dry $N_2$ atmosphere. Additional thermal analysis was conducted using a TA Instruments Q1000 DSC using hermetic aluminum pans under various conditions.

Filtration

During the following experiments: suspension equilibration, precipitation experiment, recrystallization, relative stability experiments and water solubility experiment, a filtration step was conducted. Centrifugal filter devices: Ultrafree-CL (0.22 μm), Millipore; Centrifuge type or Eppendorf 5804R were used at a temperature of 22° C. and centrifugation program of 2 min 3000 rpm.

Form A

Form A was prepared under conditions described in Table 1. The XRPD pattern of Form A of Compound 1 is depicted in FIG. 1, and the corresponding data are summarized below:

| Degrees 2-Theta | d-spacing (Å) | Relative intensity (%) |
|---|---|---|
| 8.60 | 10.27 | 23.1 |
| 15.61 | 5.67 | 1.0 |
| 17.22 | 5.15 | 19.3 |
| 17.30 | 5.12 | 100 |
| 17.35 | 5.11 | 58.2 |
| 21.04 | 4.22 | 4.4 |
| 22.05 | 4.03 | 1.5 |
| 23.41 | 3.80 | 2.6 |
| 24.97 | 3.56 | 2.4 |
| 25.63 | 3.47 | 2.1 |
| 26.10 | 3.41 | 1.8 |
| 35.06 | 2.56 | 2.3 |

TGA and DSC analysis were performed on 28 samples of Form A, prepared under various conditions from Table 1. Table 2 summarizes the TGA and DSC data from these experiments.

Figure 2:
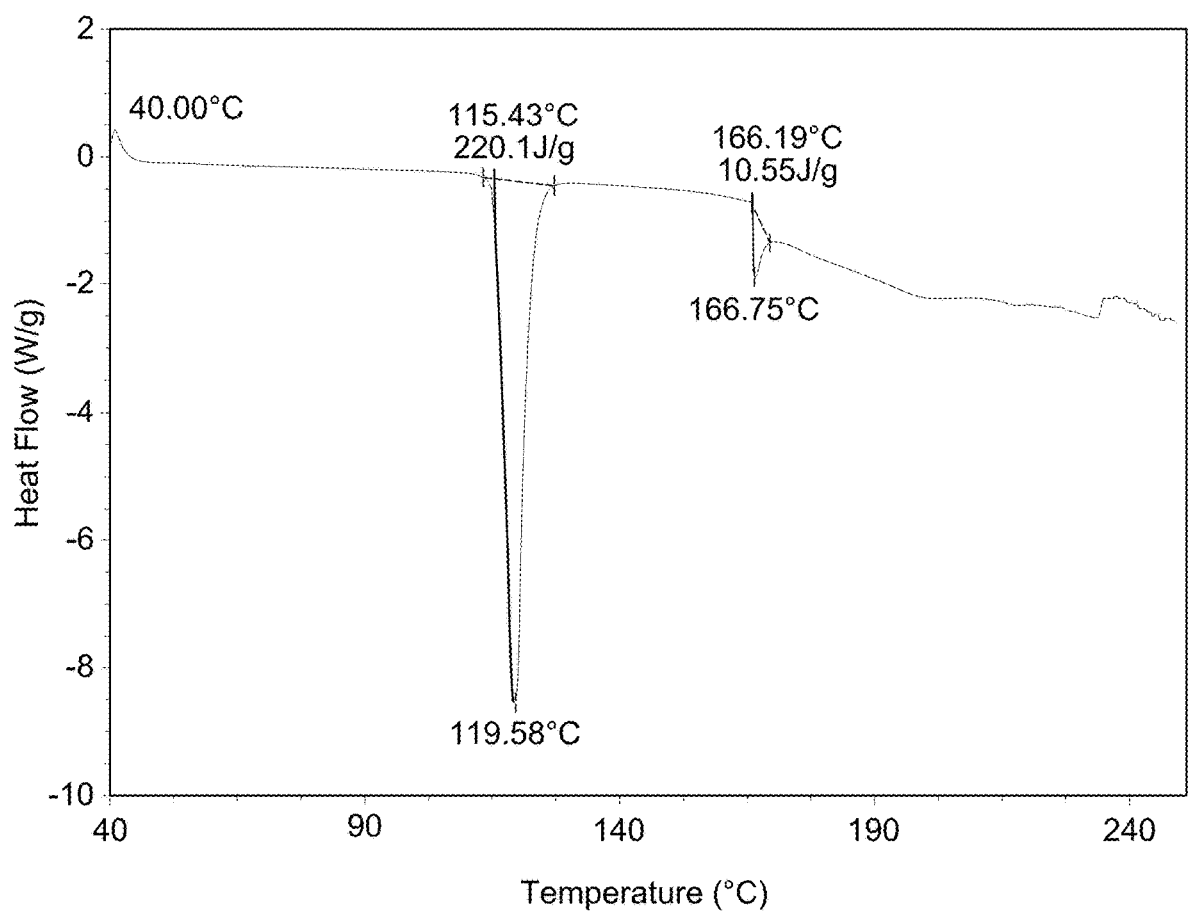
FIG. 2 provides Differential Scanning Calorimeter (DSC) thermogram of solid Form A.
Figure 3:
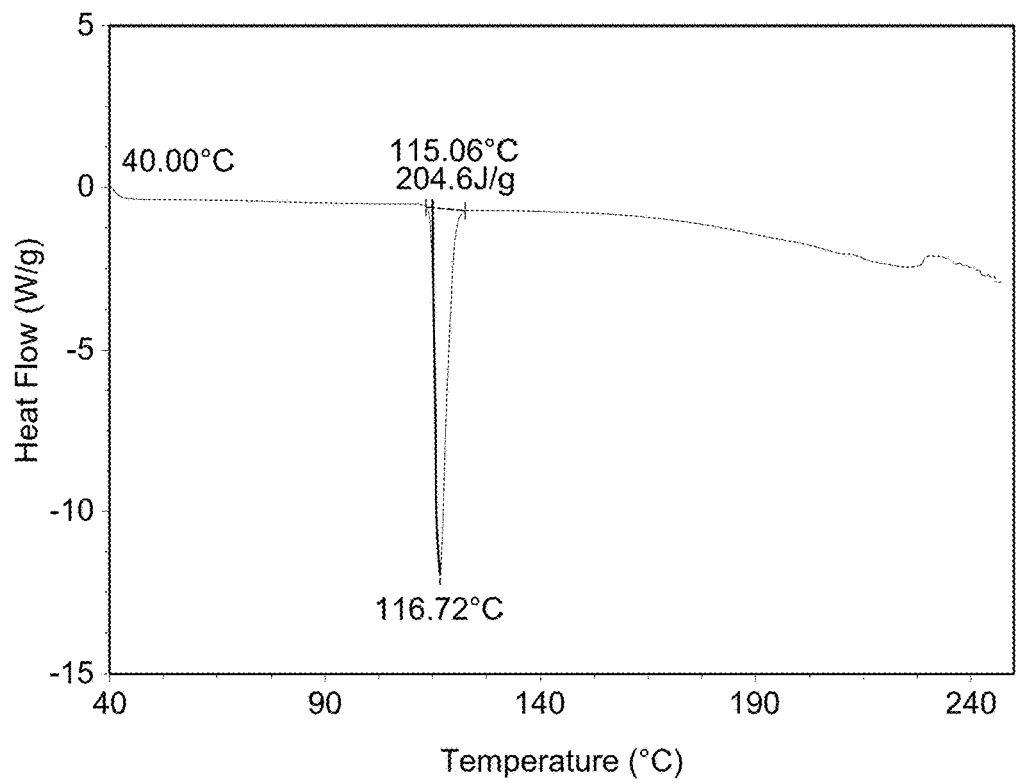
FIG. 3 provides another DSC thermogram of solid Form A.
Figure 4:
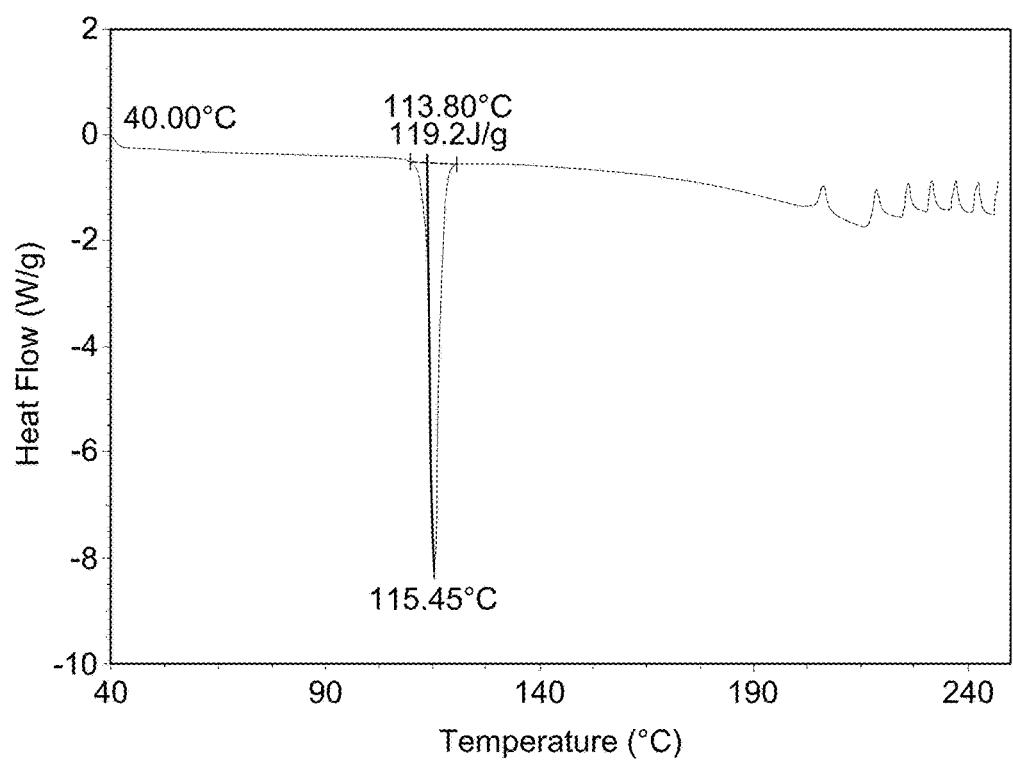
FIG. 4 provides a further DSC thermogram of solid Form A.
Figure 5:
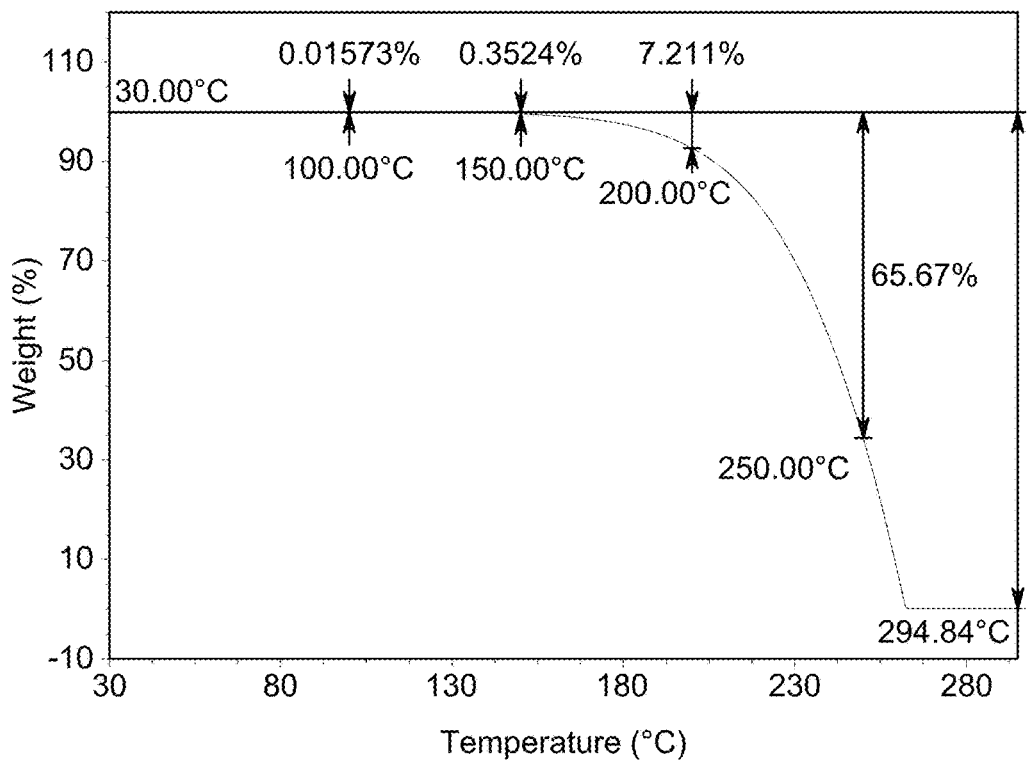
FIG. 5 provides a Thermogravimetric Analysis (TGA) curve of solid Form A.
Figure 6:
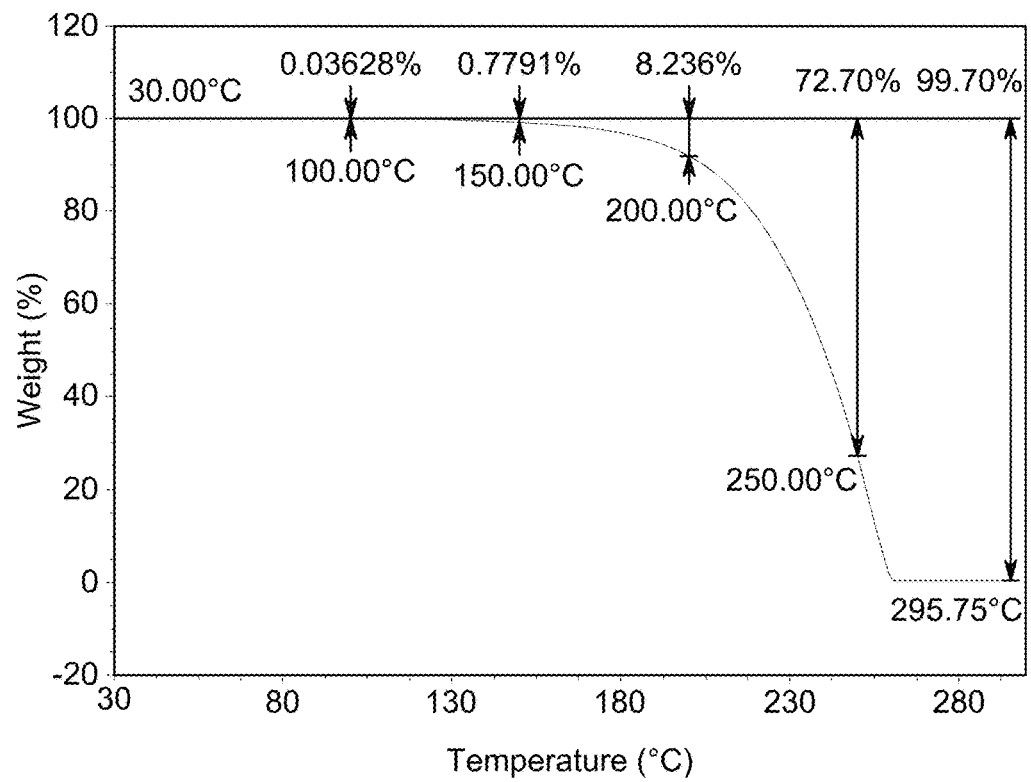
FIG. 6 provides another TGA curve of solid Form A.
Figure 7:
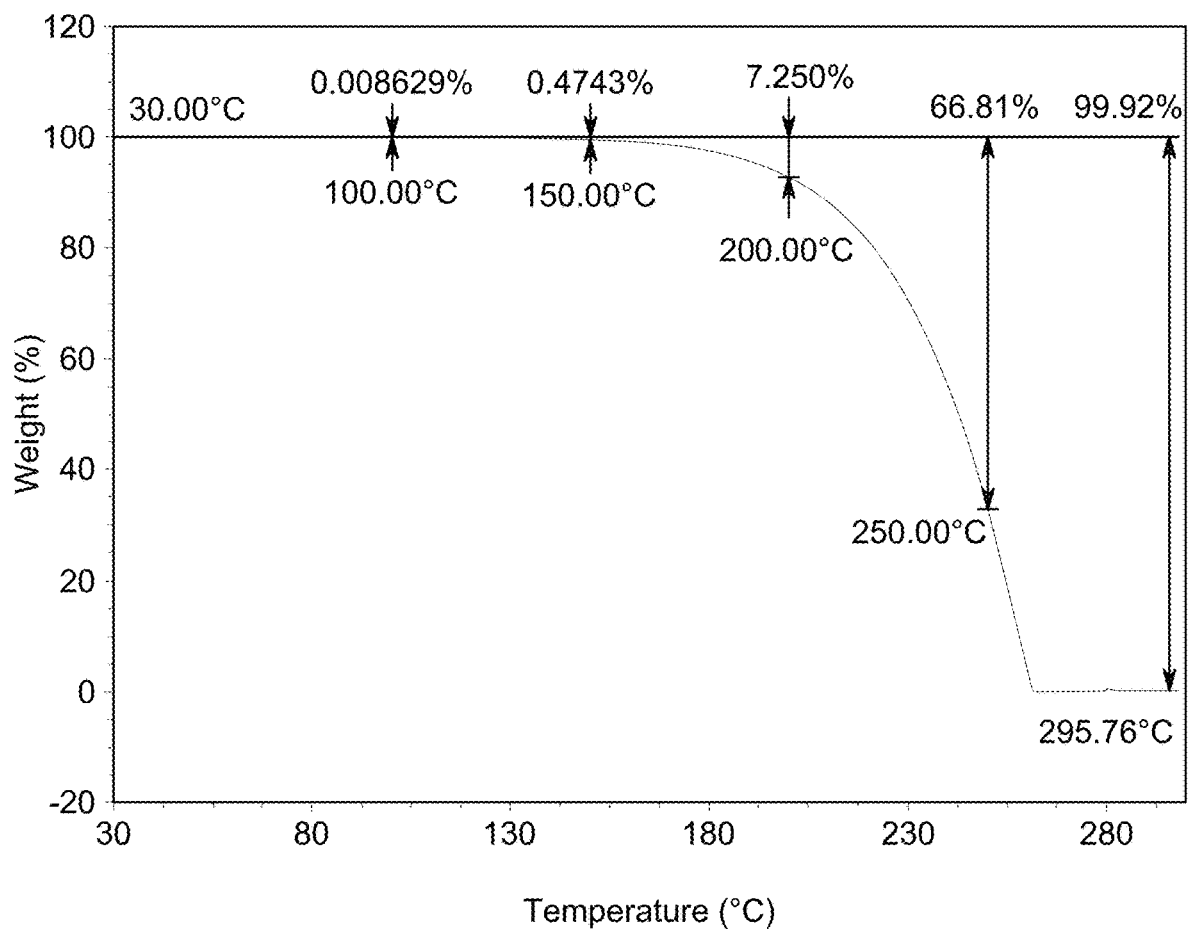
FIG. 7 provides a further TGA curve of solid Form A.

FIG. 2 shows a representative differential scanning calorimeter (DSC) thermogram of Form A. FIG. 3 is another Representative DSC thermogram of Form A, and FIG. 4. is a further representative DSC thermogram of Form A. FIG. 5 shows a representative thermogravimetric analysis (TGA) curve of Form A. FIG. 6 is another representative TGA curve of Form A. FIG. 7 is a further representative TGA curve of Form A.

TABLE 2

DSC and TGA Analysis of Form A

| Entry | Solvent | TGA (weight loss %) | | | | | DSC |
|---|---|---|---|---|---|---|---|
| | | 0° C.-100° C. | 100° C.-150° C. | 150° C.-200° C. | 200° C.-250° C. | 250° C.-300° C. | |
| 1 | Ethanol/Acetic acid (17:1) | 0.02% | 0.035% | 7.21% | 65.67% | — | 119.58 |
| 2 | Methanol | 0.00002% | 0.44% | 8.74% | 74.99% | 99.87% | 116.72 |
| 3 | Ethanol | 0.01% | 0.35% | 6..07% | 70.00% | 99.82% | 116.42 |
| 4 | Acetone | 0.01% | 0.61% | 9.14% | 93.10% | 99.80% | 115.83 |
| 5 | Ethyl methyl Ketone | 0.01% | 0.62% | 8.94% | 79.69% | 99.79% | 115.57 |
| 6 | Methyl isobutyl ketone | 0.03% | 0.70% | 13.22% | 99.72% | 99.76% | 116.09 |
| 7 | Acetonitrile | 0.01% | 0.48% | 9.29% | 85.35% | 99.78% | 116.24 |
| 8 | Propionitrile | 0.004% | 0.51% | 9.05% | 94.02% | 99.81% | 116.23 |
| 9 | Ethyl acetate | 0.0006% | 0.39% | 7.67% | 70.02% | 99.92% | 115.62 |
| 10 | Tetrahydrofuran (THF) | 0.03% | 0.96% | 12.14% | 98.73% | 99.84% | 116.47 |
| 11 | Ethanol/Acetic acid (9:1) | 0.01% | 0.73% | 10.70% | 93.42% | 99.53% | 115.63 |
| 12 | Acetone/Water (9:1) | 0.01% | 0.60% | 10.44% | 95.99% | 99.80% | 116.54 |

TABLE 2-continued

DSC and TGA Analysis of Form A

| Entry | Solvent | TGA (weight loss %) | | | | | DSC |
|---|---|---|---|---|---|---|---|
| | | 0° C.-100° C. | 100° C.-150° C. | 150° C.-200° C. | 200° C.-250° C. | 250° C.-300° C. | |
| 13 | THF/Water (9:1) | 0.04% | 0.78% | 8.24% | 72.70% | 99.70% | 116.35 |
| 14 | 1,4-Dioxane/Water | 0.04% | 0.98% | 8.39% | 77.43% | 99.90% | 115.45 |
| 15 | Methanol/Water (9:1) | 0.01% | 0.47% | 7.25% | 66.81% | 99.92% | 116.50 |
| 16 | Acetonitrile/Water (9:1) | 0.04% | 0.71% | 12.80% | 100.40% | 99.98% | 116.06 |
| 17 | 3-Methyl-1-butanol | 0.18% | 0.89% | 9.74% | 83.52% | 100.30% | 116.06 |
| 18 | 2-Methyl-1-propanol | 0.05% | 1.59% | 23.05% | 100.10% | 100.20% | 115.66 |
| 19 | Isopropanol | 0.01% | 0.46% | 7.39% | 65.74% | 100.80% | 115.65 |
| 20 | Isobutyl acetate | 0.10% | 0.75% | 12.05% | 99.49% | 99.79% | 116.87 |
| 21 | Isopropyl acetate | 0.01% | 0.52% | 9.20% | 83.20% | 99.70% | 115.43 |
| 27 | Toluene | 0.02% | 0.54% | 7.69% | 74.02% | 99.84% | 115.90 |
| 23 | n-Butyl acetate | 0.02% | 0.51% | 7.39% | 64.49% | 99.87% | 116.27 |
| 24 | Dichloromethane (DCM) | 0.03% | 0.83% | 7.69% | 61.29% | 99.980% | 116.03 |
| 25 | Methyl tert-butyl ether | 0.11% | 0.56% | 8.44% | 72.54% | 100.00% | 116.12 |
| 26 | Dimethylsulfoxide (DMSO) | 0.01% | 0.75% | 9.91% | 87.39% | 99.74% | 115.47 |
| 27 | Dimethylformamide (DMF) | 0.14% | 0.92% | 13.29% | 99.82% | 99.87% | 115.25 |
| 28 | Acetic acid | 0.06% | 0.96% | 12.68% | 91.38% | 99.75% | 115.83 |

Form A is stable for at least one year under storage conditions of ambient temperature/75% RH (Relative Humidity), ambient temperature/100% RH, 30° C./75% RH, and 50° C./0% RH.

Mixture of Form A and Form C

Figure 8:
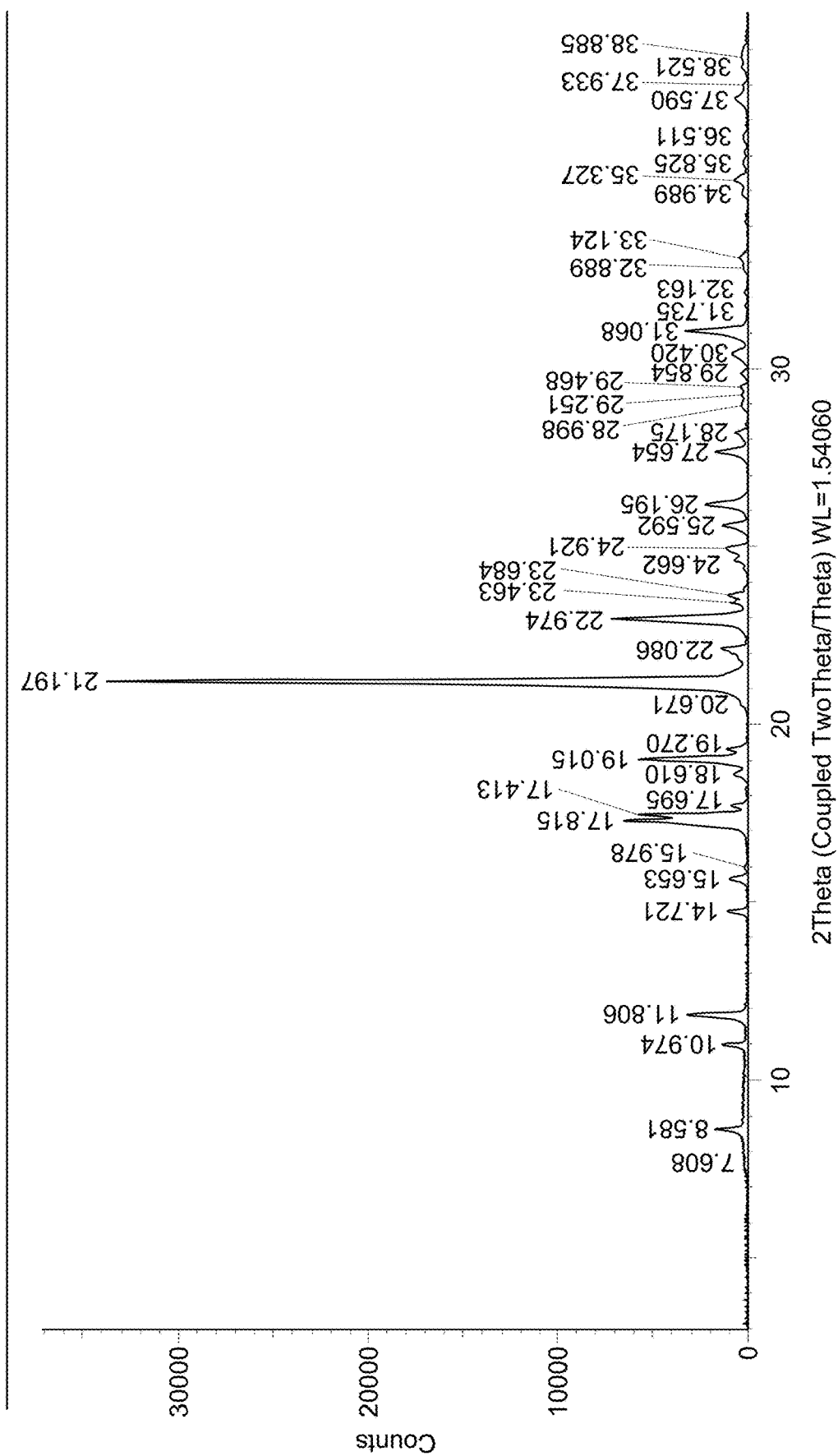
FIG. 8 provides an X-Ray Powder Diffraction (XRPD) pattern of a mixture of solid Form A and solid Form C.

A mixture of Form A and Form C was prepared under conditions described in Table 1. The XRPD pattern of the mixture of Form A and Form C of Compound 1 is depicted in FIG. 8, and the corresponding data is summarized below:

| Degrees 2-Theta | d-spacing (Å) | Relative intensity (%) |
|---|---|---|
| 8.58 | 10.30 | 4.8 |
| 10.97 | 8.06 | 3.9 |
| 11.81 | 7.49 | 9.2 |
| 14.72 | 6.01 | 3.2 |
| 15.65 | 5.66 | 3.1 |
| 17.32 | 5.12 | 18.5 |
| 17.41 | 5.09 | 14.4 |
| 17.70 | 5.00 | 2.5 |
| 18.61 | 4.76 | 2.3 |
| 19.02 | 4.66 | 17.3 |
| 19.27 | 4.60 | 2.7 |
| 21.20 | 4.19 | 100 |
| 22.09 | 4.02 | 3.6 |
| 22.97 | 3.87 | 22.2 |
| 23.60 | 3.77 | 3.1 |
| 24.92 | 3.57 | 3.2 |
| 25.59 | 3.48 | 4.0 |
| 26.20 | 3.40 | 6.9 |
| 27.65 | 3.22 | 5.2 |
| 30.42 | 2.94 | 2.5 |
| 31.07 | 2.88 | 10.2 |
| 35.33 | 2.54 | 2.3 |

Figure 9:
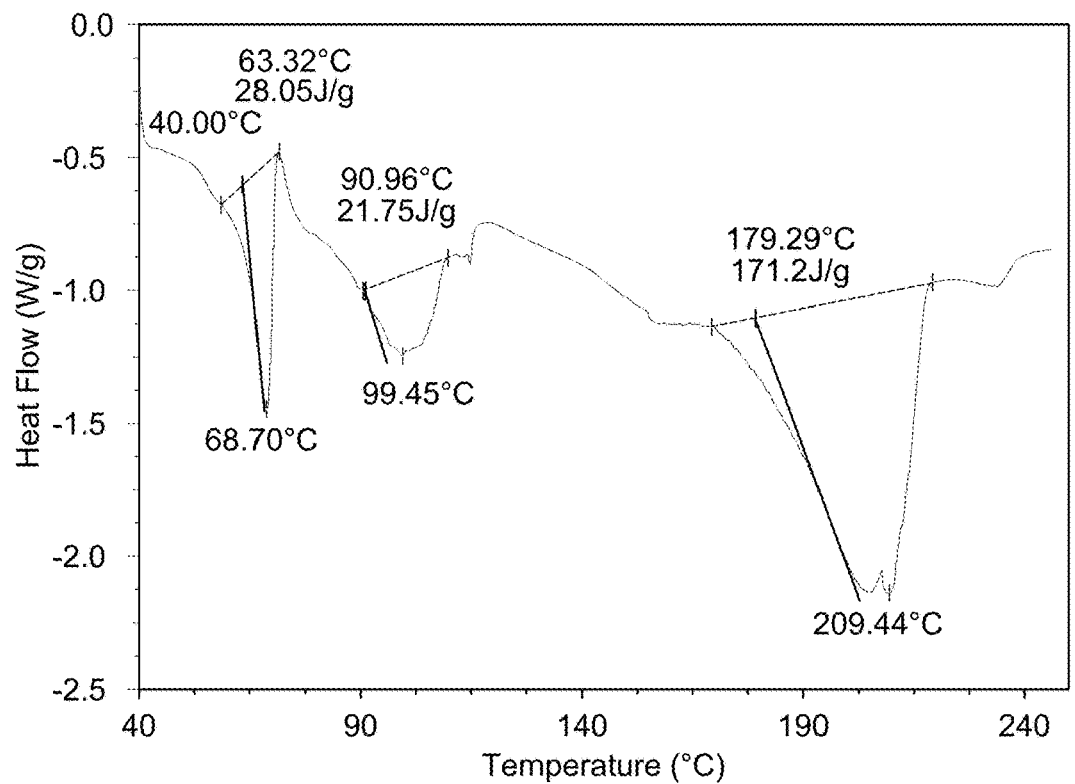
FIG. 9 provides a Differential Scanning Calorimeter (DSC) thermogram of a mixture of solid Form A and solid Form C.
Figure 10:
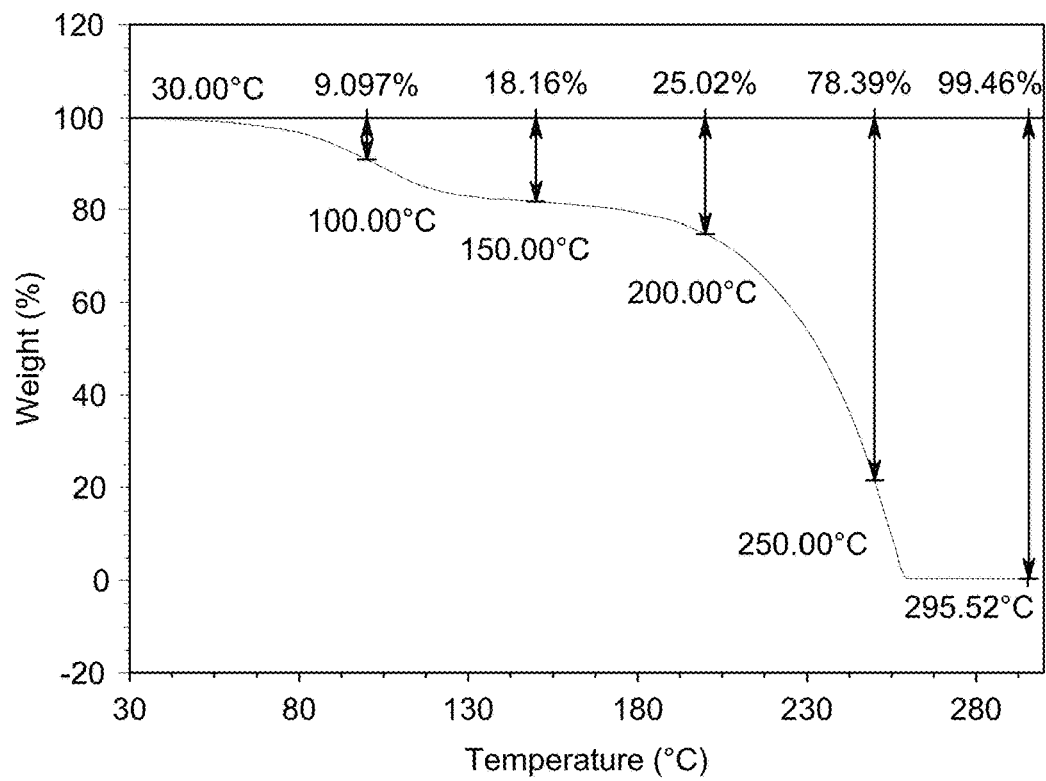
FIG. 10 provides a Thermogravimetric Analysis (TGA) curve of a mixture of solid Form A and solid Form C.

TGA and DSC analysis were performed on a sample of the mixture of Form A and Form C prepared using conditions from Table 1. In DSC, three endotherms were observed at 68.70, 99.45, 209.44 (FIG. 9). As depicted in FIG. 10, the mixture showed in TGA a weight loss of 9.10% from 0° C.-100° C.; 18.16% from 100° C.-150° C.; 25.02% from 150° C.-200° C.; 78.39% from 200° C.-250° C.; and 99.46% from 250° C.-300'C.

Mixture of Form A and Form D

Figure 11:
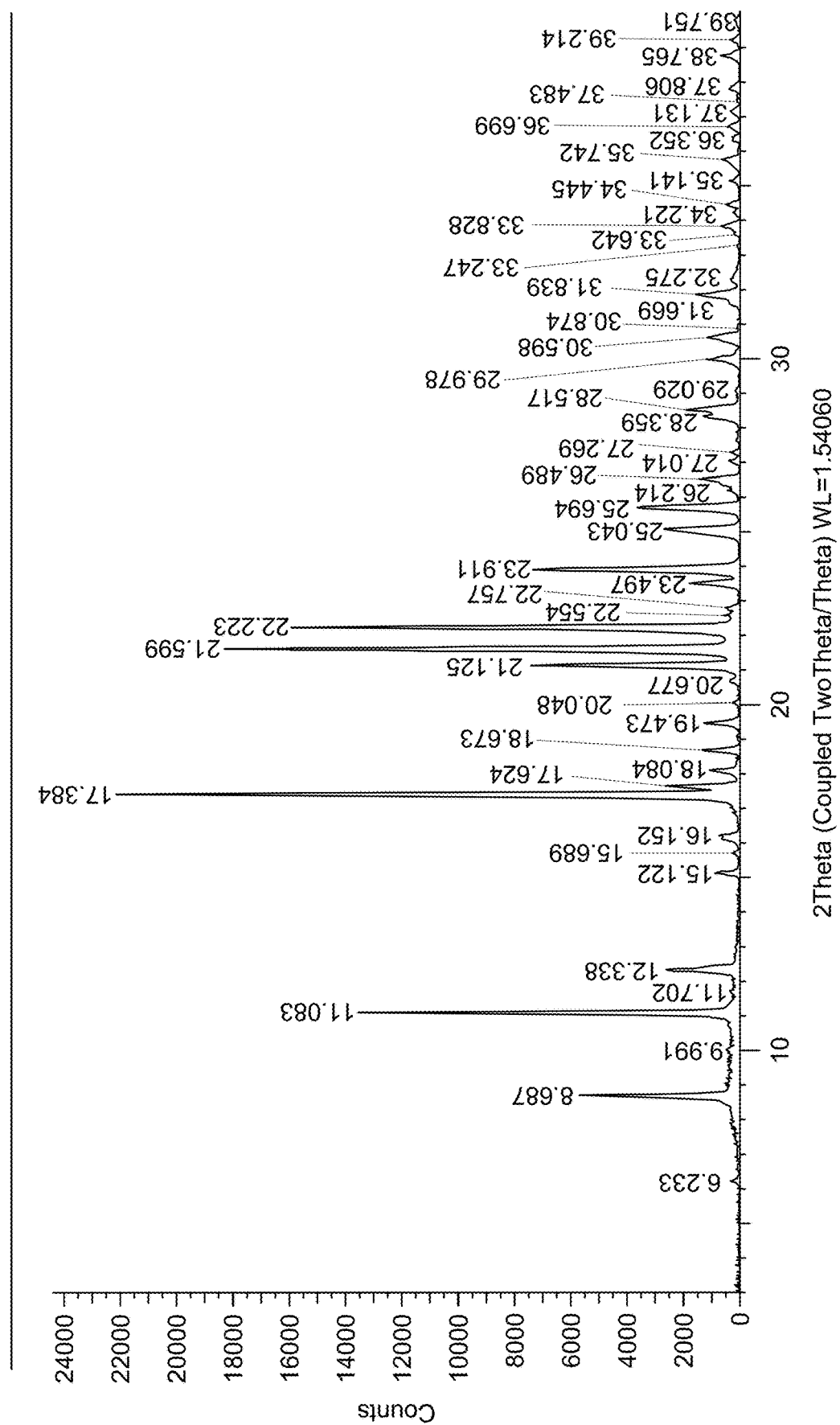
FIG. 11 provides an X-Ray Powder Diffraction (XRPD) pattern of a mixture of solid Form A and solid Form D.

A mixture of Form A and Form D was prepared under conditions described in Table 1. The XRPD pattern of the mixture of Form A and Form D of Compound 1 is depicted in FIG. 11, and the corresponding data is summarized below:

| Degrees 2-Theta | d-spacing (Å) | Relative intensity (%) |
|---|---|---|
| 8.69 | 10.17 | 24.3 |
| 9.99 | 8.85 | 2.0 |
| 11.08 | 7.98 | 60.8 |
| 12.34 | 7.17 | 11.0 |
| 15.12 | 5.85 | 4.1 |
| 16.15 | 5.48 | 2.7 |
| 17.38 | 5.10 | 100 |
| 17.62 | 5.03 | 11.5 |
| 18.08 | 4.90 | 4.9 |
| 18.67 | 4.75 | 6.1 |
| 19.47 | 4.55 | 5.9 |
| 21.13 | 4.20 | 34.3 |
| 21.60 | 4.11 | 84.7 |
| 22.2.2 | 4.00 | 74.5 |
| 22.76 | 3.90 | 2.0 |
| 23.50 | 3.78 | 7.6 |
| 23.91 | 3.72 | 34.4 |
| 25.04 | 3.55 | 11.7 |
| 25.69 | 3.46 | 16.8 |
| 26.49 | 3.36 | 5.5 |
| 28.36 | 3.14 | 5.0 |
| 28.52 | 3.13 | 8.2 |
| 29.98 | 2.98 | 5.5 |
| 30.60 | 2.92 | 5.5 |
| 31.84 | 2.81 | 7.0 |
| 33.83 | 2.65 | 2.6 |
| 34.44 | 2.60 | 2.0 |
| 35.74 | 2.51 | 2.8 |
| 38.77 | 2.32 | 1.0 |

Figure 12:
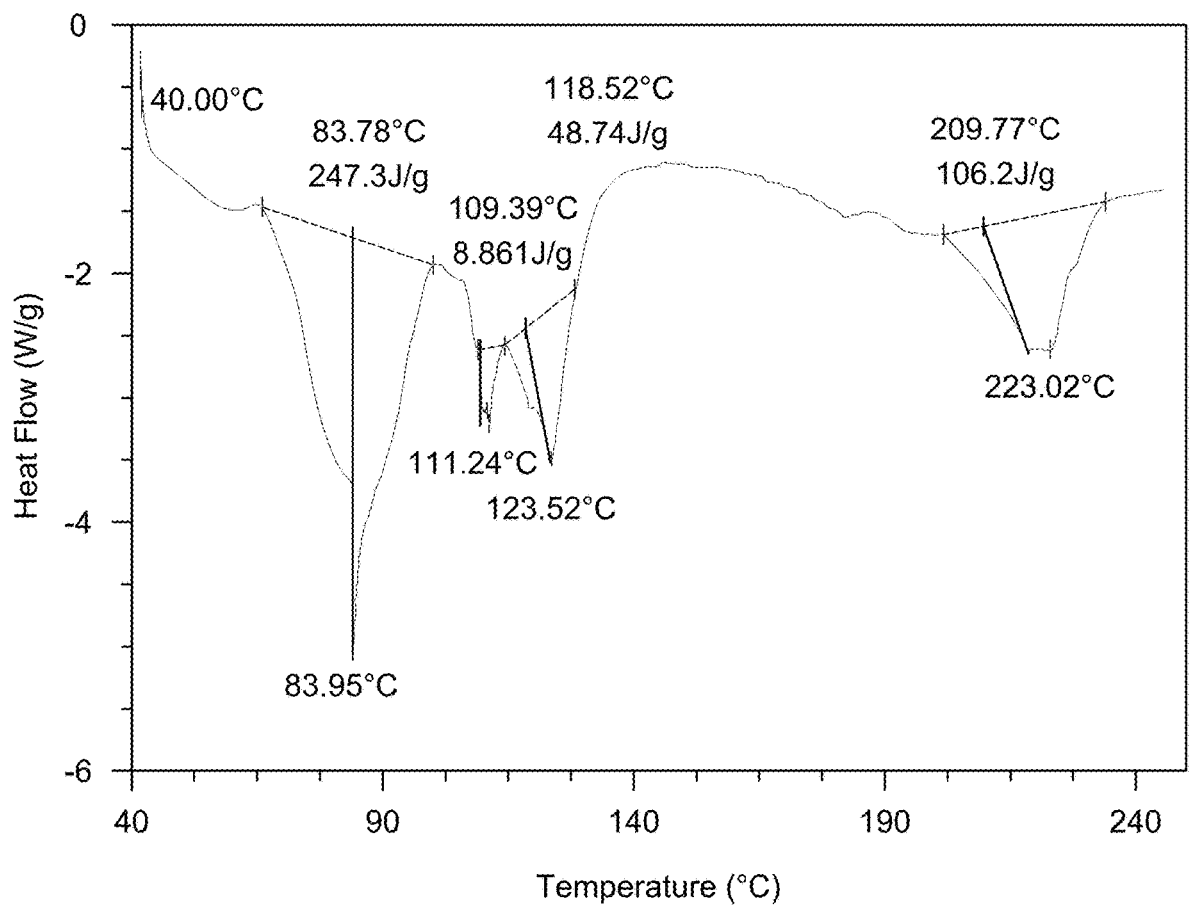
FIG. 12 provides a Differential Scanning Calorimeter (DSC) thermogram of a mixture of solid Form A and solid Form D.
Figure 13:
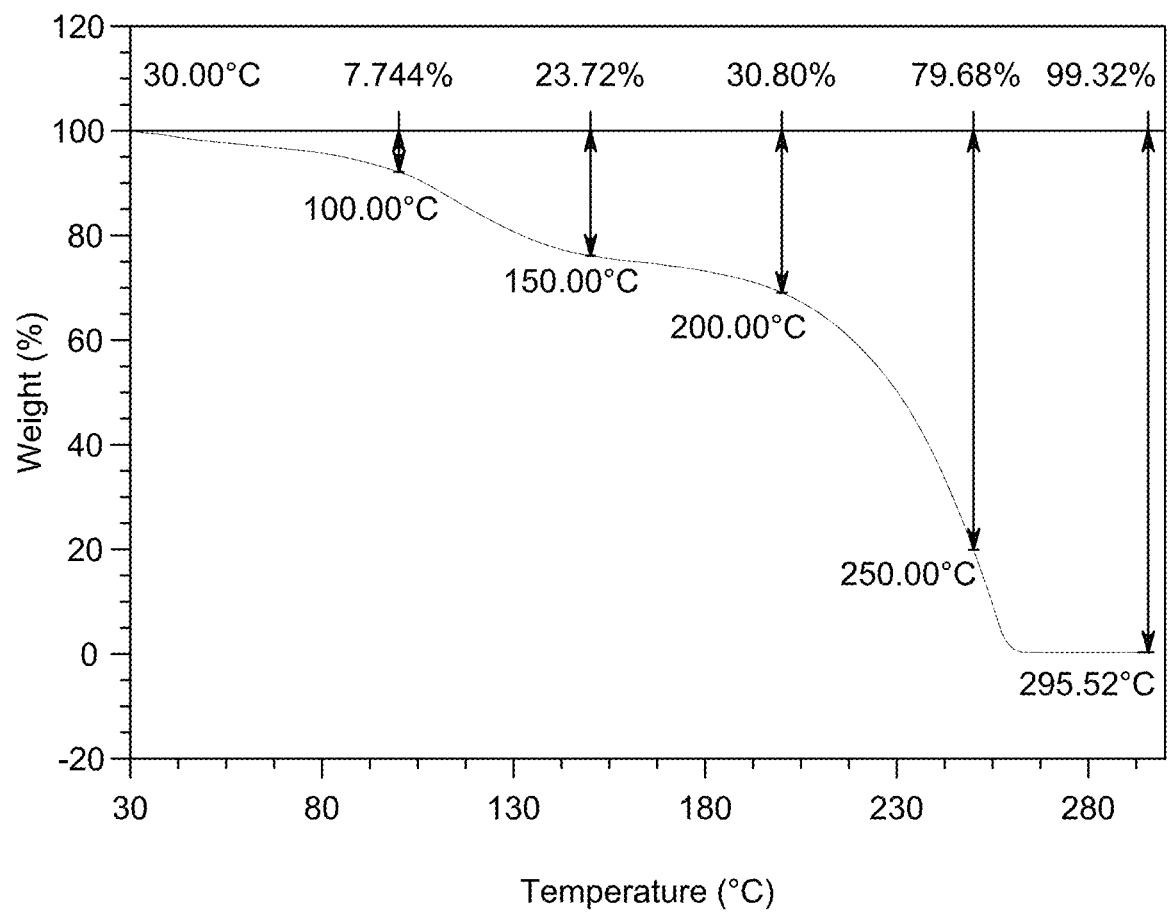
FIG. 13 provides a Thermogravimetric Analysis (TGA) curve of a mixture of solid Form A and solid Form D.

TGA and DSC analysis was performed on a sample of the mixture of Form A and Form D prepared using conditions from Table 1. In DSC, four endotherms were observed at 89.95, 111.24, 123.52, and 223.02° C., respectively (FIG. 12). As depicted in FIG. 13, the mixture showed in TGA a weight loss of 7.74% from 0° C.-100° C.; 23.72% from 100°

C.-150° C.; 30.80% from 150° C.-200° C.; 79.68% from 200° C.-250° C.; and 99.32% from 250° C.-300° C.

Example 4: Scaled-Up Preparation and Characterization of Compound 1 Solid Forms

General Methods:
X-Ray Powder Diffraction (RPD)

XRPD patterns of samples from scaled-up preparations were recorded at ambient temperature on a Bruker D8 Advance X-ray diffractometer (Karlsruhe, Germany) using Cu Kα radiation (λ=1.54 Å) at 40 kV, 40 mA passing through a Vario monochromator (Karlsruhe, Germany). The sample was loaded on a zero-background holder and gently pressed by a clean glass slide to ensure co-planarity of the powder surface with the surface of the holder. Data were collected in a continuous scan mode with a step size of 0.05 and dwell time of 1 s over an angular range of 3° to 40° 2θ. Obtained diffractograms were analyzed with DIF-FRAC.EVA diffraction software (Bruker, Wis., USA).

In some cases, the X-ray intensity data were measured on a Bruker D8 Eco diffractometer system equipped with a graphite monochromator and a Cu Kα Sealed tube (λ=1.54 Å). The sample was loaded in a polyimide capillaries and collected data in transmission mode. Bruker's APEX3 software suite (Bruker, Wis., USA) was used to collect and extract the intensity data. Obtained diffractograms were analyzed with TOPAS software (Bruker, Wis., USA).

Mercury 4.2.0 software (Build 257471, Cambridge Crystallographic Data Centre, UK) was used to calculate the XRPD patterns from single crystal data.
Thermogravimetric Analysis (TGA)

TGA was performed using a Discovery TGA 5500 (TA® Instruments, New Castle, Del., USA) instrument operating with TRIOS software (Version 5.0). The sample was placed in an aluminum pan. The sample cell was purged with dry nitrogen at a flow rate of 15 mL/min. A heating rate of 10° C./min from 25° C. to desired temperature was used in all the experiments.
Differential Scanning Calorimetry (DSC)

Figure 14:
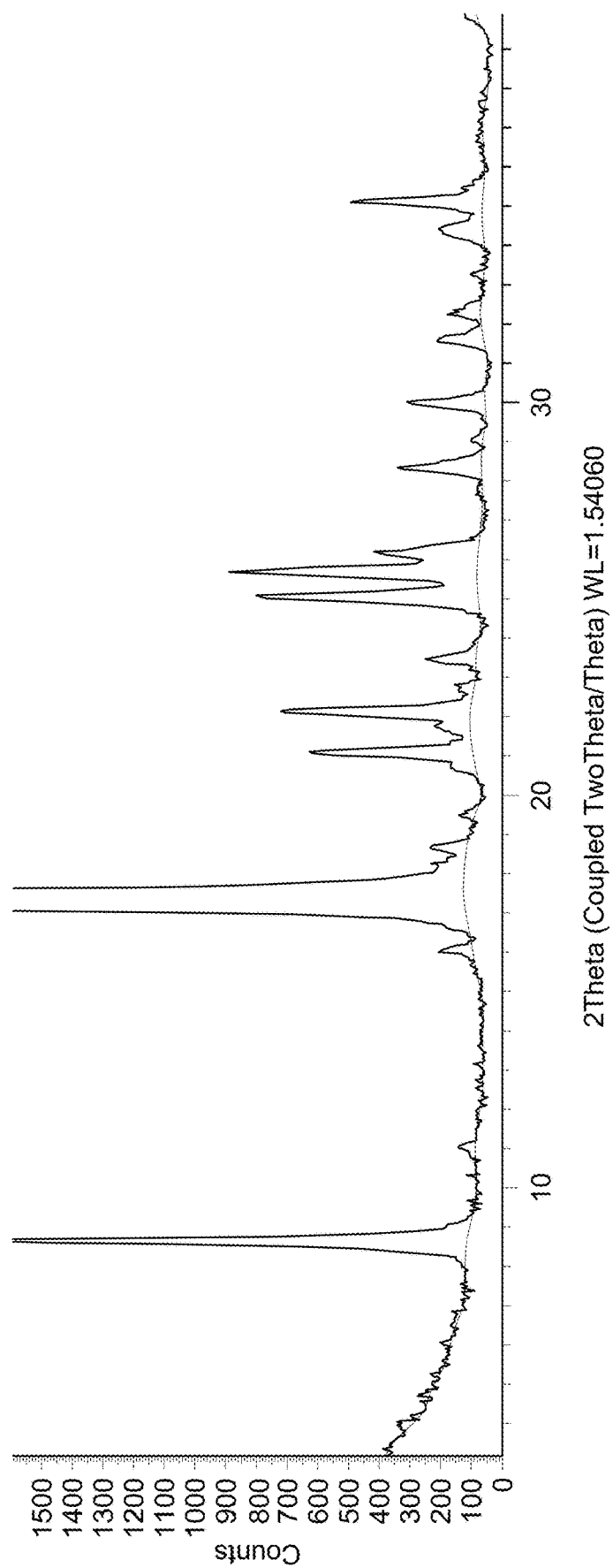
FIG. 14 provides XRPD pattern of Compound 1 Lot I.
Figure 15:
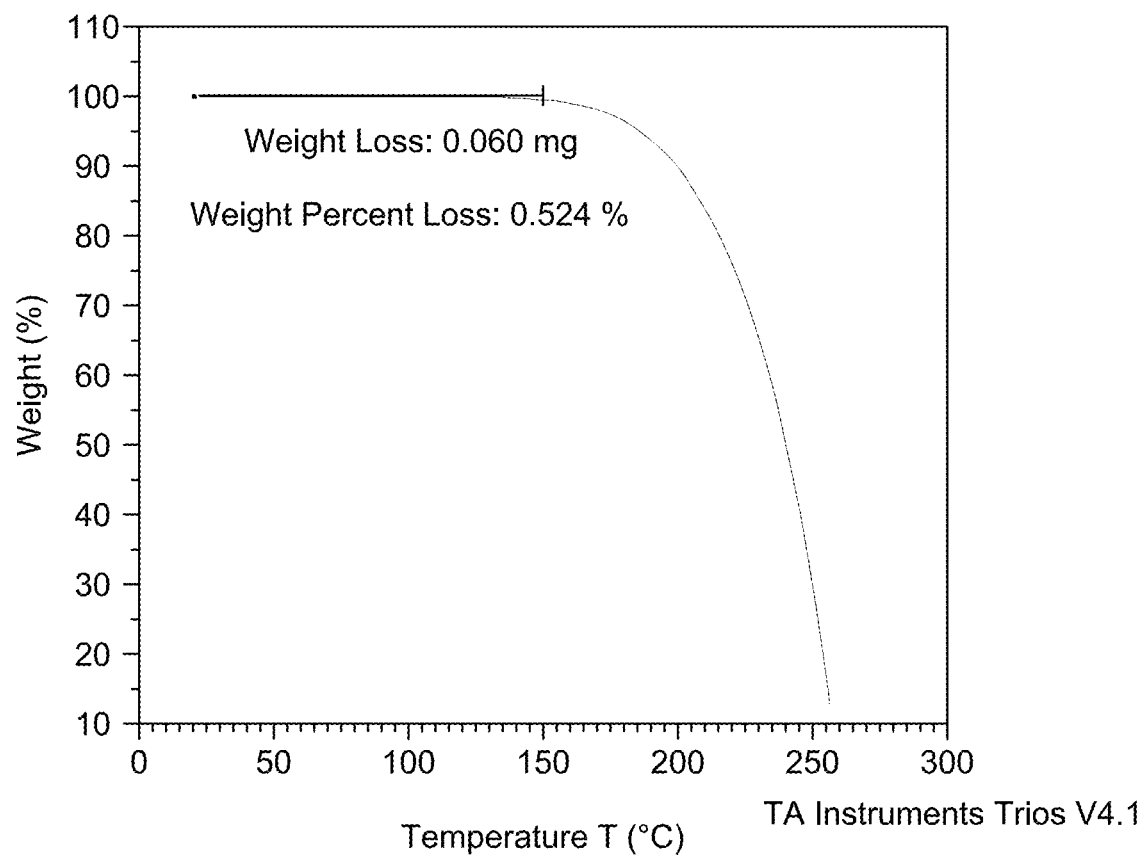
FIG. 15 provides TGA curve of Compound 1 Lot I.
Figure 16:
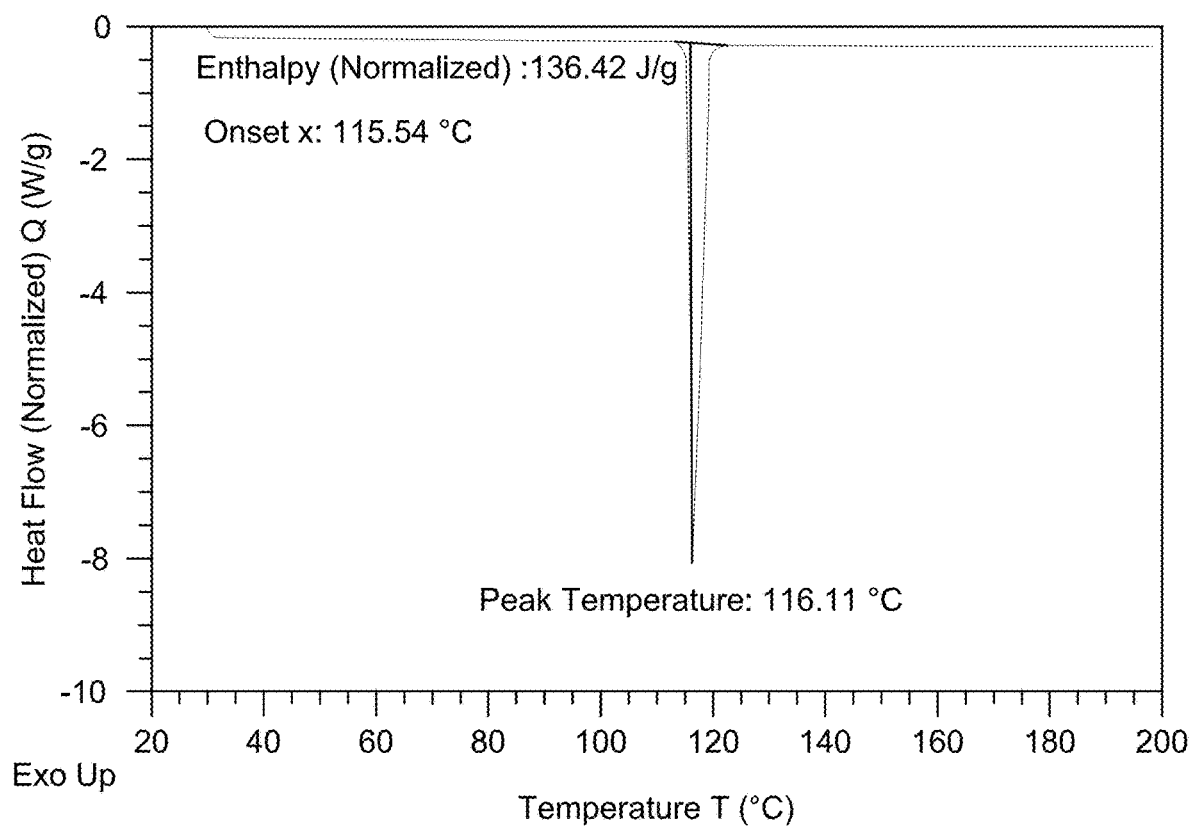
FIG. 16 provides DSC thermogram of Compound 1 Lot I.

Conventional DSC experiments were performed using a Discovery DSC 250 (TA® Instruments, New Castle, Del., USA) instrument equipped with a refrigerated cooling system (RCS90) and operating with TRIOS software (Version 5.0). The sample cell was purged with dry nitrogen at a flow rate of 50 mL/min. Accurately weighed samples (2-5 mg) placed in TZero pans with a pin hole were scanned at a heating rate of 10° C./min over a temperature range of 25° C. to desired temperature was used in all the experiments
Compound 1 Lot I Compound 1 was provided in a form with an XRPD as shown in FIG. 14, a TGA as shown in FIG. 15, and a DSC as shown in FIG. 16. Herein, this material is referred to as "Compound 1 Lot I."
Form A Compound 1 Form A was synthesized by recrystallizing Compound 1 Lot I from methanol. In a typical reaction, ~450 mg of Compound 1 Lot I was dissolved in 2 mL of methanol while heating at 50° C. Resultant solution was kept at room temperature and allowed for slow evaporation of the solvent. Crystals suitable for single crystal X-ray diffraction were obtained within one day.

Compound 1 Form A bulk powder was prepared as follows: ~5 g of Compound 1 Lot I was suspended in 5 mL of methanol and slurried at room temperature for two days. The resulting solid was filtered using 0.45 μm PTFE syringe filter.

Figure 42A:
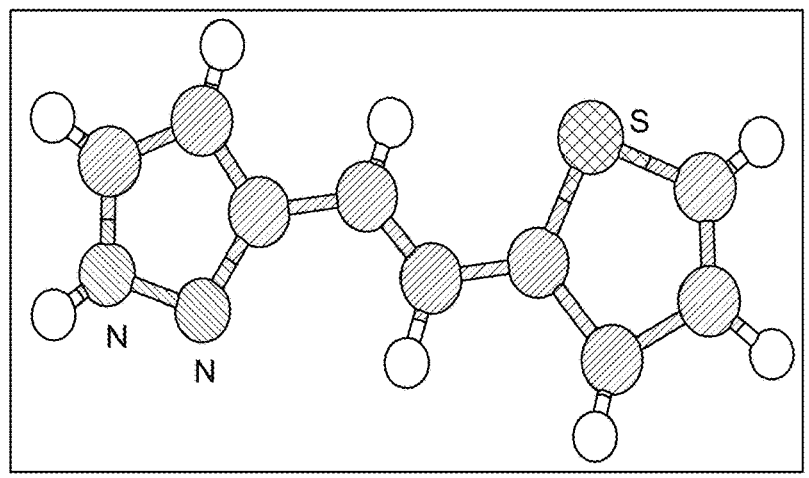
FIG. 42A provides single crystal X-ray crystallography of Compound 1 Form A. N and S atoms are labeled; unlabeled non-hydrogen atoms are carbon.

Single crystal X-ray diffraction of Compound 1 Form A was obtained (FIG. 42A). Crystal data and structure refinement parameters are summarized below:

| | |
|---|---|
| Temperature (K) | 278.15 |
| Crystal system | Monoclinic |
| Space group | C2/c |
| a (Å) | 2.5572(10) |
| b (Å) | 4.9949(2) |
| c (Å) | 16.8890(8) |
| α (°) | 90 |
| β (°) | 108.445(2) |
| γ (°) | 90 |
| Volume (Å$^3$) | 1725.12(14) |

Figure 17:
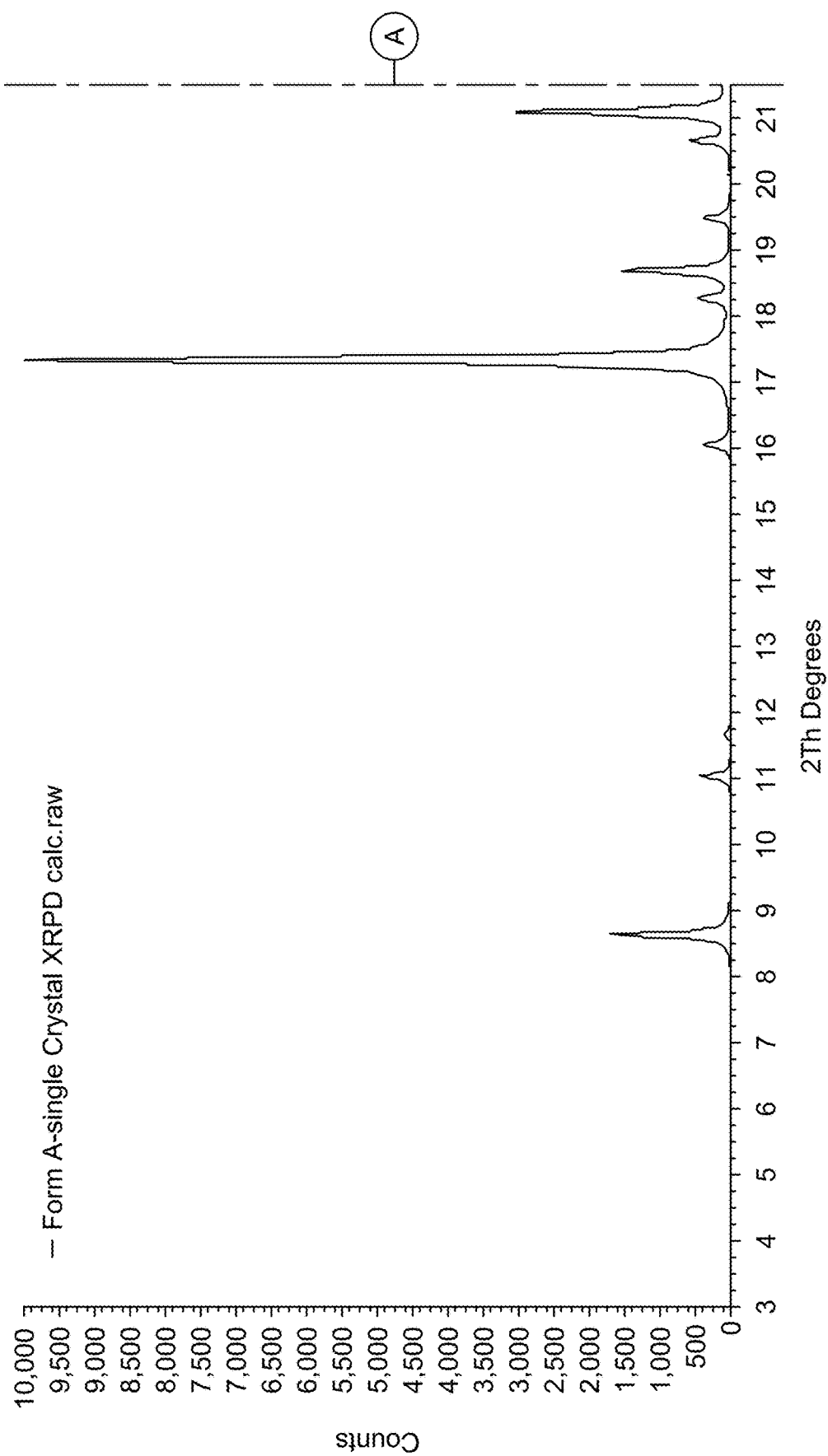
FIG. 17 provides XRPD pattern of Compound 1 Form A calculated from single crystal X-ray diffraction data.
Figure 17:
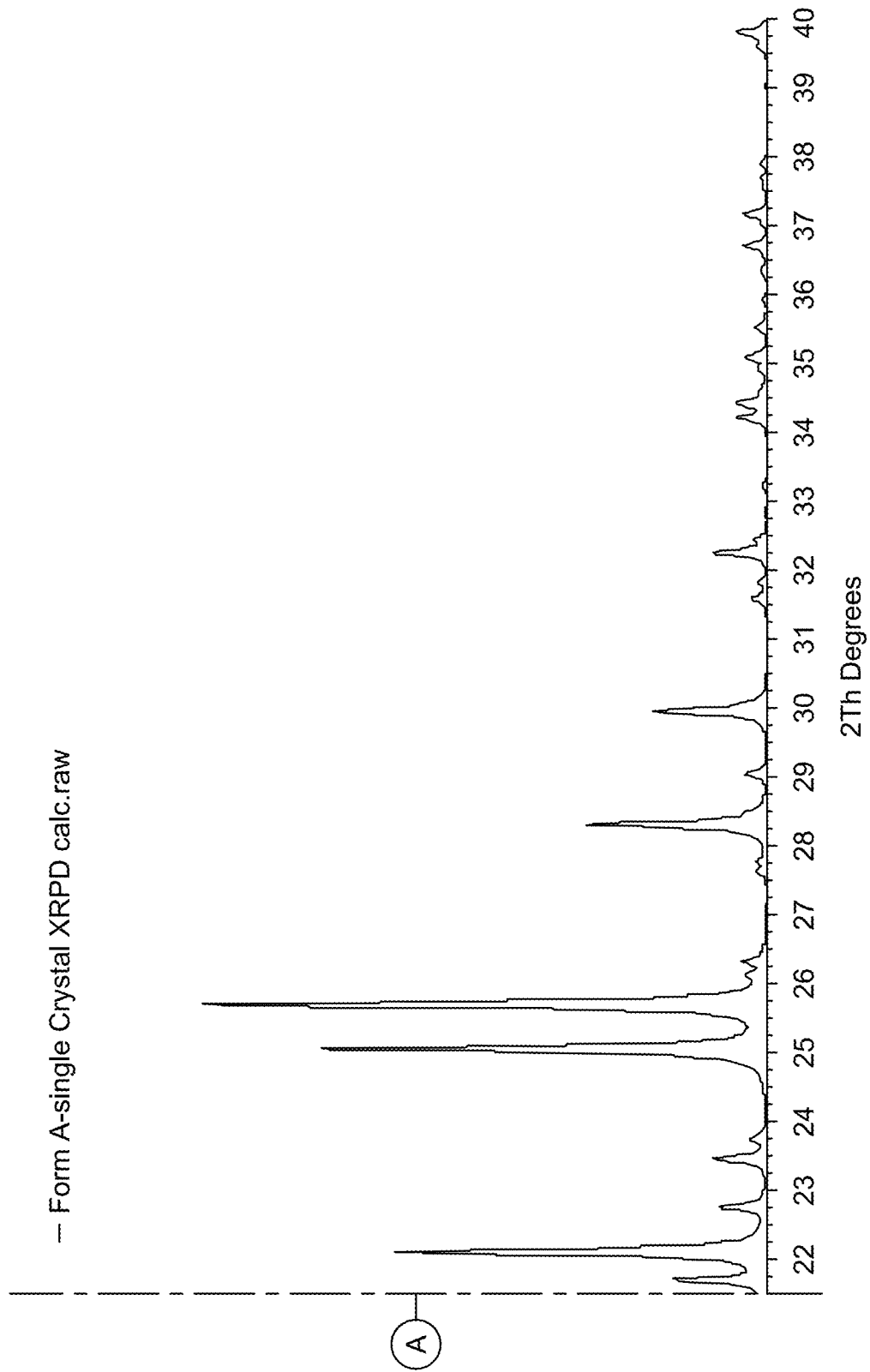

The XRPD pattern of Compound 1 Form A calculated from single crystal X-ray diffraction data is shown in FIG. 17 and is summarized below:

| 2θ (°) | d-spacing (Å) | Intensity Counts (I) |
|---|---|---|
| 8.64 | 10.22 | 1690 |
| 11.04 | 8.01 | 422.5 |
| 11.67 | 7.57 | 88.3 |
| 16.06 | 5.51 | 380.0 |
| 17.34 | 5.11 | 9972 |
| 18.27 | 4.85 | 464.7 |
| 18.69 | 4.74 | 1532 |
| 19.49 | 4.55 | 387.5 |
| 20.66 | 4.30 | 587.9 |
| 21.09 | 4.21 | 3023 |
| 21.70 | 4.09 | 1257 |
| 22.10 | 4.02 | 5053 |
| 22.76 | 3.90 | 636.7 |
| 23.46 | 3.79 | 723.6 |
| 23.74 | 3.74 | 238.5 |
| 25.06 | 3.55 | 6064 |
| 25.70 | 3.46 | 7656 |
| 26.12 | 3.41 | 301.6 |
| 26.32 | 3.38 | 352.7 |
| 27.64 | 3.23 | 147.8 |
| 27.78 | 3.21 | 140.2 |
| 28.31 | 3.15 | 2450 |
| 28.49 | 3.13 | 300.2 |
| 29.04 | 3.07 | 293.7 |
| 29.95 | 2.98 | 1525 |
| 31.59 | 2.83 | 197.4 |
| 31.82 | 2.81 | 125.7 |
| 32.25 | 2.77 | 707.3 |
| 33.22 | 2.69 | 71.4 |
| 34.21 | 2.62 | 391.5 |
| 34.42 | 2.60 | 415.4 |
| 35.08 | 2.56 | 791.9 |
| 35.53 | 2.52 | 173.3 |
| 36.33 | 2.47 | 100.8 |
| 36.70 | 2.45 | 316.9 |
| 37.16 | 2.42 | 309.8 |
| 37.65 | 2.39 | 53.2 |
| 39.02 | 2.31 | 22.1 |
| 39.60 | 2.27 | 156.6 |
| 39.81 | 2.26 | 392.5 |

Figure 18:
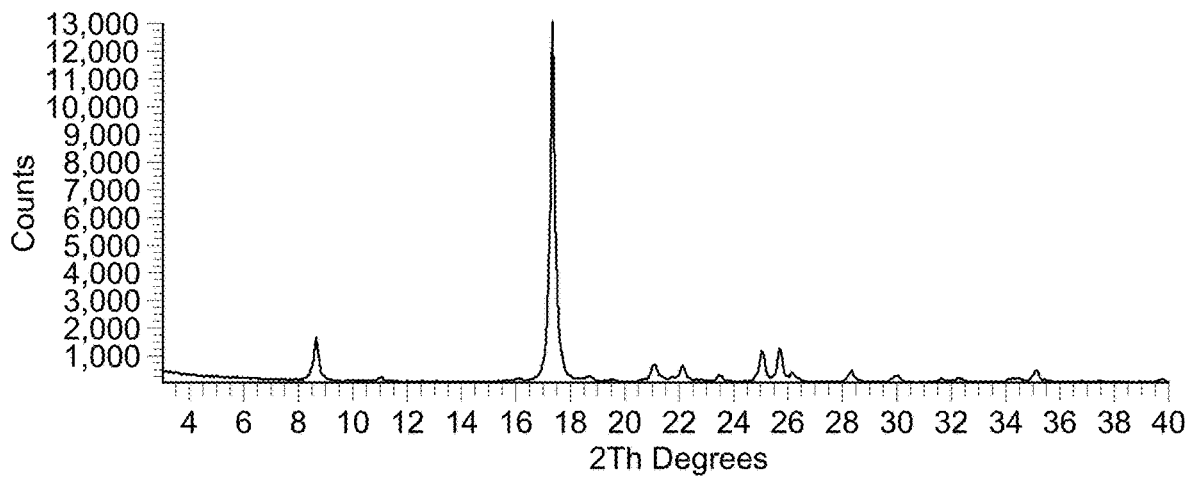
FIG. 18 provides XRPD pattern of Compound 1 Form A.

The XRPD pattern of Compound 1 Form A bulk powder is shown in FIG. 18. Comparison of observed XRPD pattern of Compound 1 Form A bulk powder corresponds well with the calculated XRPD pattern (FIG. 17).

Figure 19:
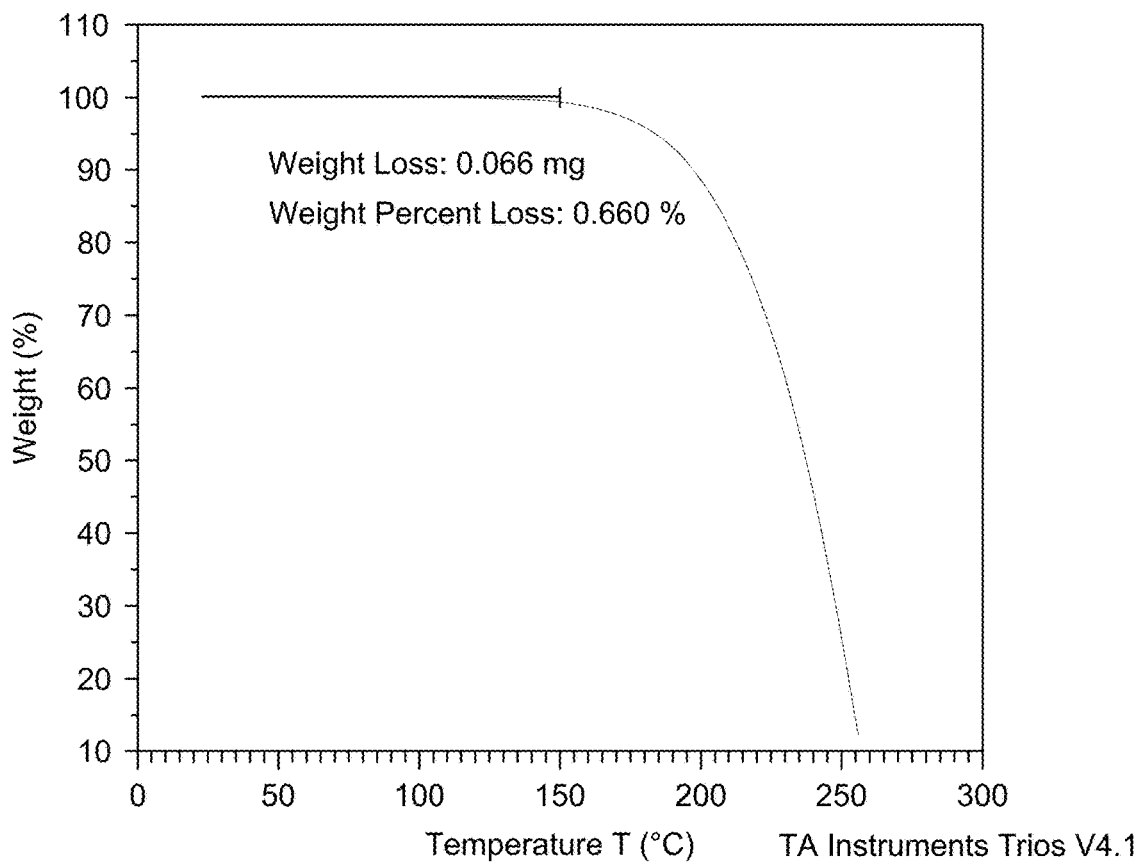
FIG. 19 provides TGA curve of Compound 1 Form A.

TGA of Compound 1 Form A is shown in FIG. 19. A weight loss of 0.6% was observed up to 150° C.

Figure 20:
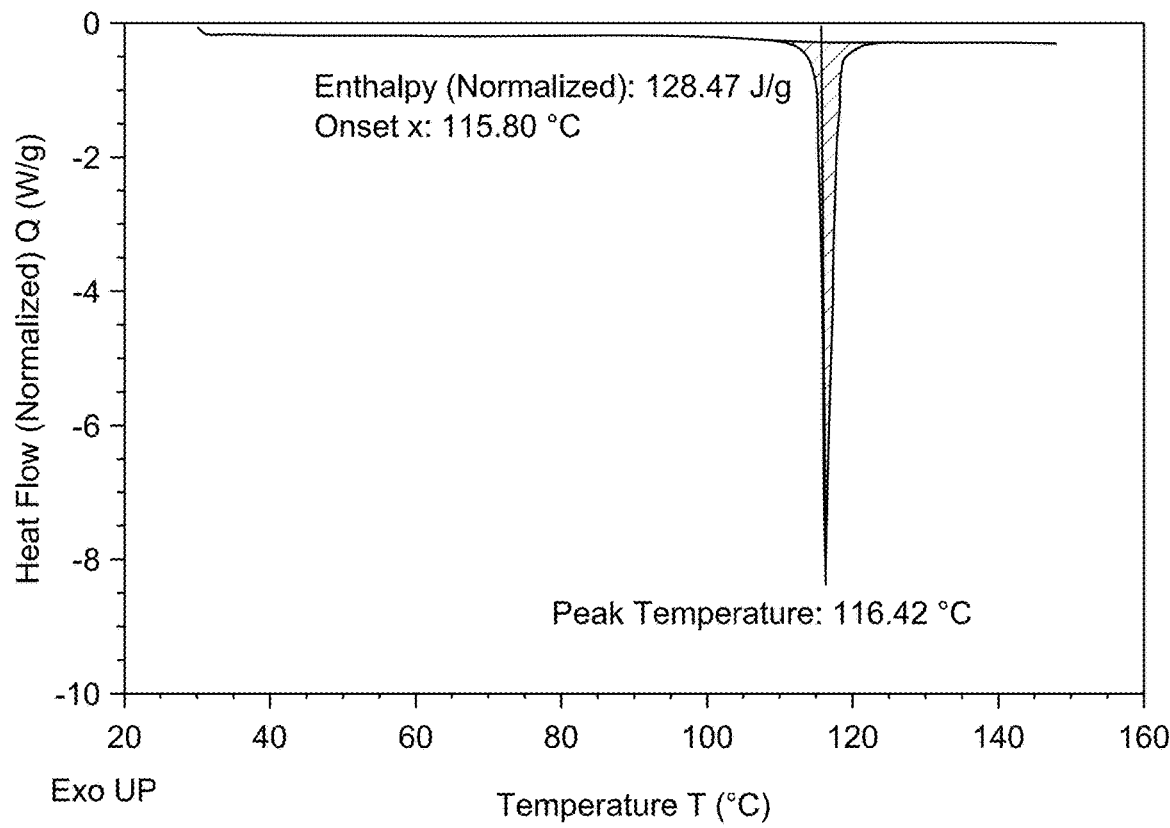
FIG. 20 provides DSC thermogram of Compound 1 Form A.

DSC of Compound 1 Form A is shown in FIG. 20. One endotherm was observed at 116.42° C.

Figure 21:
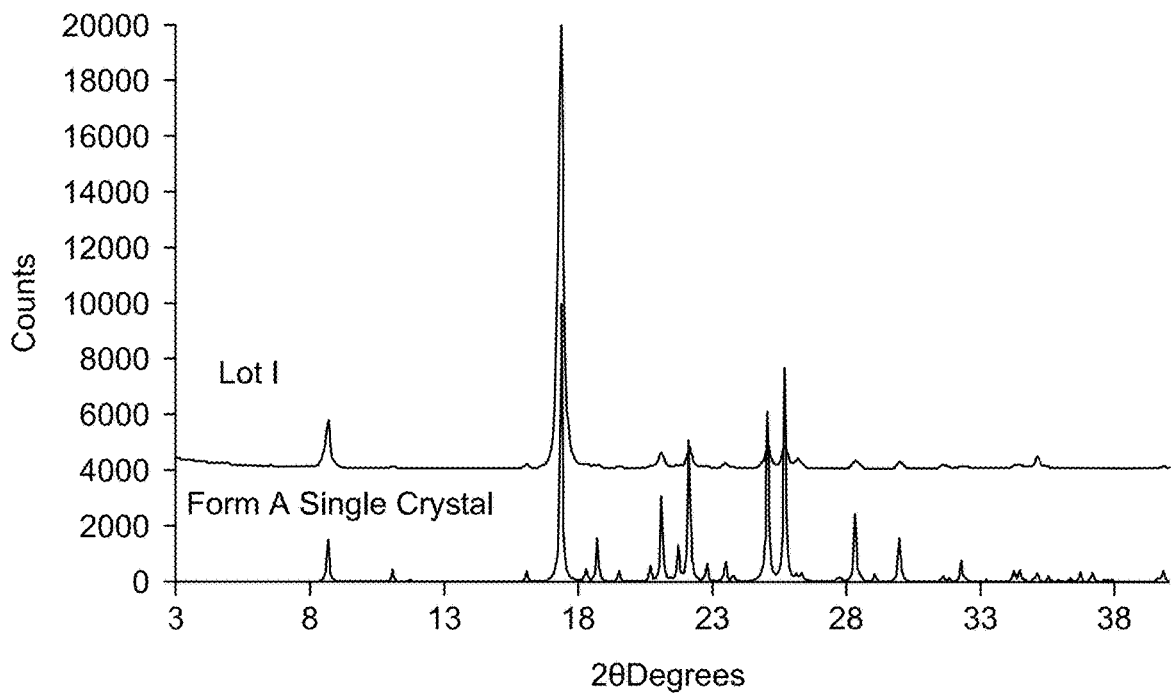
FIG. 21 provides a comparison of XRPD patterns of Compound 1 Lot I and Compound 1 Form A.

A comparison of Compound 1 Lot I is shown in FIG. 21 and verifies that Compound 1 Lot I matches Form A.
Form C Compound 1 Form C was prepared as follows: ~500 mg of Compound 1 Lot I was dissolved in a solvent mixture (250 µl of propylene glycol and 1500 µl of methyl isobutyl ketone) while heating at 50° C. The resultant solution was kept at −27° C. for 48 hours to yield Compound 1 Form C. Solids were collected by filtration using 0.45 µm PTFE syringe filter.

Figure 42B:
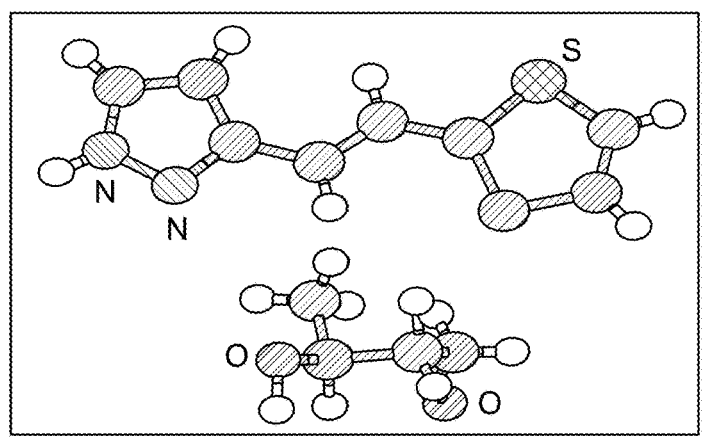
FIG. 42B provides single crystal X-ray crystallography of Compound 1 Form C. N, S, and O atoms are labeled; unlabeled non-hydrogen atoms are carbon.

Single crystal X-ray diffraction of Compound 1 Form C was obtained and showed that Compound 1 Form C is a propylene glycol solvate (2:1 Compound 1:propylene glycol) (FIG. 42B). Crystal data and structure refinement parameters are summarized below:

| | |
|---|---|
| Temperature (K) | 278.15 |
| Crystal system | Orthorhombic |
| Space group | Pbcn |
| a (Å) | 28.481(4) |
| b (Å) | 7.7056(9) |
| c (Å) | 10.1243(13) |
| α (°) | 90 |
| β (°) | 90 |
| γ (°) | 90 |
| Volume (Å$^3$) | 2221.9(5) |

Figure 22:
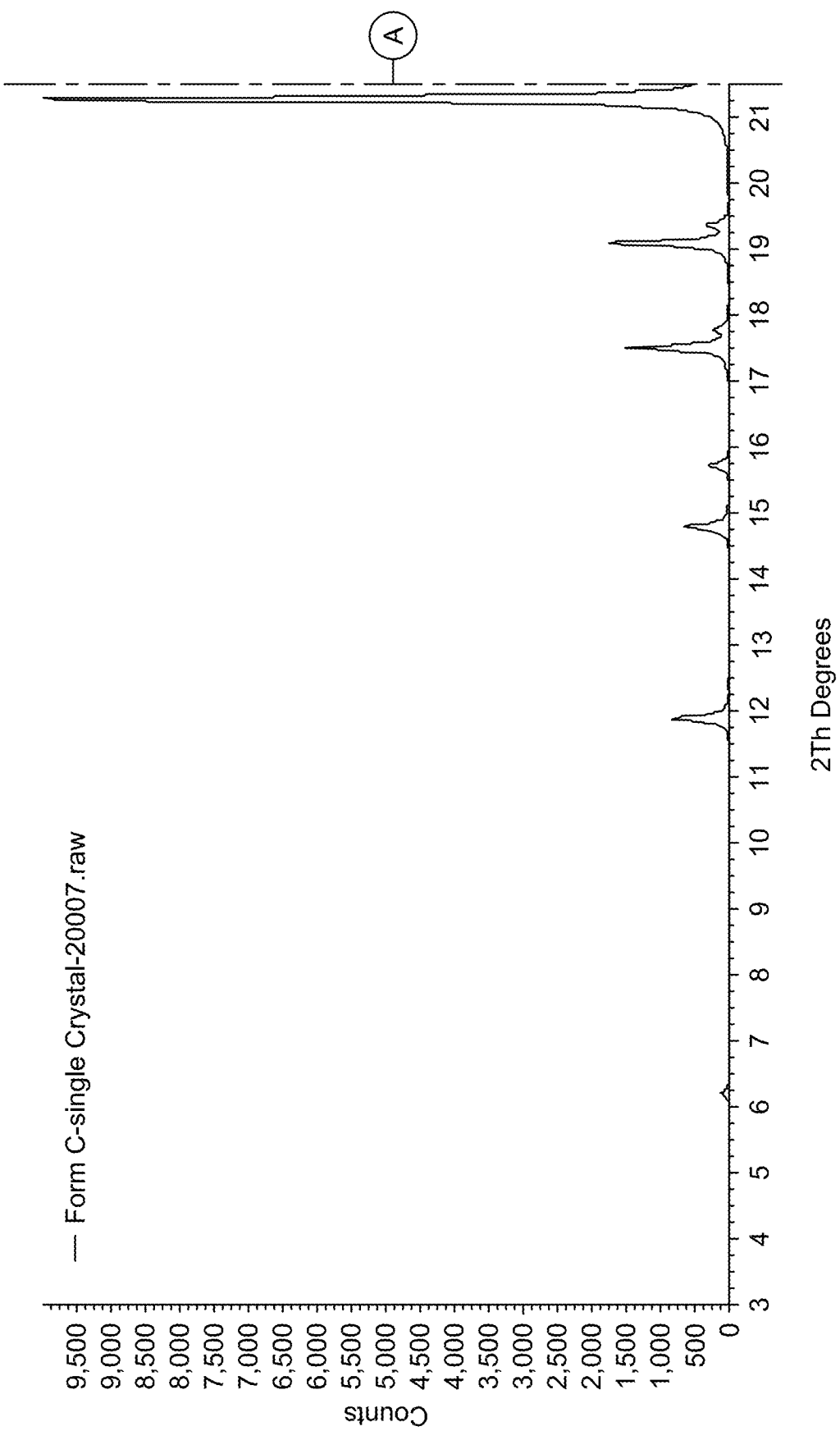
FIG. 22 provides XRPD pattern of Compound 1 Form C calculated from single crystal X-ray diffraction data.
Figure 22:
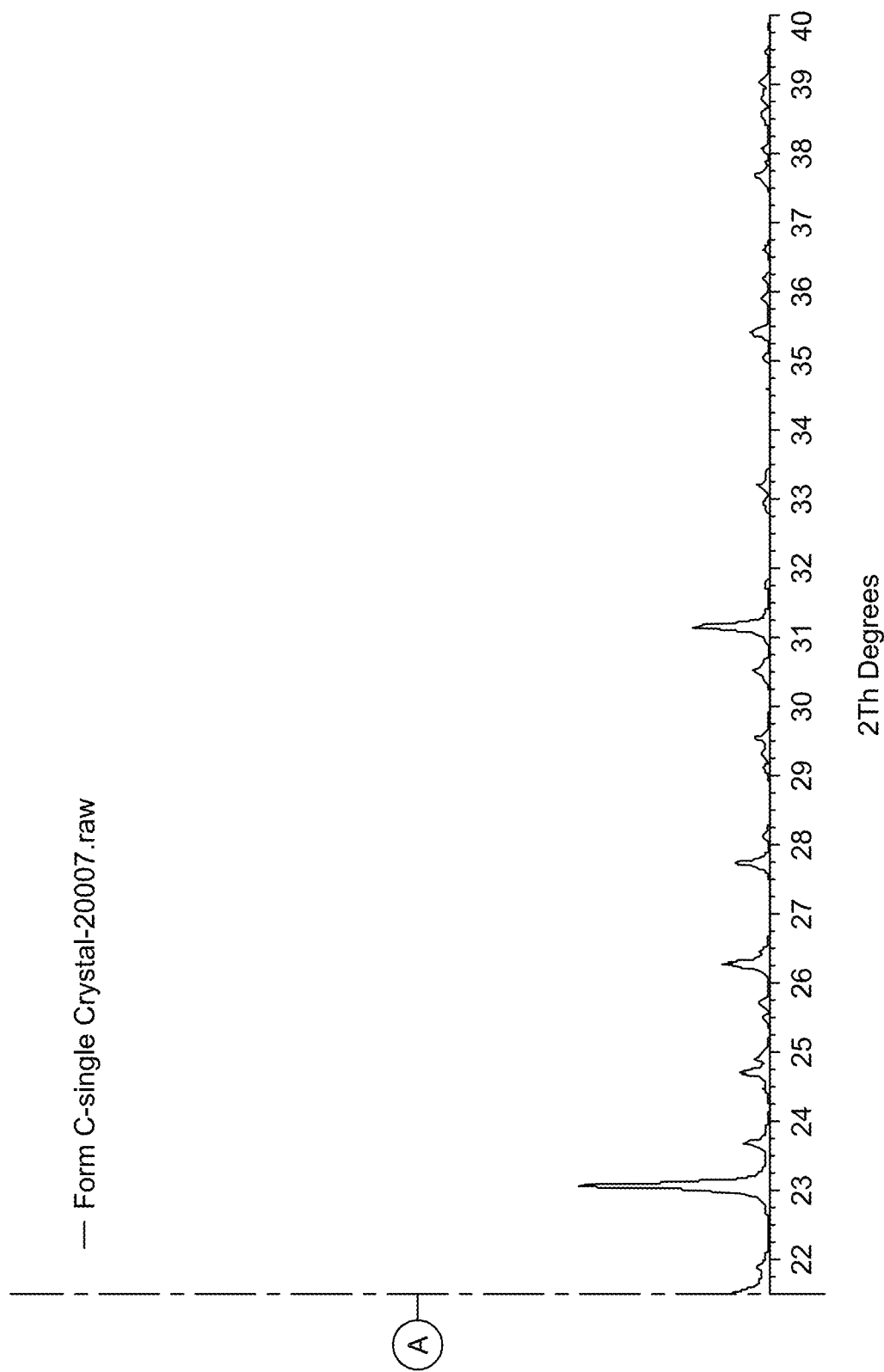

The XRPD pattern of Compound 1 Form C calculated from single crystal X-ray diffraction data is shown in FIG. 22 and is summarized below:

| 2θ (°) | d-spacing (Å) | Intensity Counts (I) |
|---|---|---|
| 6.20 | 14.24 | 115.6 |
| 11.88 | 7.44 | 816.6 |
| 12.41 | 7.13 | 31.7 |
| 14.79 | 5.99 | 645.4 |
| 15.72 | 5.63 | 294.4 |
| 17.50 | 5.06 | 1490 |
| 17.78 | 4.98 | 226.8 |
| 19.08 | 4.65 | 1725 |
| 19.36 | 4.58 | 327.8 |
| 21.28 | 4.17 | 10000 |
| 21.89 | 4.06 | 178.0 |
| 23.07 | 3.85 | 2644 |
| 23.69 | 3.75 | 338.2 |
| 23.92 | 3.72 | 68.5 |
| 24.70 | 3.60 | 418.4 |
| 24.90 | 3.57 | 191.4 |
| 25.50 | 3.49 | 96.2 |
| 25.71 | 3.46 | 154.9 |
| 26.28 | 3.39 | 646.2 |
| 27.74 | 3.21 | 464.2 |
| 28.13 | 3.17 | 81.9 |
| 29.10 | 3.07 | 81.6 |
| 29.31 | 3.04 | 132.3 |
| 29.55 | 3.02 | 209.9 |
| 30.51 | 2.93 | 215.7 |
| 31.15 | 2.87 | 1058 |
| 31.76 | 2.82 | 67.2 |
| 32.93 | 2.72 | 93.6 |
| 33.19 | 2.70 | 163.7 |
| 33.36 | 2.68 | 70.1 |
| 34.63 | 2.59 | 12.8 |
| 35.05 | 2.56 | 93.6 |
| 35.40 | 2.53 | 274.8 |
| 35.90 | 2.50 | 112.6 |
| 36.20 | 2.48 | 77.1 |
| 36.60 | 2.45 | 78.3 |
| 37.57 | 2.39 | 105.6 |
| 37.69 | 2.38 | 214.3 |
| 38.05 | 2.36 | 105.1 |
| 38.54 | 2.33 | 127.0 |
| 38.80 | 2.32 | 124.8 |
| 39.05 | 2.30 | 155.2 |
| 39.46 | 2.28 | 50.0 |
| 39.82 | 2.26 | 34.2 |

Figure 23:
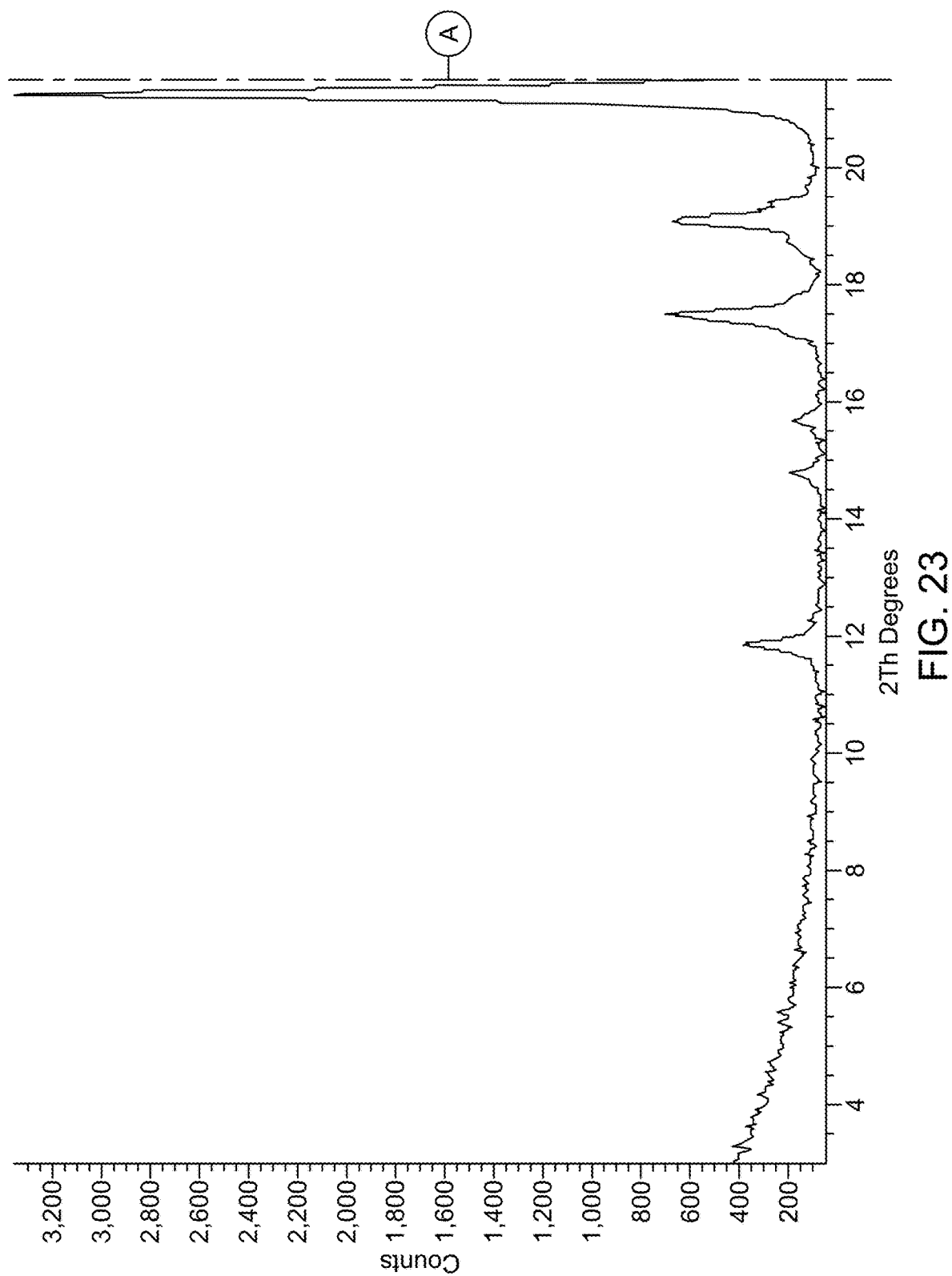
FIG. 23 provides XRPD pattern of Compound 1 Form C.
Figure 23:
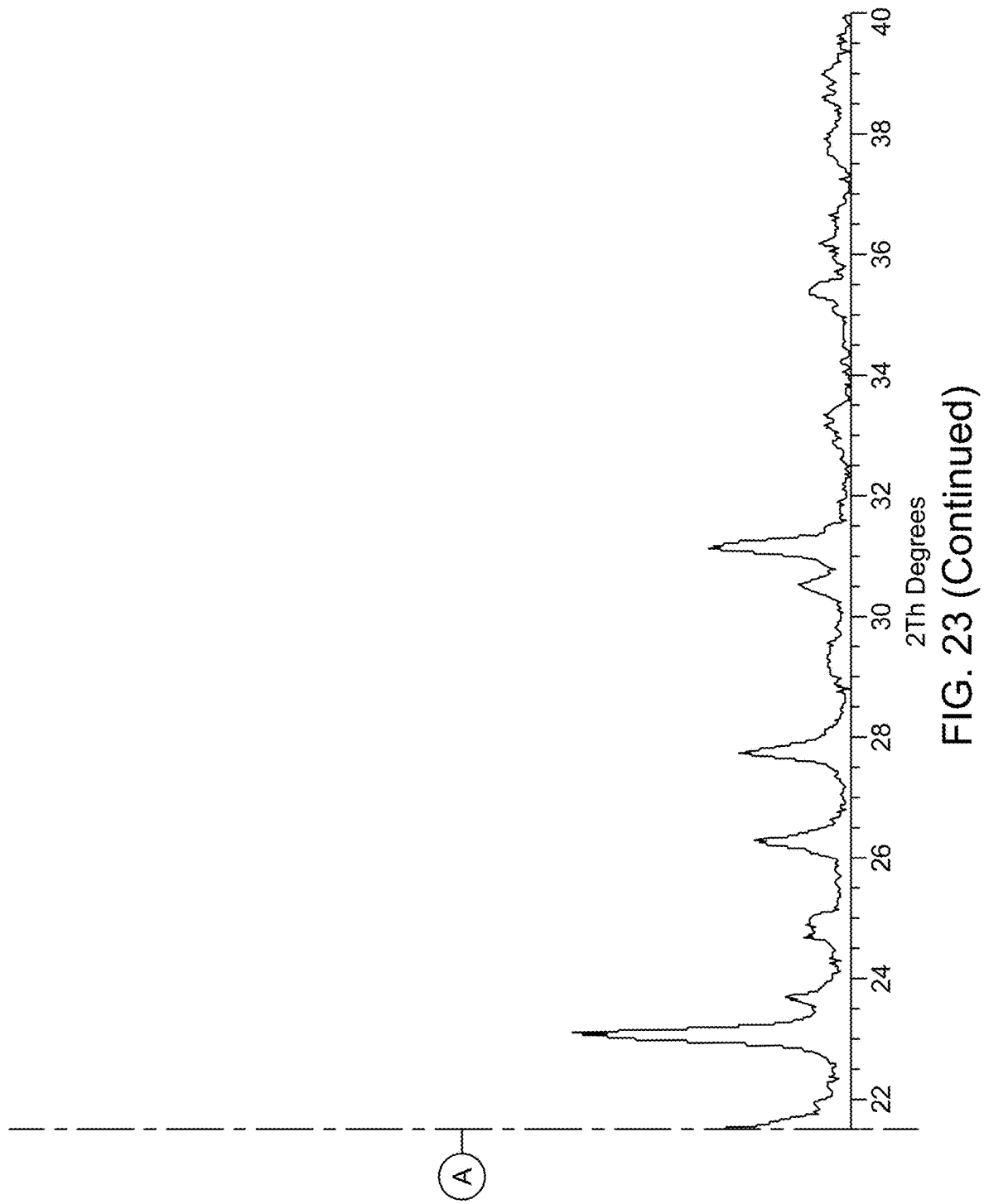

The XRPD pattern of Compound 1 Form C collected from the scaled-up preparation is shown in FIG. 23. Comparison of observed XRPD pattern of Compound 1 Form C corresponds well with the calculated XRPD pattern (FIG. 22).

Figure 24:
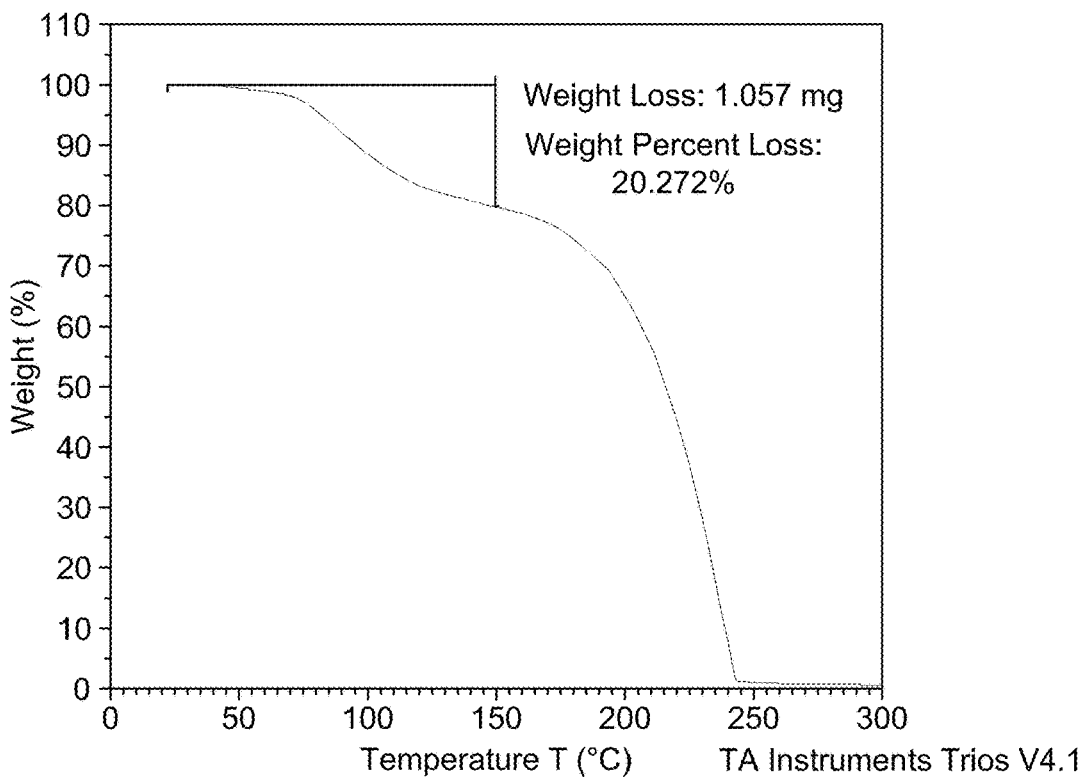
FIG. 24 provides TGA curve of Compound 1 Form C.

TGA of Compound 1 Form C is shown in FIG. 24. A weight loss of 20.27% was observed up to 150° C. Observed weight loss correlated well with calculated percentage of propylene glycol in crystal lattice based on single crystal X-ray diffraction (17.76%).

Figure 25:
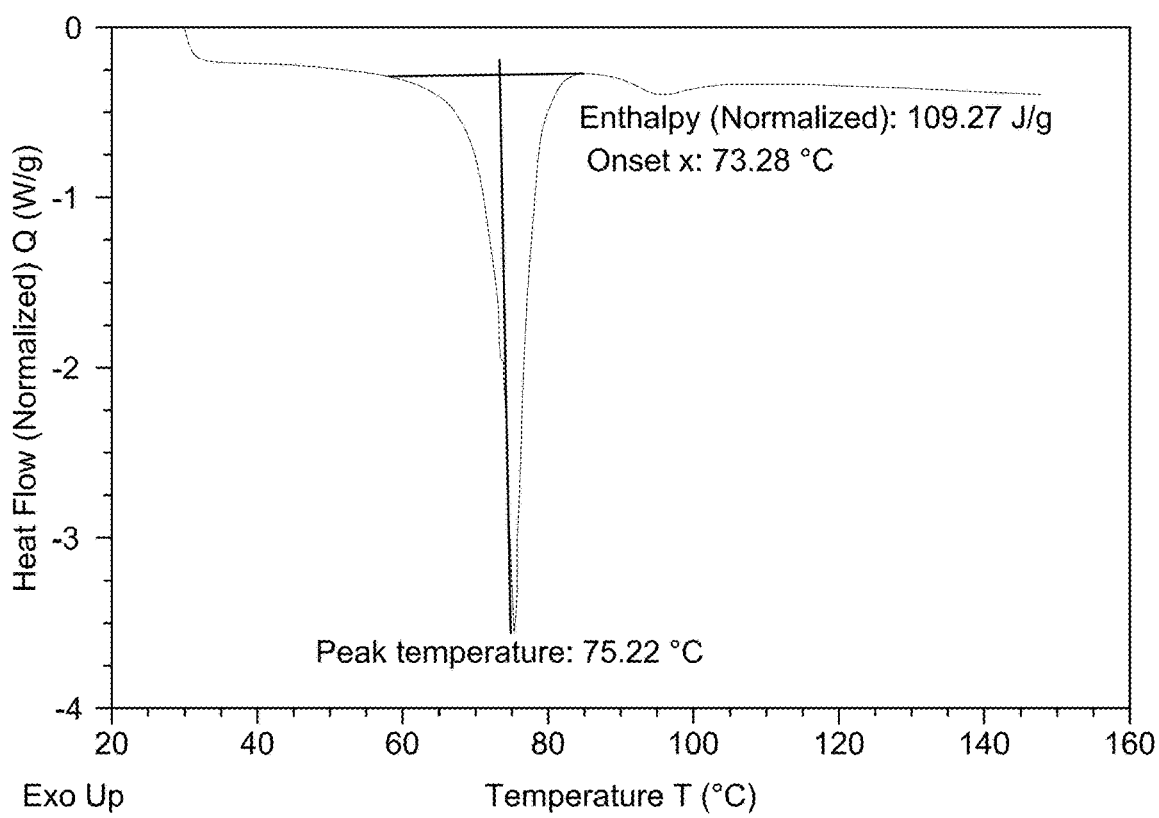
FIG. 25 provides DSC thermogram of Compound 1 Form C.

DSC of Compound 1 Form C is shown in FIG. 25. One endotherm was observed at 75.22° C.

Form D

Compound 1 Form D was prepared as follows: ~500 mg of Compound 1 Lot I was dissolved in a solvent mixture (250 µl of ethylene glycol and 1500 µl of methyl isobutyl ketone) while heating at 50° C. The resultant solution was kept at −27° C. for 48 hours to yield Compound 1 Form D. Solid was collected by filtration using 0.45 µm PTFE syringe filter.

Figure 42C:
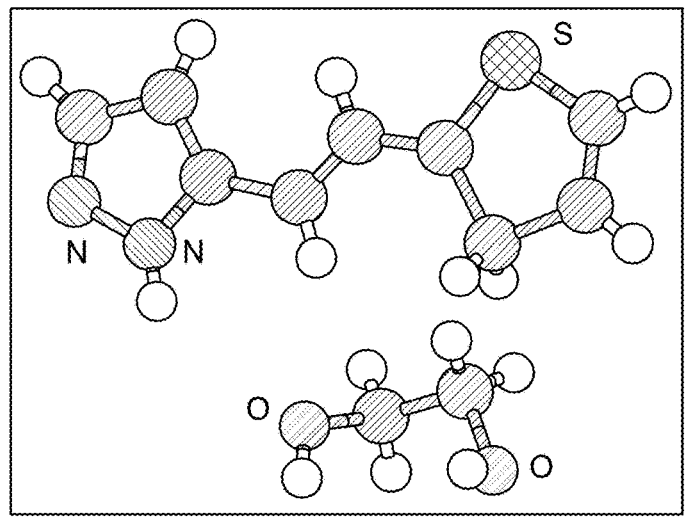
FIG. 42C provides single crystal X-ray crystallography of Compound 1 Form D. N, S, and O atoms are labeled; unlabeled non-hydrogen atoms are carbon.

Single crystal X-ray diffraction of Compound 1 Form D was obtained and showed that Compound 1 Form D is a ethylene glycol solvate (2:1 Compound 1:ethylene glycol) (FIG. 42C). Crystal data and structure refinement parameters are summarized below:

| | |
|---|---|
| Temperature (K) | 278.15 |
| Crystal system | Orthorhombic |
| Space group | Pbcn |
| a (Å) | 28.544(3) |
| b (Å) | 7.4452(8) |
| c (Å) | 9.8184(10) |
| α (°) | 90 |
| β (°) | 90 |
| γ (°) | 90 |
| Volume (Å$^3$) | 2086.6(4) |

Figure 26:
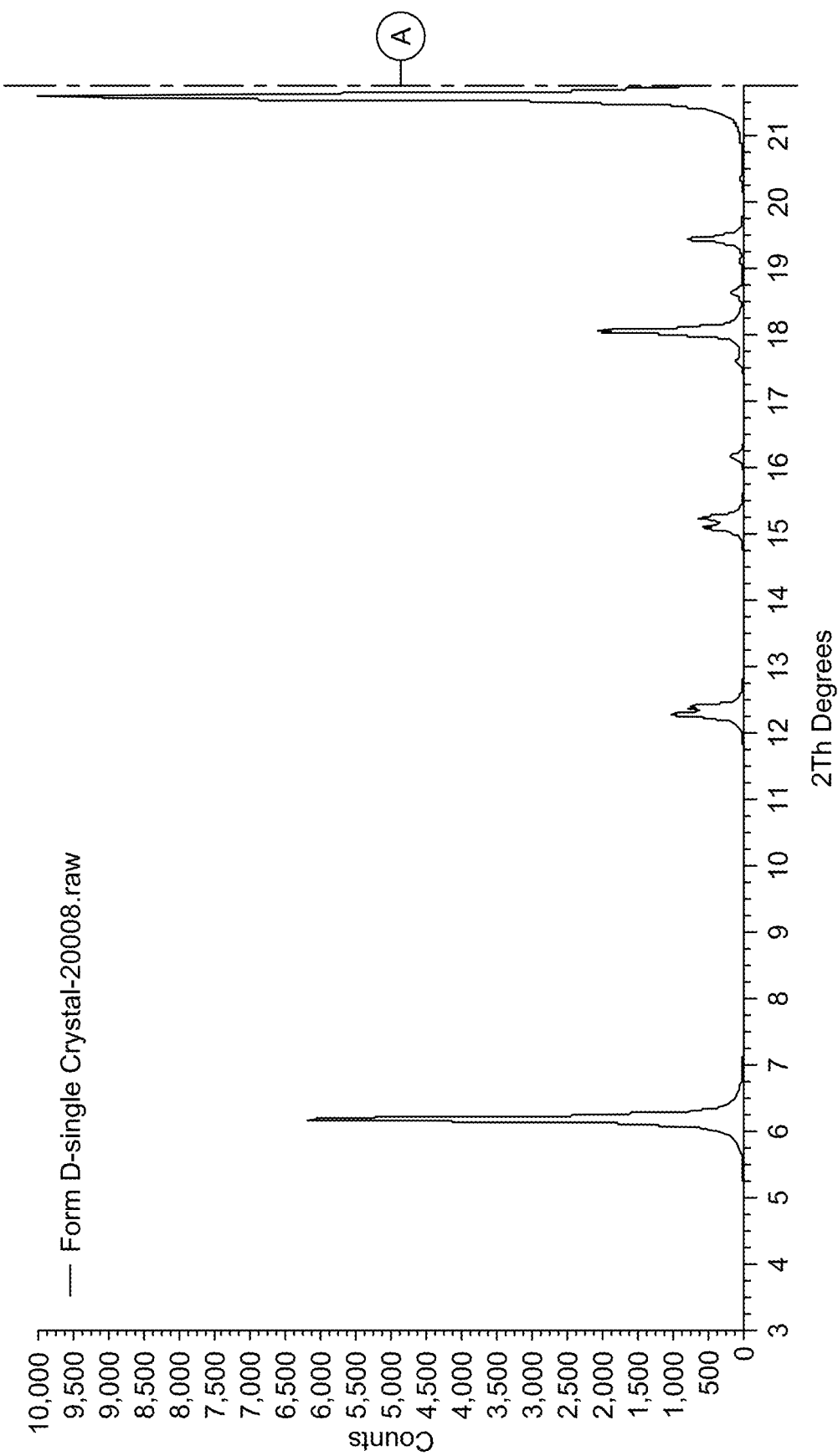
FIG. 26 provides XRPD pattern of Compound 1 Form D calculated from single crystal X-ray diffraction data.
Figure 26:
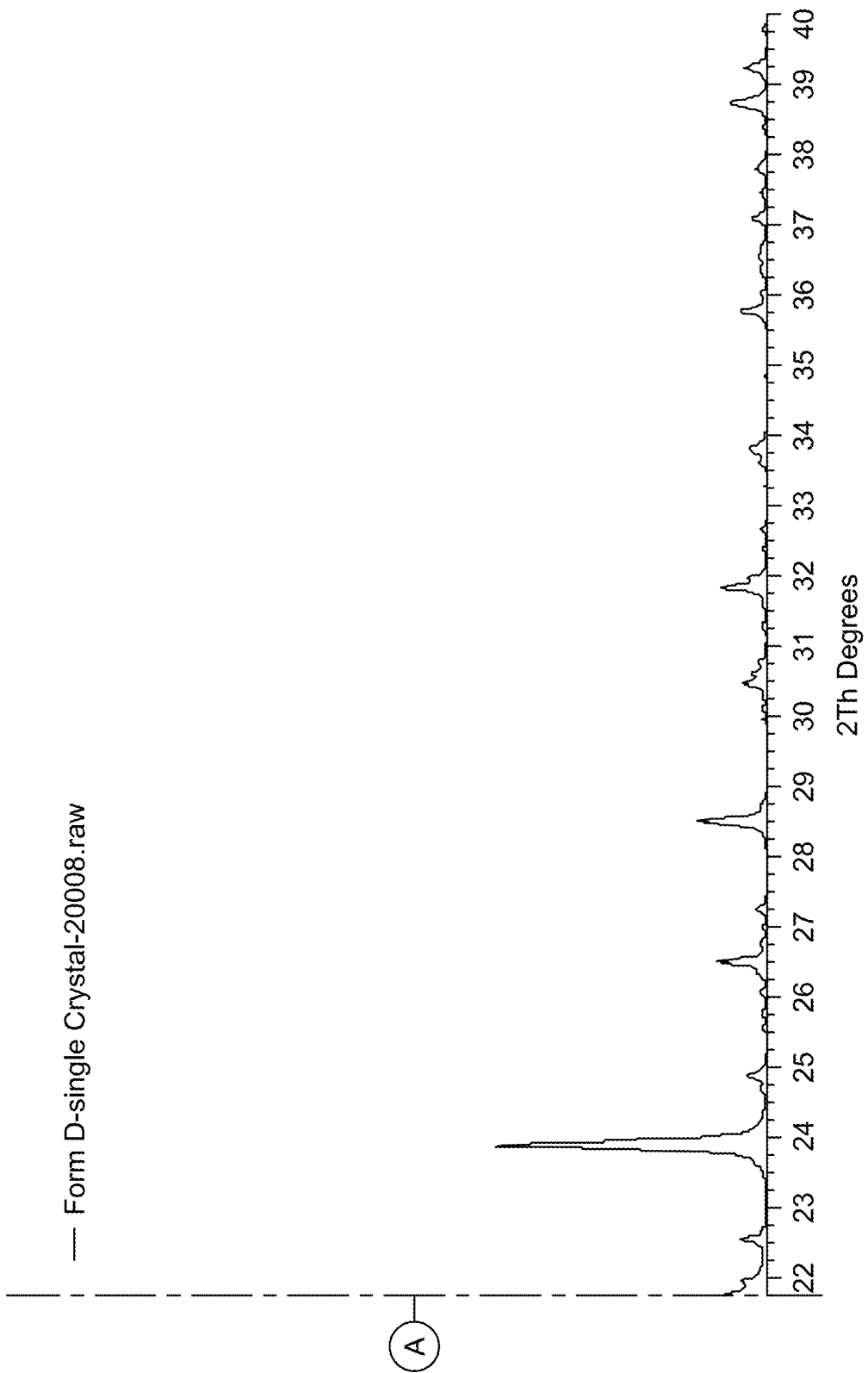

The XRPD pattern of Compound 1 Form D calculated from single crystal X-ray diffraction data is shown in FIG. 26 and is summarized below:

| 2θ (°) | d-spacing (Å) | Intensity Counts (I) |
|---|---|---|
| 6.19 | 14.28 | 6185 |
| 12.28 | 7.20 | 1019 |
| 12.38 | 7.14 | 769.5 |
| 15.10 | 5.86 | 584.0 |
| 15.24 | 5.81 | 638.3 |
| 16.17 | 5.48 | 206.6 |
| 17.60 | 5.03 | 118.4 |
| 18.06 | 4.91 | 2066 |
| 18.63 | 4.76 | 175.5 |
| 19.11 | 4.64 | 56.9 |
| 19.44 | 4.56 | 774.4 |
| 20.35 | 4.36 | 51.4 |
| 21.58 | 4.11 | 10000 |
| 21.95 | 4.05 | 334.6 |
| 22.55 | 3.94 | 349.9 |
| 23.88 | 3.72 | 3614 |
| 24.70 | 3.60 | 97.3 |
| 24.88 | 3.58 | 260.0 |
| 25.57 | 3.48 | 60.9 |
| 25.76 | 3.46 | 70.1 |
| 26.07 | 3.42 | 88.3 |
| 26.33 | 3.38 | 141.1 |
| 26.50 | 3.36 | 646.6 |
| 26.75 | 3.33 | 100.4 |
| 26.99 | 3.30 | 52.9 |
| 27.25 | 3.27 | 148.4 |
| 28.51 | 3.13 | 925.8 |
| 28.72 | 3.11 | 94.2 |
| 29.96 | 2.98 | 44.2 |
| 30.10 | 2.97 | 72.2 |
| 30.26 | 2.95 | 54.3 |
| 30.47 | 2.93 | 305.5 |

| 2θ (°) | d-spacing (Å) | Intensity Counts (I) |
| --- | --- | --- |
| 30.62 | 2.92 | 204.7 |
| 30.75 | 2.90 | 119.6 |
| 31.27 | 2.86 | 69.2 |
| 31.57 | 2.83 | 62.0 |
| 31.83 | 2.81 | 617.8 |
| 31.97 | 2.80 | 259.2 |
| 32.38 | 2.76 | 59.6 |
| 32.67 | 2.74 | 83.2 |
| 33.61 | 2.66 | 112.6 |
| 33.82 | 2.65 | 233.2 |
| 34.84 | 2.57 | 17.0 |
| 35.78 | 2.51 | 344.8 |
| 36.02 | 2.49 | 92.8 |
| 36.36 | 2.47 | 95.0 |
| 36.53 | 2.46 | 110.3 |
| 36.66 | 2.45 | 98.4 |
| 37.10 | 2.42 | 203.5 |
| 37.44 | 2.40 | 74.6 |
| 37.81 | 2.38 | 129.3 |
| 38.38 | 2.34 | 47.4 |
| 38.72 | 2.32 | 499.3 |
| 39.24 | 2.29 | 300.7 |
| 39.78 | 2.26 | 61.9 |

Figure 27:
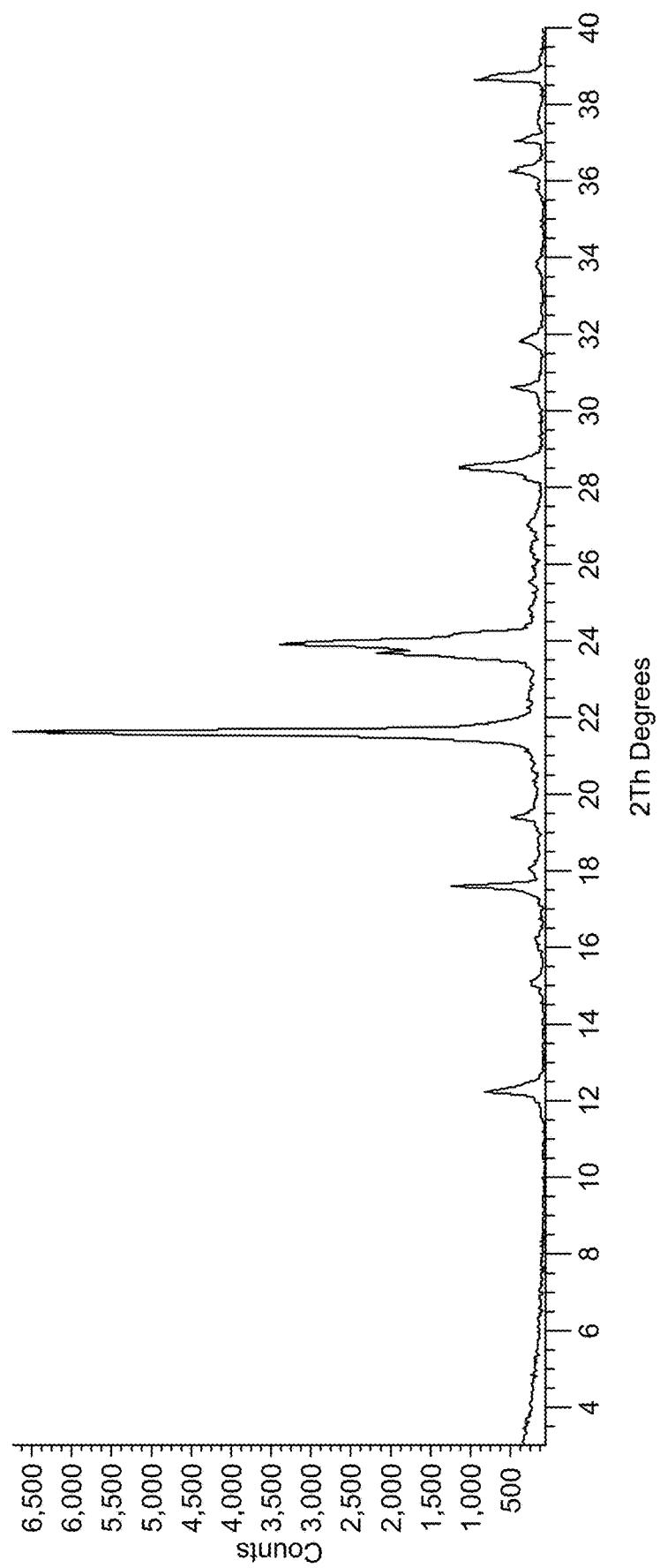
FIG. 27 provides XRPD pattern of Compound 1 Form D.

The XRPD pattern of Compound 1 Form D collected from the scaled-up preparation is shown in FIG. 27. Comparison of observed XRPD pattern of Compound 1 Form D corresponds well with the calculated XRPD pattern (FIG. 26).

Figure 28:
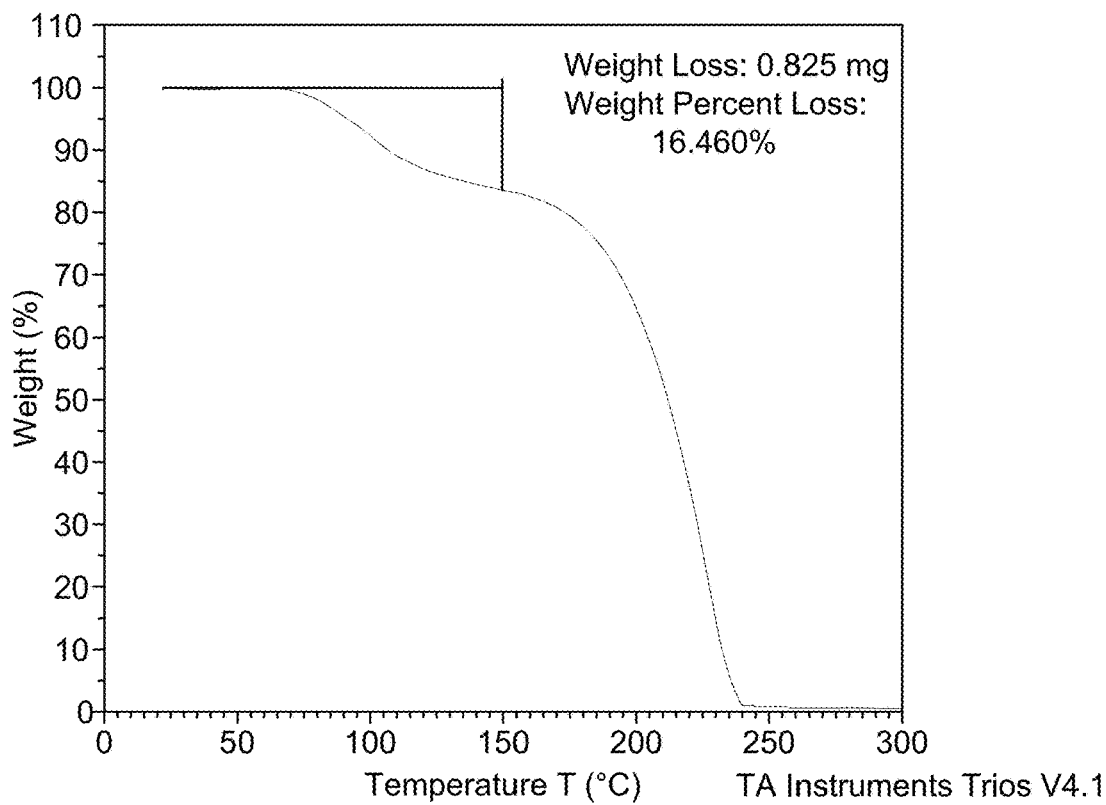
FIG. 28 provides TGA curve of Compound 1 Form D.

TGA of Compound 1 Form D is shown in FIG. 28. A weight loss of 16.46% was observed up to 150° C. Observed weight loss correlated well with calculated percentage of ethylene glycol in crystal lattice based on single crystal X-ray diffraction (14.97%).

Figure 29:
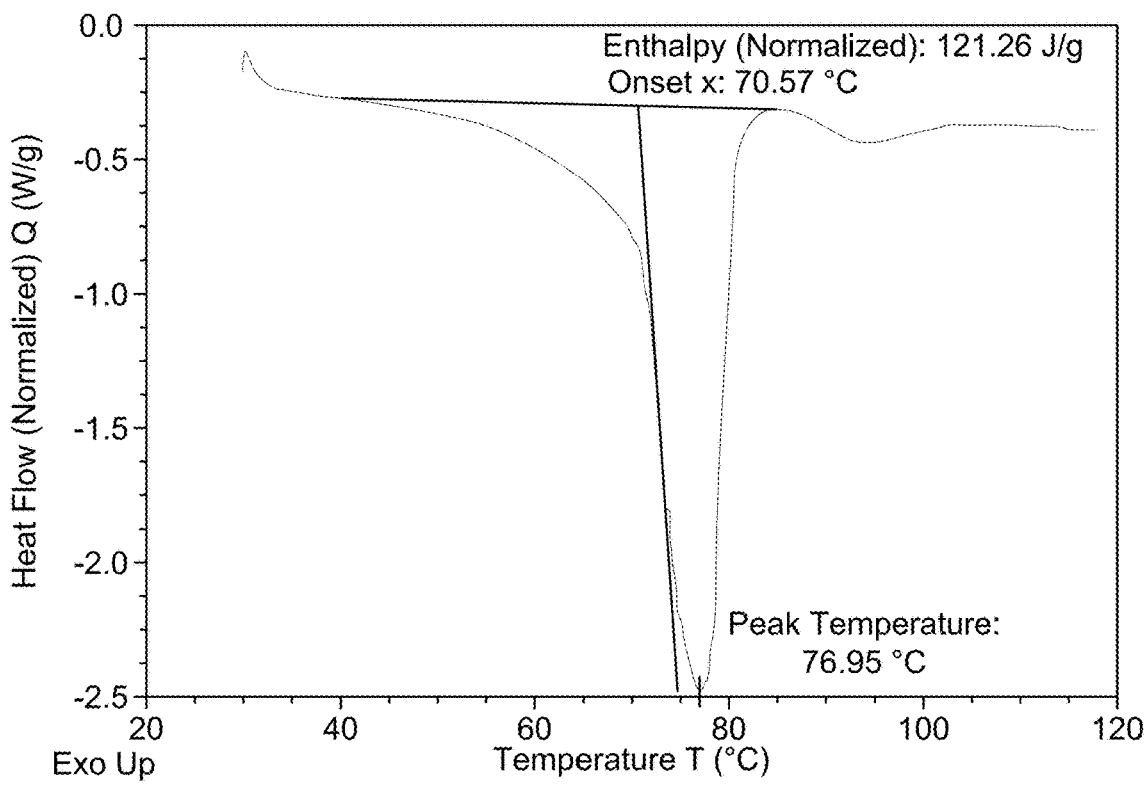
FIG. 29 provides DSC thermogram of Compound 1 Form D.

DSC of Compound 1 Form D is shown in FIG. 29. One endotherm was observed at 76.95° C.

Example 5: Dynamic Vapor Sorption of Compound 1 Solid Forms

Moisture sorption/desorption data were collected on a DVS-intrinsic vapor sorption analyzer (Surface Measurement Systems NA, Allentown, Pa., USA) and operating with DVS-intrinsic control software (Version 1.0.5.1). Samples were not dried prior to analysis. Sorption and desorption data were collected over a range from 5% to 98% relative humidity (RH) via 5% RH increments under a nitrogen purge. The equilibrium criterion used for analysis was less than 0.005% weight change in 10 min with a maximum equilibration time of 6 h.

Figure 30:
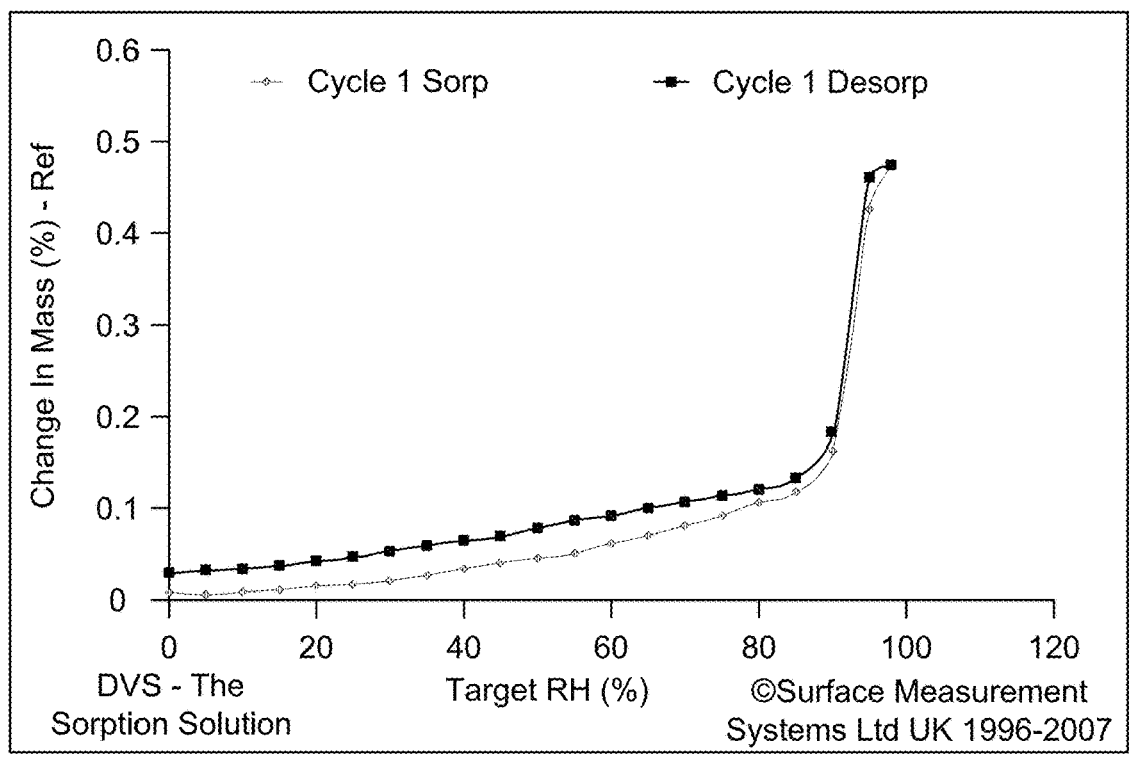
FIG. 30 provides dynamic vapor sorption (DVS) of Compound 1 Form A.

DVS of Form A is shown in FIG. 30. Form A absorbed maximum of 0.47% even at 98% RH, which confirms that Form A is non-hygroscopic. In addition no hysterisis is observed, which indicates the material did not change form.

Figure 31:
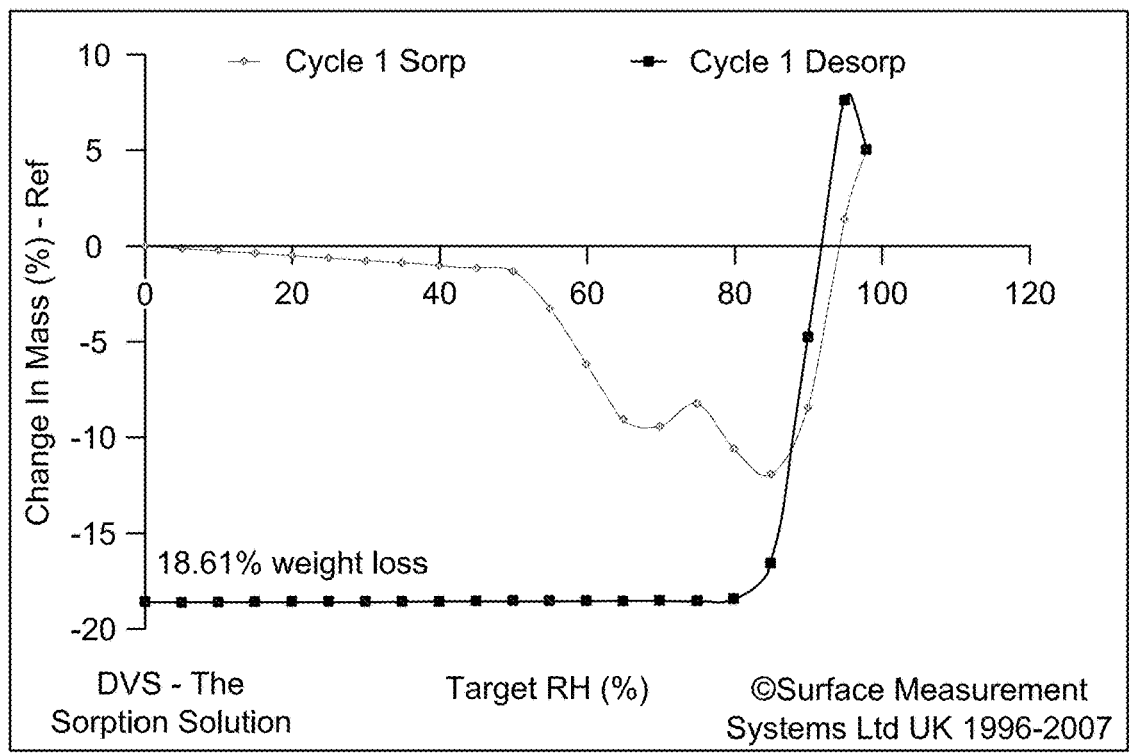
FIG. 31 provides dynamic vapor sorption (DVS) of Compound 1 Form C.

DVS of Form C is shown in FIG. 31. Form C exhibited weight loss of 18.61% throughout the experiment and displayed indications of a possible form change during the experiment. Weight loss observed in DVS closely matches weight of volatile components present in Form C (17.76%).

Figure 32:
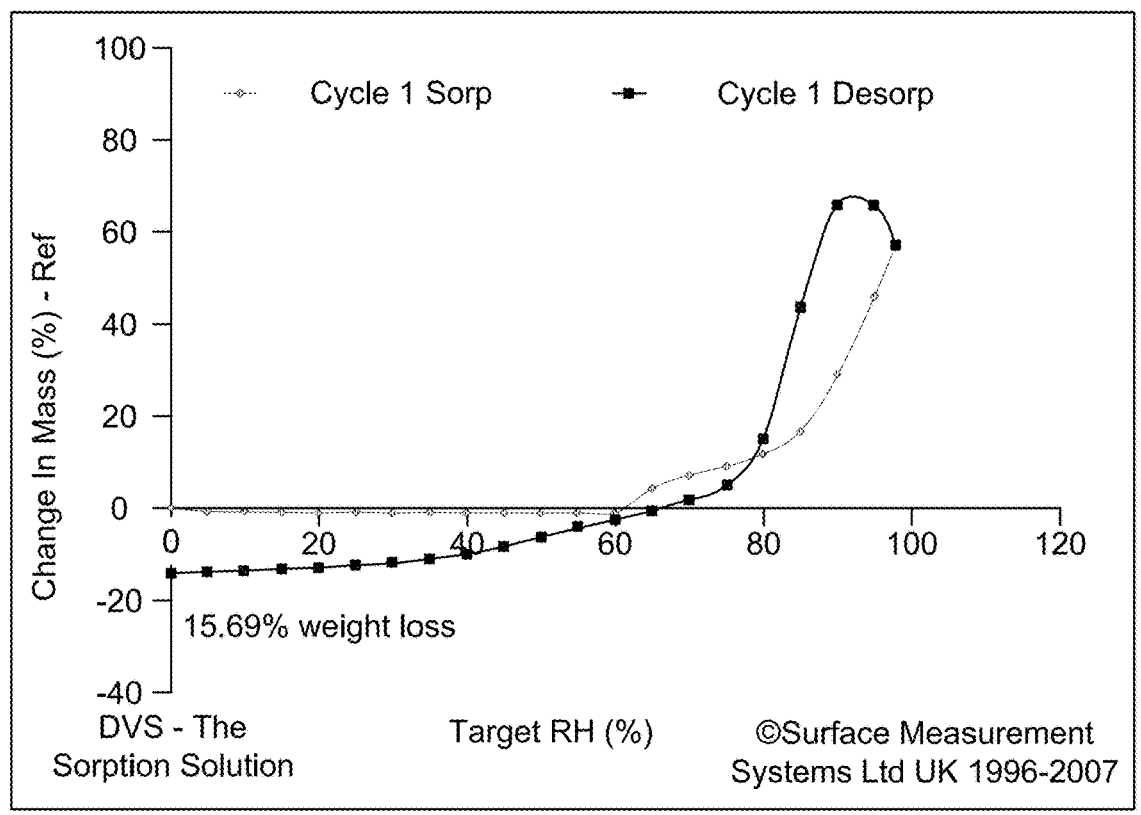
FIG. 32 provides dynamic vapor sorption (DVS) of Compound 1 Form D.

DVS of Form D is shown in FIG. 32. Form D exhibited weight loss of 15.69% observed throughout the experiment and displayed indications of a possible form change during the experiment. Weight loss observed in DVS closely matches weight of volatile components present in Form D (14.97%).

Figure 33:
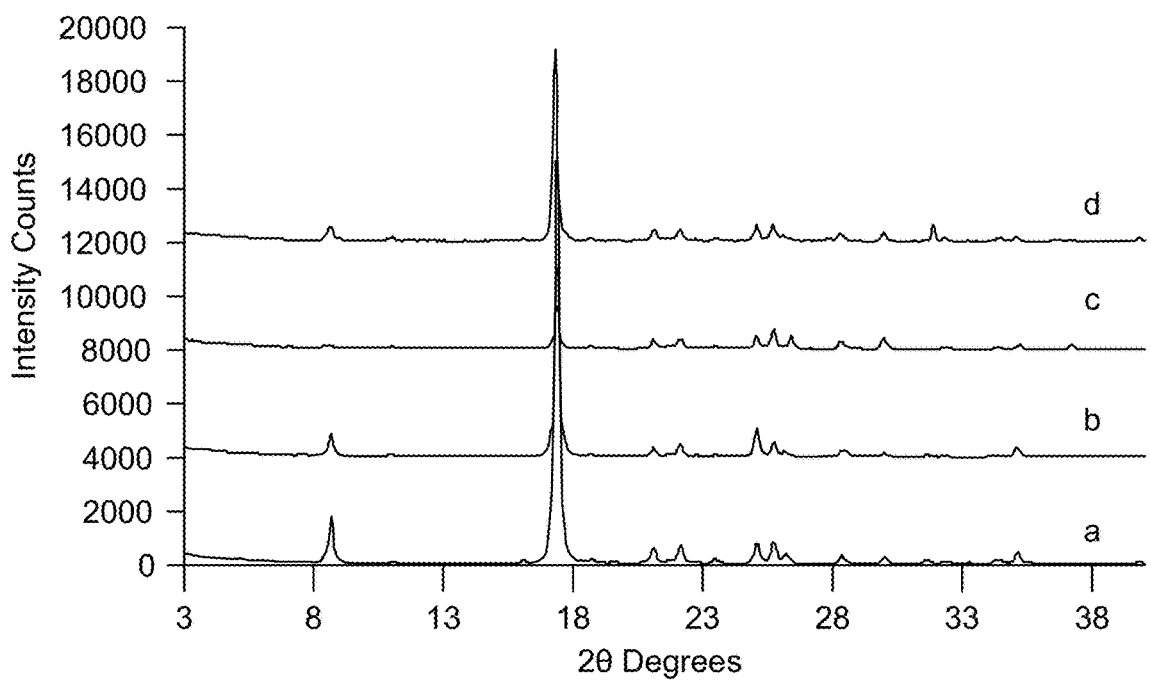
FIG. 33 provides XRPD patterns collected on the materials recovered after DVS (a: Form A (calculated); b: Form A after DVS; c: Form C after DVS; d: Form D after DVS).

XRPD was collected on the materials recovered after the dynamic moisture sorption experiments described above. As can be seen in FIG. 33, Form A exhibited no change during the experiment, while Form C and Form D converted to Form A during the experiment. This data suggest that Form A is more stable compared to Form C and Form D and that no special storage conditions, particularly with respect to moisture, are required for Form A.

Example 6: Slurry and Competitive Slurry Experiments

Figure 34:
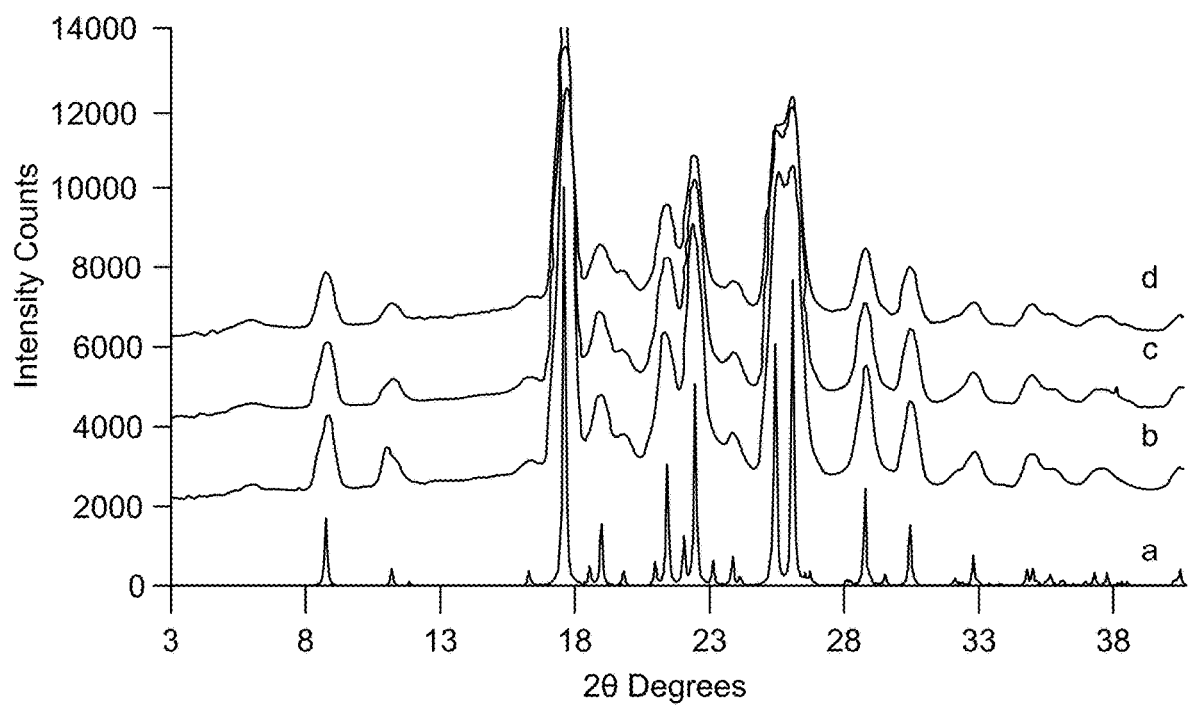
FIG. 34 provides XRPD results of slurry experiments (a: Form A (calculated); b: Form A after slurrying in IPA at RT for 3 days; c: Form C after slurrying in IPA at RT for 3 days; d: Form D after slurrying in IPA at RT for 3 days).
Figure 35:
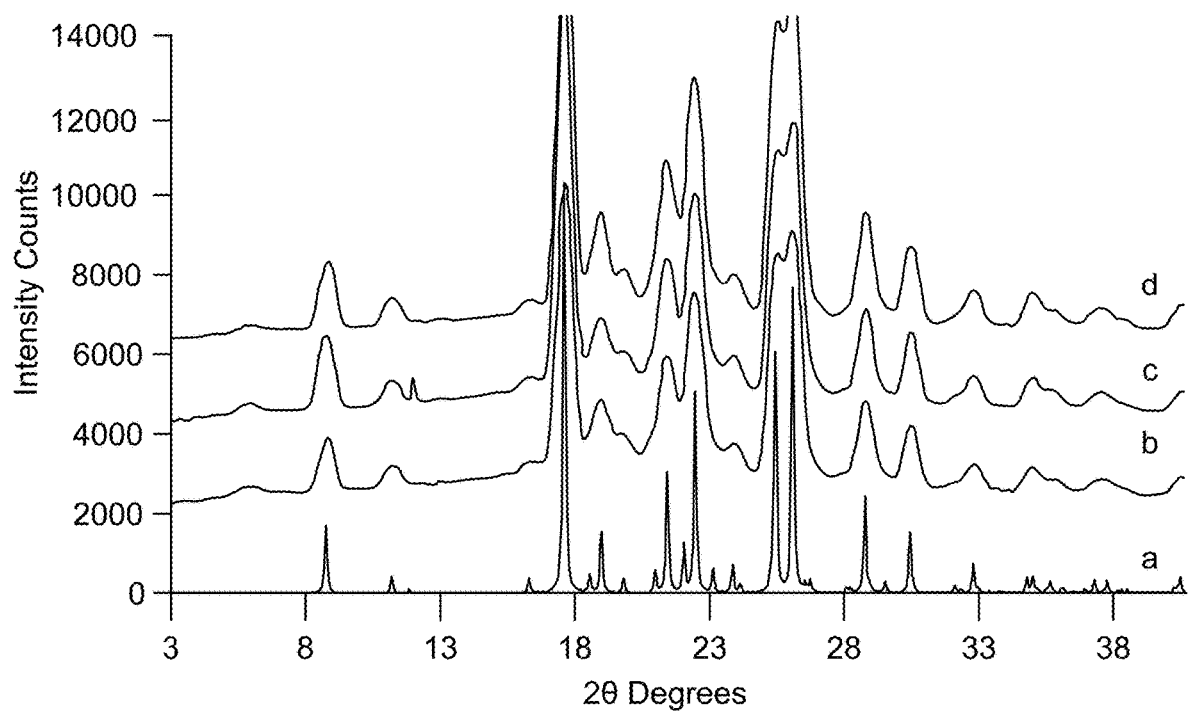
FIG. 35 provides XRPD results of competitive slurry experiments (a: Form A (calculated); b: Form A+C after slurrying in IPA at RT for 3 days; c: Form A+D after slurrying in IPA at RT for 3 days; d: Form C+D after slurrying in IPA at RT for 3 days).

Slurry and competitive slurry experiments were performed to determine the relative stability of Compound 1 solid forms. In a typical experiment, excess of a Compound 1 solid form or mixture thereof was suspended in isopropyl alcohol and stirred at room temperature for 72 hours. Resulting suspensions were filtered using a 0.45 μm PTFE syringe filter to isolate the solids. Solids were then analyzed by XRPD. XRPD results are summarized in FIG. 34 and FIG. 35. Results of slurry and competitive slurry experiments are summarized below:

| Starting Material(s) | Resultant Material |
| --- | --- |
| Form A | Form A |
| Form C | Form A |
| Form D | Form A |
| Form A and Form C | Form A |
| Form A and Form D | Form A |
| Form C and Form D | Form A |

Example 7: Solid State Stability of Compound 1 Solid Forms

Figure 36:
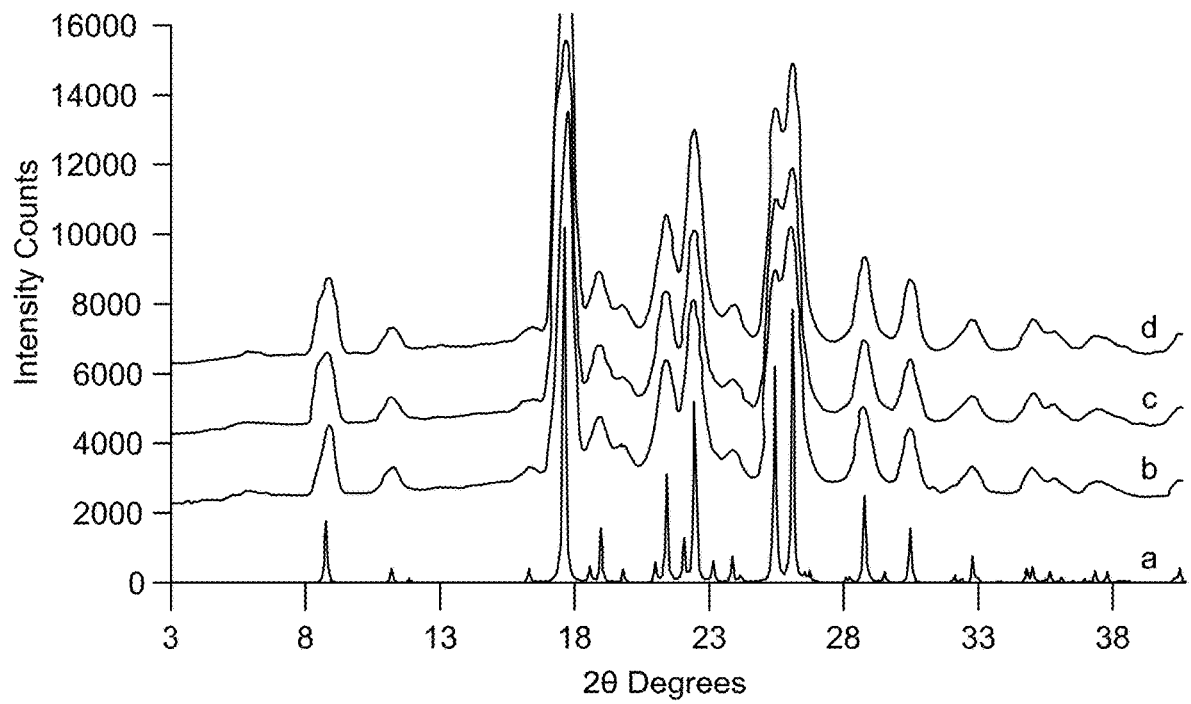
FIG. 36 provides XRPD results of stability studies of Form A (a: Form A (calculated); b: Form A after storage for 4 weeks at at 2° C.; c: Form A after storage for 4 weeks at 25° C./60% RH; d: Form A after storage for 4 weeks at 40° C./75% RH).
Figure 37:
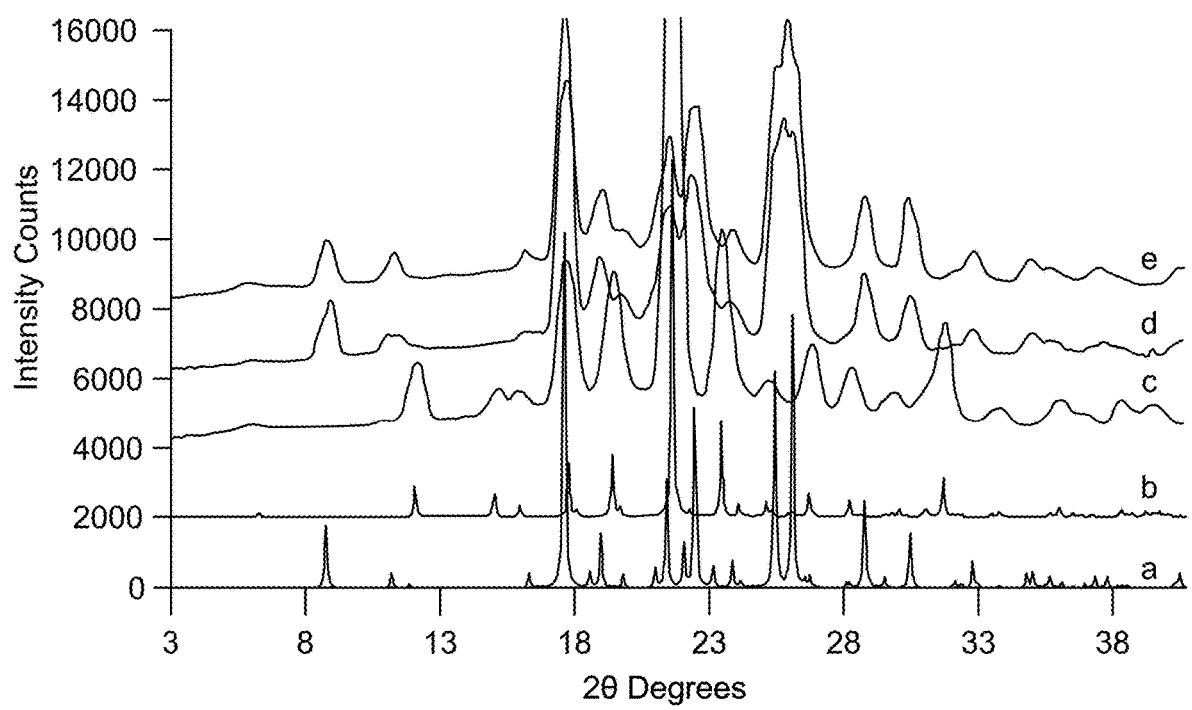
FIG. 37 provides XRPD results of stability studies of Form C (a: Form A (calculated); b: Form C (calculated); c: Form C after storage for 4 weeks at at 2° C.; d: Form C after storage for 4 weeks at 25° C./60% RH; e: Form C after storage for 4 weeks at 40° C./75% RH).
Figure 38:
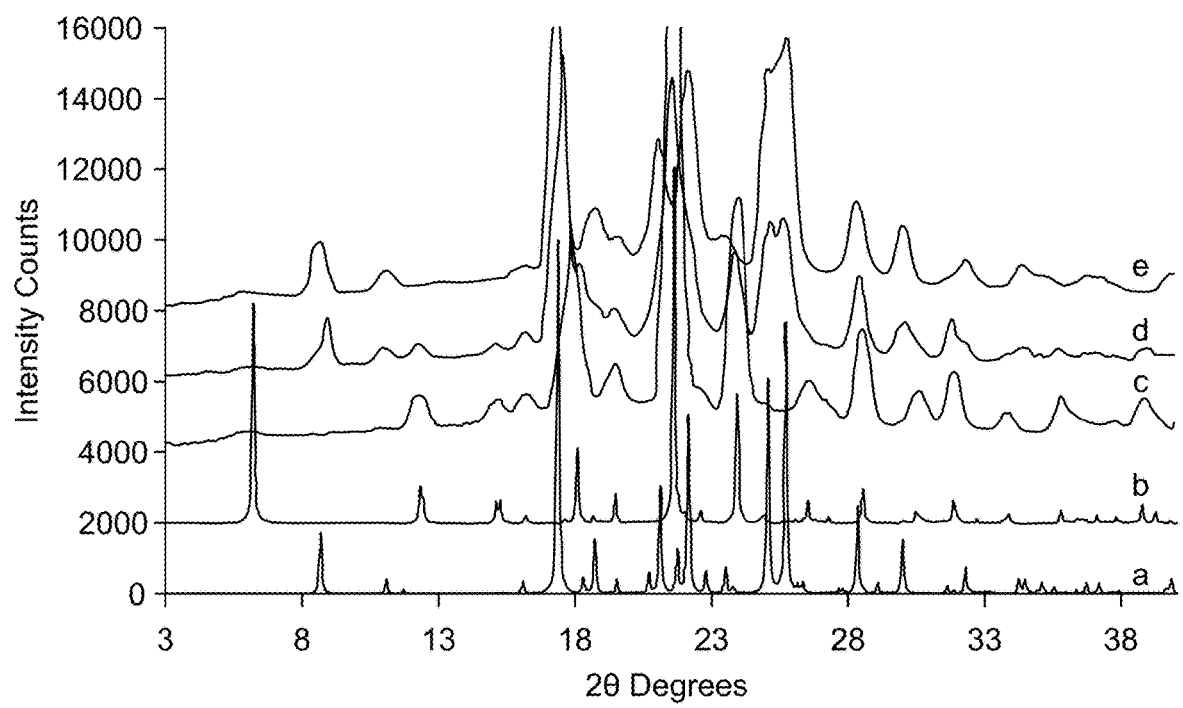
FIG. 38 provides XRPD results of stability studies of Form D (a: Form A (calculated); b: Form D (calculated); c: Form D after storage for 4 weeks at at 2° C.; d: Form D after storage for 4 weeks at 25° C./60% RH; e: Form D after storage for 4 weeks at 40° C./75% RH).

Solid state stability of Compound 1 solid forms was assessed by storing samples of each solid form at 2-8° C., 25° C./60% RH and 40° C./75% RH. Samples were taken after 1 week, 2 weeks, 3 weeks, and 4 weeks, and XRPD was collected. FIG. 36, FIG. 37, and FIG. 38 shows XRPD data after 4 weeks for each form under each condition. Results of solid state stability studies are summarized below:

| | Results after: | | | |
| --- | --- | --- | --- | --- |
| Starting Form | 1 week | 2 weeks | 3 weeks | 4 weeks |
| Form A | | | | |
| 2-8° C. | Form A | Form A | Form A | Form A |
| 25° C./60% RH | Form A | Form A | Form A | Form A |
| 40° C./75% RH | Form A | Form A | Form A | Form A |
| Form C | | | | |
| 2-8° C. | Form C | Form C | Form C | Form C |
| 25° C./60% RH | Form C | Form C | Form C | Form A |
| 40° C./75% RH | Form A | Form A | Form A | Form A |
| Form D | | | | |
| 2-8° C. | Form D | Form D | Form D | Form D |
| 25° C./60% RH | Form A + D | Form A + D | Form A + D | Form A + D |
| 40° C./75% RH | Form A | Form A | Form A | Form A |

Example 8: UV Stability of Compound 1 Solid Forms

UV stability of Compound 1 solid forms was assessed by placing the samples in a dark sealed box at room temperature under UV lamps (4 watts, ~2 cm distances from the sample).

Figure 39:
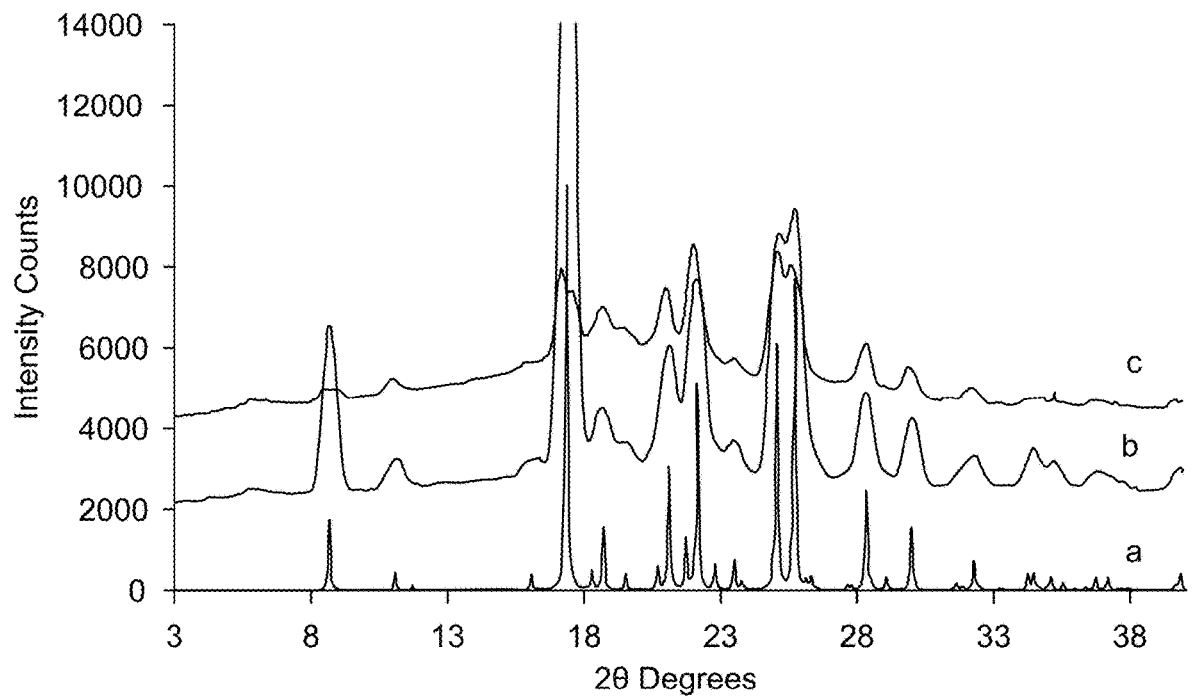
FIG. 39 provides XRPD results of UV stability studies of Form A (a: Form A (calculated); b: Form A after storage for 1 week at 365 nm; c: Form A after storage for 1 week at 254 nm).
Figure 40:
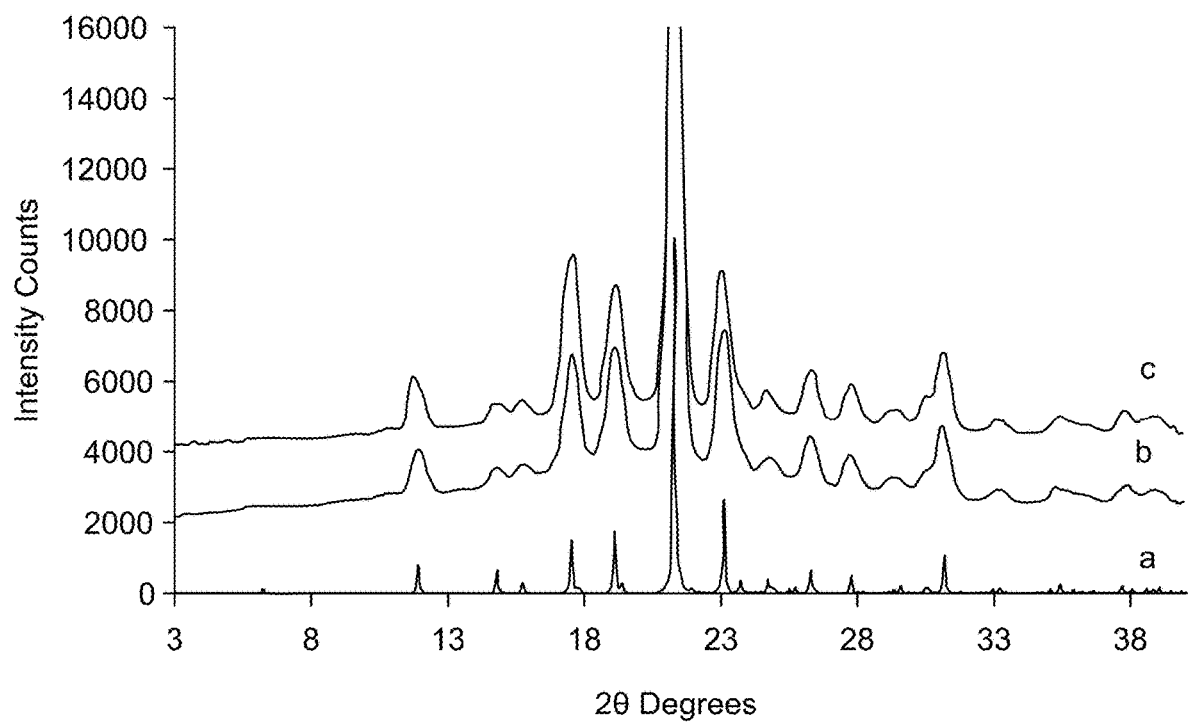
FIG. 40 provides XRPD results of UV stability studies of Form C (a: Form C (calculated); b: Form C after storage for 1 week at 365 nm; c: Form C after storage for 1 week at 254 nm).
Figure 41:
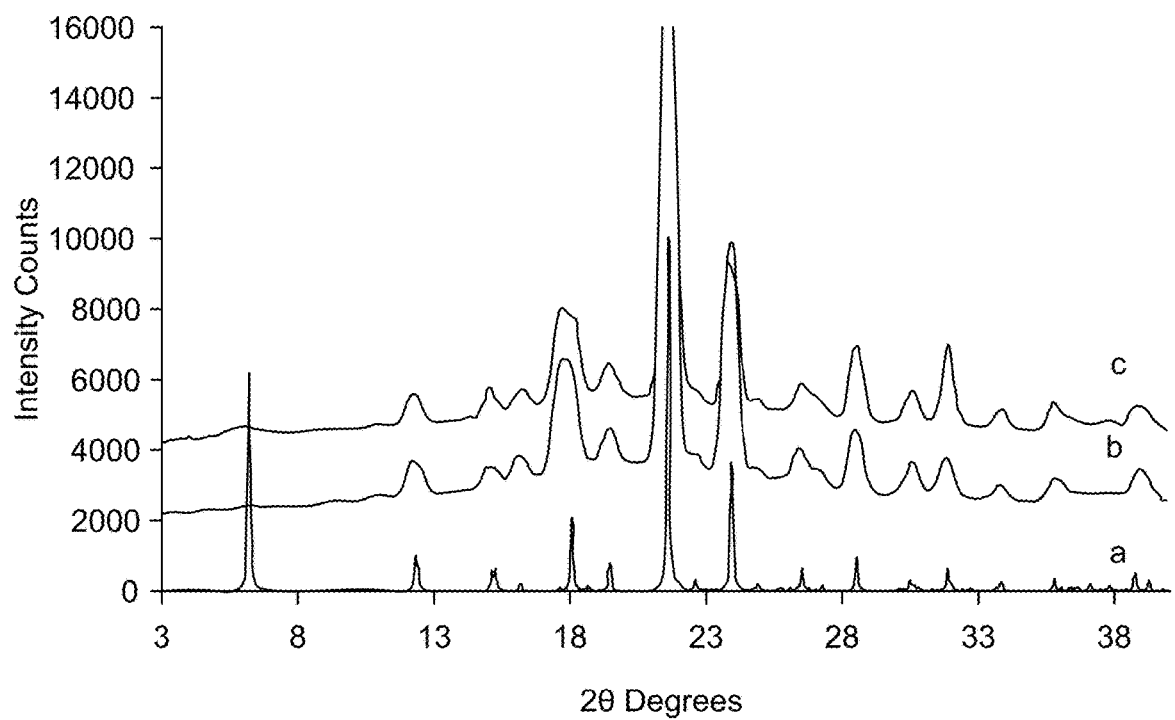
FIG. 41 provides XRPD results of UV stability studies of Form D (a: Form D (calculated); b: Form D after storage for 1 week at 365 nm; c: Form D after storage for 1 week at 254 nm).

Stability was assessed at two different wavelengths (254 nm and 365 nm). Samples were taken after 1 week, 2 weeks, 3 weeks, and 4 weeks, and XRPD and UPLC-MS were collected. FIG. 39, FIG. 40, and FIG. 41 shows XRPD results after 1 week for each form under each condition. Results are summarized below:

| Starting Material | Results after: | | | |
|---|---|---|---|---|
| | 1 week | 2 weeks | 3 weeks | 4 weeks |
| Form A | | | | |
| 254 nm | Form A (100% purity) | Form A (100% purity) | Form A (100% purity) | Form A (100% purity) |
| 365 nm | Form A (100% purity) | Form A (100% purity) | Form A (100% purity) | Form A (100% purity) |
| Form C | | | | |
| 254 nm | Form C (100% purity) | Form C (100% purity) | Form C + A (100% purity) | NA |
| 365 nm | Form C (100% purity) | NC (67% purity) | NC (56% purity) | NC (51% purity) |
| Form D | | | | |
| 254 nm | Form D (100% purity) | Form D (100% purity) | Form D (100% purity) | Form D (100% purity) |
| 365 nm | Form D (100% purity) | NC (65% purity) | NC (63% purity) | NC (61% purity) |

*NC: XRPD not collected due to low chemical purity as assessed by UPLC-MS; NA: Not available According to data shown above, Form A of Compound 1 shows greater stability than other forms under two different UV wavelengths (254 nm and 365 nm, respectively). This is particularly true under longer UV wavelength, i.e., 365 nm.

Example 9: Stability Studies of Solid Forms of Compound 1 at Different Temperatures Twenty mg each of Compound 1 Form A, Form C, and Form D were stored at 4° C., 22° C., and 50° C., protected from light. At specified time points, the purities of samples were monitored using UPLC-MS. No significant degradation of Compound 1 was observed, though changes in form would not be detected using this method. The results are shown below:

| Purity at 4° C.: | | | |
|---|---|---|---|
| | Purity, % | | |
| Date | Form A | Form C | Form D |
| Day 1 | 100 | 100 | 100 |
| Day 15 | 100 | 100 | 100 |
| Day 30 | 100 | 100 | 100 |

| Purity at 22° C.: | | | |
|---|---|---|---|
| | Purity, % | | |
| Date | Form A | Form C | Form D |
| Day 1 | 100 | 100 | 100 |
| Day 15 | 100 | 100 | 100 |
| Day 30 | 100 | 100 | 100 |

| Purity at 50° C.: | | | |
|---|---|---|---|
| | Purity, % | | |
| Date | Form A | Form C | Form D |
| Day 1 | 100 | 100 | 100 |
| Day 15 | 100 | 100 | 100 |
| Day 30 | 100 | 100 | 100 |

The above data show that Compound 1 are stable under short-term storage at 40° C., 22° C., and 50° C., regardless of form.

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A crystalline solid form of Compound 1:

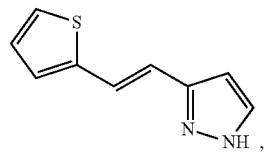

wherein the solid form is characterized by one or more peaks in its X-ray powder diffraction pattern (XRPD) selected from those at about 8.64, about 11.04, about 17.34, about 25.06, and about 25.70 degrees 2-theta.

2. The solid form of claim 1, wherein the solid form is characterized by peaks in its XRPD at about 8.64, about 11.04, about 17.34, about 25.06, and about 25.70 degrees 2-theta.

3. The solid form of claim 1, wherein the solid form is characterized by substantially all of the peaks in its XRPD pattern at about:

| Degrees 2-Theta |
|---|
| 8.64 |
| 11.04 |
| 11.67 |
| 16.06 |
| 17.34 |
| 18.27 |
| 18.69 |
| 19.49 |
| 20.66 |
| 21.09 |
| 21.70 |
| 22.10 |
| 22.76 |
| 23.46 |
| 23.74 |
| 25.06 |
| 25.70 |
| 26.12 |
| 26.32 |
| 27.64 |
| 27.78 |
| 28.31 |
| 28.49 |
| 29.04 |
| 29.95 |
| 31.59 |
| 31.82 |

| Degrees 2-Theta |
| --- |
| 32.25 |
| 33.22 |
| 34.21 |
| 34.42 |
| 35.08 |
| 35.53 |
| 36.33 |
| 36.70 |
| 37.16 |
| 37.65 |
| 39.02 |
| 39.60 |
| 39.81. |

4. The solid form of claim 1, wherein the solid form is characterized by a weight loss of about 0.6% up to 150° C. using thermogravimetric analysis.

5. The solid form of claim 1, wherein the solid form is characterized by an endotherm at about 116.42° C. using differential scanning calorimetry.

6. A crystalline solid form of Compound 1:

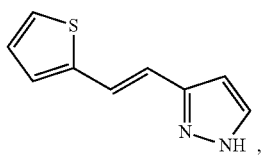

wherein the solid form is a propylene glycol solvate characterized by one or more peaks in its XRPD pattern selected from those at about 11.88, about 17.50, about 19.08, about 21.28, and about 23.07 degrees 2-theta.

7. The solid form of claim 6, wherein the solid form is characterized by peaks in its XRPD pattern at about 11.88, about 17.50, about 19.08, about 21.28, and about 23.07 degrees 2-theta.

8. The solid form of claim 6, wherein the solid form is characterized by substantially all of the peaks in its XRPD pattern at about:

| Degrees 2-Theta |
| --- |
| 6.20 |
| 11.88 |
| 12.41 |
| 14.79 |
| 15.72 |
| 17.50 |
| 17.78 |
| 19.08 |
| 19.36 |
| 21.28 |
| 21.89 |
| 23.07 |
| 23.69 |
| 23.92 |
| 24.70 |
| 24.90 |
| 25.50 |
| 25.71 |
| 26.28 |
| 27.74 |
| 28.13 |
| 29.10 |
| 29.31 |

| Degrees 2-Theta |
| --- |
| 29.55 |
| 30.51 |
| 31.15 |
| 31.76 |
| 32.93 |
| 33.19 |
| 33.36 |
| 34.63 |
| 35.05 |
| 35.40 |
| 35.90 |
| 36.20 |
| 36.60 |
| 37.57 |
| 37.69 |
| 38.05 |
| 38.54 |
| 38.80 |
| 39.05 |
| 39.46 |
| 39.82. |

9. The solid form of claim 6, wherein the solid form is characterized by a weight loss of about 20.27% up to 150° C. using thermogravimetric analysis.

10. The solid form of claim 6, wherein the solid form is characterized by an endotherm at about 75.22° C. using differential scanning calorimetry.

11. A crystalline solid form of Compound 1:

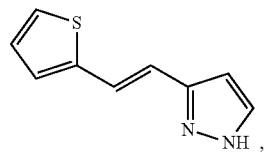

wherein the solid form is an ethylene glycol solvate characterized by one or more peaks in its XRPD pattern selected from those at about 12.28, about 15.10, about 18.06, about 21.58, and about 23.88 degrees 2-theta.

12. The solid form of claim 11, wherein the solid form is characterized by peaks in its XRPD pattern at about 12.28, about 15.10, about 18.06, about 21.58, and about 23.88 degrees 2-theta.

13. The solid form of claim 11, wherein the solid form is characterized by substantially all of the peaks in its XRPD pattern at about:

| Degrees 2-Theta |
| --- |
| 6.19 |
| 12.28 |
| 12.38 |
| 15.10 |
| 15.24 |
| 16.17 |
| 17.60 |
| 18.06 |
| 18.63 |
| 19.11 |
| 19.44 |
| 20.35 |
| 21.58 |
| 21.95 |
| 22.55 |

| Degrees 2-Theta |
| --- |
| 23.88 |
| 24.70 |
| 24.88 |
| 25.57 |
| 25.76 |
| 26.07 |
| 26.33 |
| 26.50 |
| 26.75 |
| 26.99 |
| 27.25 |
| 28.51 |
| 28.72 |
| 29.96 |
| 30.10 |
| 30.26 |
| 30.47 |
| 30.62 |
| 30.75 |
| 31.27 |
| 31.57 |
| 31.83 |
| 31.97 |
| 32.38 |
| 32.67 |
| 33.61 |
| 33.82 |
| 34.84 |
| 35.78 |
| 36.02 |
| 36.36 |
| 36.53 |
| 36.66 |
| 37.10 |
| 37.44 |
| 37.81 |
| 38.38 |
| 38.72 |
| 39.24 |
| 39.78. |

14. The solid form of claim 11, wherein the solid form is characterized by a weight loss of about 16.46% up to 150° C. using thermogravimetric analysis.

15. The solid form of claim 11, wherein the solid form is characterized by an endotherm at about 76.95° C. using differential scanning calorimetry.

16. The solid form of claim 3, wherein the solid form is characterized by a weight loss of about 0.6% up to 150° C. using thermogravimetric analysis.

17. The solid form of claim 3, wherein the solid form is characterized by an endotherm at about 116.42° C. using differential scanning calorimetry.

18. The solid form of claim 1, wherein the solid form is characterized by peaks in its X-ray powder diffraction pattern at about 8.64, about 11.04, about 17.34, about 25.06, and about 25.70 degrees 2-theta, corresponding to d-spacing of about 10.22, about 8.01, about 5.11, about 3.55, and about 3.46 angstroms.

19. The solid form of claim 1, wherein the solid form is characterized by substantially all of the peaks in its XRPD pattern at about, corresponding to d-spacing of:

| Degrees 2-Theta | d-spacing (Å) |
| --- | --- |
| 8.64 | 10.22 |
| 11.04 | 8.01 |
| 11.67 | 7.57 |
| 16.06 | 5.51 |
| 17.34 | 5.11 |
| 18.27 | 4.85 |
| 18.69 | 4.74 |
| 19.49 | 4.55 |
| 20.66 | 4.30 |
| 21.09 | 4.21 |
| 21.70 | 4.09 |
| 22.10 | 4.02 |
| 22.76 | 3.90 |
| 23.46 | 3.79 |
| 23.74 | 3.74 |
| 25.06 | 3.55 |
| 25.70 | 3.46 |
| 26.12 | 3.41 |
| 26.32 | 3.38 |
| 27.64 | 3.23 |
| 27.78 | 3.21 |
| 28.31 | 3.15 |
| 28.49 | 3.13 |
| 29.04 | 3.07 |
| 29.95 | 2.98 |
| 31.59 | 2.83 |
| 31.82 | 2.81 |
| 32.25 | 2.77 |
| 33.22 | 2.69 |
| 34.21 | 2.62 |
| 34.42 | 2.60 |
| 35.08 | 2.56 |
| 35.53 | 2.52 |
| 36.33 | 2.47 |
| 36.70 | 2.45 |
| 37.16 | 2.42 |
| 37.65 | 2.39 |
| 39.02 | 2.31 |
| 39.60 | 2.27 |
| 39.81 | 2.26. |

\* \* \* \* \*